(12) United States Patent
Luo et al.

(10) Patent No.: US 10,894,986 B2
(45) Date of Patent: Jan. 19, 2021

(54) COMPOSITIONS AND METHODS FOR TREATING OR PREVENTING PROSTATE CANCER AND FOR DETECTING ANDROGEN RECEPTOR VARIANTS

(71) Applicant: The Johns Hopkins University, Baltimore, MD (US)

(72) Inventors: Jun Luo, Clarksville, MD (US); George Steven Bova, Baltimore, MD (US); William Isaacs, Reisterstown, MD (US); Thomas Dunn, Baltimore, MD (US); Rong Hu, Catonsville, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 96 days.

(21) Appl. No.: 14/718,955

(22) Filed: May 21, 2015

(65) Prior Publication Data

US 2015/0344965 A1 Dec. 3, 2015

Related U.S. Application Data

(63) Continuation of application No. 12/988,299, filed as application No. PCT/US2009/002392 on Apr. 16, 2009, now Pat. No. 9,146,238.

(60) Provisional application No. 61/114,153, filed on Nov. 13, 2008, provisional application No. 61/124,328, filed on Apr. 16, 2008.

(51) Int. Cl.
| | |
|---|---|
| *G01N 33/53* | (2006.01) |
| *C12Q 1/6886* | (2018.01) |
| *C07K 16/28* | (2006.01) |
| *A61K 38/00* | (2006.01) |
| *G01N 33/574* | (2006.01) |

(52) U.S. Cl.
CPC ........ *C12Q 1/6886* (2013.01); *C07K 16/2869* (2013.01); *A61K 38/00* (2013.01); *C07K 2317/34* (2013.01); *C12Q 2600/118* (2013.01); *C12Q 2600/136* (2013.01); *C12Q 2600/156* (2013.01); *C12Q 2600/158* (2013.01); *C12Q 2600/16* (2013.01); *G01N 33/57434* (2013.01); *G01N 2333/723* (2013.01); *G01N 2500/00* (2013.01); *G01N 2800/50* (2013.01); *G01N 2800/52* (2013.01); *G01N 2800/54* (2013.01); *G01N 2800/56* (2013.01)

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. | |
| 4,877,611 A | 10/1989 | Cantrell | |
| 5,223,409 A | 6/1993 | Ladner et al. | |
| 5,225,539 A | 7/1993 | Winter | |
| 5,399,346 A | 3/1995 | Anderson et al. | |
| 5,530,101 A | 6/1996 | Queen et al. | |
| 5,556,752 A | 9/1996 | Lockhart et al. | |
| 5,565,332 A | 10/1996 | Hoogenboom et al. | |
| 5,578,832 A | 11/1996 | Trulson et al. | |
| 5,585,089 A | 12/1996 | Queen et al. | |
| 5,593,839 A | 1/1997 | Hubbell et al. | |
| 5,599,695 A | 2/1997 | Pease et al. | |
| 5,631,734 A | 5/1997 | Stern et al. | |
| 5,693,762 A | 12/1997 | Queen et al. | |
| 5,721,367 A | 2/1998 | Kay et al. | |
| 5,837,243 A | 11/1998 | Deo et al. | |
| 5,837,832 A | 11/1998 | Chee et al. | |
| 5,843,708 A | 12/1998 | Hardman et al. | |
| 5,859,205 A | 1/1999 | Adair et al. | |
| 5,939,598 A | 8/1999 | Kucherlapati et al. | |
| 6,113,898 A | 9/2000 | Anderson et al. | |
| 6,130,364 A | 10/2000 | Jakobovits et al. | |
| 6,180,377 B1 | 1/2001 | Morgan et al. | |
| 6,423,511 B1 | 7/2002 | Nakamura et al. | |
| 6,436,665 B1 | 8/2002 | Kuimelis | |
| 6,458,592 B1 | 10/2002 | Jakobovits et al. | |
| 9,671,405 B2 | 6/2017 | Giannakakou et al. | |
| 2002/0165381 A1 | 11/2002 | Ahrens-Fath et al. | |
| 2007/0248535 A1* | 10/2007 | Buttyan ............ | C07K 16/3069 424/1.49 |
| 2015/0233927 A1* | 8/2015 | Giannakakou ... | G01N 33/57434 514/449 |

FOREIGN PATENT DOCUMENTS

| | | |
|---|---|---|
| CA | 2721506 A1 | 10/2009 |
| EP | 0721016 A2 | 7/1996 |
| EP | 0728520 A1 | 8/1996 |
| EP | 0785280 A2 | 7/1997 |
| EP | 0799897 A1 | 10/1997 |
| EP | 2300041 A2 | 3/2011 |
| WO | WO-86/01533 | 3/1986 |
| WO | WO-95/22058 A1 | 8/1995 |

(Continued)

OTHER PUBLICATIONS

Ceraline et al. (2004) Int. J. Cancer 108: 152-157.*
Abrahamsson, P.A., Neuroendocrine Cells in Tumor Growth of the Prostate, Endocrine-Related Cancer, 6:503-19 (1999).
Advisory Action dated Apr. 9, 2015 by the US Patent and Trademark Office for U.S. Appl. No. 12/988,299, filed Jan. 18, 2011 and published as US 2011/0110926 on May 12, 2011 (Inventor—Luo et al.; Applicant—The Johns Hopkins University) (5 pages).

(Continued)

*Primary Examiner* — Michael D Pak
(74) *Attorney, Agent, or Firm* — Ballard Spahr LLP

(57) ABSTRACT

The invention features diagnostic and therapeutic methods and compositions featuring androgen receptor variant proteins and nucleic acid molecules whose expression is increased in androgen related diseases or disorders.

25 Claims, 27 Drawing Sheets

Specification includes a Sequence Listing.

(56) References Cited

FOREIGN PATENT DOCUMENTS

| WO | WO-97/02357 A1 | 1/1997 |
|----|----|----|
| WO | WO-97/27317 | 7/1997 |
| WO | WO-97/29212 A1 | 8/1997 |
| WO | WO-02/17904 | 3/2002 |
| WO | WO-2009/128936 A2 | 10/2009 |
| WO | WO-2012006241 | 1/2012 |
| WO | WO-2014/018926 A1 | 1/2014 |
| WO | WO-2015/023710 A1 | 2/2015 |
| WO | WO-2015/179404 A1 | 11/2015 |
| WO | WO-2016/033114 A1 | 3/2016 |

OTHER PUBLICATIONS

Advisory Action dated Apr. 28, 2015 by the US Patent and Trademark Office for U.S. Appl. No. 12/988,299, filed Jan. 18, 2011 and published as US 2011/0110926 on May 12, 2011 (Inventor—Luo et al.; Applicant—The Johns Hopkins University) (3 pages).
Advisory Action dated Dec. 19, 2013 by the US Patent and Trademark Office for U.S. Appl. No. 12/988,299, filed Jan. 18, 2011 and published as US 2011/0110926 on May 12, 2011 (Inventor—Luo et al.; Applicant—The Johns Hopkins University) (3 pages).
Agoulnik, I.U. and N.L. Weigel, Androgen Receptor Action in Hormone-Dependent and Recurrent Prostate Cancer, J Cell BioChem, 99:362-72 (2006).
Armstrong, A.J. and M.A. Carducci, New Drugs in Prostate Cancer, Curr Opin Urol, 16:138-45 (2006).
Barltrop, J.A. et al., 5-(3-Carboxymethoxyphenyl)-2-(4,5-Dimethylthiszolyl)-3-(4-Sulfophenyl)Tetrazolium, Inner salt (MTS) and Related Analogs of 3-(4,5-Dimethylthiazolyl)-2,5-Diphenyltetrazolium Bromide (MTT) Reducing to Purple Water-Soluble Formazans as Cell-Viability Indicators, Bioorg & Med Chem Lett, 1(11): 611-4 (1991).
Bendig, M.M., Humanization of Rodent Monoclonal Antibodies by CDR Grafting, Methods: A Companion Methods in Enzymology, 8:83-93 (1995).
Blömer, U. et al., Highly Efficient and Sustained Gene Transfer in Adult Neurons with a Lentivirus Vector, J Virology, 71(9): 6641-9 (1997).
Brown et al., Deletion of the Steroid-Binding Domain of the Human Androgen Receptor Gene in One Family with Complete Androgen Insensitivity Syndrome: Evidence for Further Genetic Heterogeneity in this Syndrome, Proc Natl Acad Sci USA, 85(21): 8151-5 (1988).
Butler, L.M. et al., Suppression of Androgen Receptor Signaling in Prostate Cancer Cells by an Inhibitory Receptor Variant, Mol Endocrinol, 20(5): 1009-24 (2006).
Carell, T. et al., A Novel Procedure for the Synthesis of Libraries containing Small Organic Molecules, Angew Chem Int Ed Engl, 33(20): 2059-61 (1994).
Carell, T. et al., A Solution-Phase Screening Procedure for the Isolation of Active Compounds from a Library of Molecules, Angew Chem Int Ed Engl, 33(20): 2061-4 (1994).
Casset, F. et al., A Peptide Mimetic of an Anti-CD4 Monoclonal Antibody by Rational Design, Biochem Biophys Res Commun, 307(1): 198-205 (2003).
Catalano, M.G. et al., Altered Expression of Androgen-Receptor Isoforms in Human Colon-Cancer Tissues, Intl J Cancer, 86(3): 325-30 (2000).
Cayouette, M. and C. Gravel, Adenovirus-Mediated Gene Transfer of Ciliary Neurotrophic Factor Can Prevent Photoreceptor Degeneration in the Retinal Degeneration (rd) Mouse, Human Gene Therapy, 8:423-30 (1997).
Chen, C.D. et al., Molecular Determinants of Resisteance to Antiandrogen Therapy, Nature Med, 10(1): 33-9 (2004).
Chen, Y. et al., Targeting the Androgen Receptor Pathway in Prostate Cancer, Curr Opin Pharm, 8: 440-8 (2008).
Chmelar, R. et al., Androgen Receptor Coregulators and Their Involvement in the Development and Progression of Prostate Cancer, Int J Cancer, 120: 719-33 (2006).
Cho, C.Y. et al., An Unnatural Biopolymer, Science, 261(5126): 13303-5 (1993).
Crouch, S.P.M., et al., The Use of ATP Bioluminescence as a Measure of Cell Proliferation and Cytotoxicity, J Immunol Meth, 160: 81-8 (1993).
Cull, M.G. et al., Screening for Receptor Ligands Using Large Libraries of Peptides Linked to the C Terminus of the lac Repressor, Proc Natl Acad Sci USA, 89: 1865-9 (1992).
Cwirla, S.E., et al., Peptides on Phage: A Vast Library of Peptides for Identifying Ligands, Proc Natl Acad Sci USA, 87: 6378-82 (1990).
Céraline, J. et al., Constitutive Activation of the Androgen Receptor by a Point Mutation in the Hinge Region: A New Mechanism for Androgen-Independent Growth in Prostate Cancer, Int J Cancer, 108:152-7 (2004).
Dehm, S.M. and D.J. Tindall, Androgen Receptor Structural and Functional Elements: Role and Regulation in Prostate Cancer, Mol Endocrinol, 21(12): 2855-63 (2007).
Dehm, S.M. et al., Splicing of a Novel Androgen Receptor Exon Generates a Constitutively Active Androgen Receptor that Mediates Prostate Cancer Therapy Resistance, Cancer Res, 68(13): 5469-77 (2008).
DeWitt, S.H. et al., "Diversomers:" An Approach to Nonpeptide, nonoligometric Chemical Diversity, Proc Natl Acad Sci USA, 90: 6909-13 (1993).
Dhanasekaran, S.M. et al., Delineation of Prognostic Biomarkers in Prostate Cancer, Nature, 412: 822-6 (2001).
Erb, E. et al., Recursive Deconvolution of Combinatorial Chemical Libraries, Proc Natl Acad Sci USA, 91: 11422-6 (1994).
European Search Report and Written Opinion completed on Jun. 6, 2016 by the European Patent Office for European Patent Application No. 16152616.5, which was filed on Apr. 16, 2009 and published as 3062106 on Aug. 31, 2016, 2011 (Inventor—Luo et al.; Applicant—The Johns Hopkins University) (9 pages).
Feigner, P.L. et al., Lipofection: A Highly Efficient, Lipid-Mediated DNA-Transfection Procedure, Proc Natl Acad Sci USA, 84: 7413-7 (1987).
Felici, F. et al., Selection of Antibody Ligands from a Large Library of Oligopeptides Expressed on a Multivalent Exposition Vector, J Mol Biol, 222: 301-10 (1991).
Final Office Action dated Nov. 21, 2014 by the US Patent and Trademark Office for U.S. Appl. No. 12/988,299, filed Jan. 18, 2011 and published as US 2011/0110926 on May 12, 2011 (Inventor—Luo et al.; Applicant—The Johns Hopkins University) (21 pages).
Final Office Action dated Sep. 12, 2013 by the US Patent and Trademark Office for U.S. Appl. No. 12/988,299, filed Jan. 18, 2011 and published as US 2011/0110926 on May 12, 2011 (Inventor—Luo et al.; Applicant—The Johns Hopkins University) (5 pages).
Fleming, M.T. et al., Post-Therapy Changes in PSA as an Outcome Measure in Prostate Cancer Clinical Trials, Nat Clin Pract Oncol, 3(12): 658-67 (2006).
Fodor, S.P.A. et al., Multiplexed Biochemical Assays with Bilogical Chips, Nature, 364: 555-6 (1993).
Ge, H. UPA, a Universal Protein Array System for Quantitative Detection of Protein-Protein, Protein-DNA, Protein-RNA and Prtein-Ligand Interactions, Neucleic Acids Reseach, 28(2): e3i-vii (2000).
Gelmann, E.P., Molecular Biology of the Androgen Receptor, J Clin Oncol, 20(13): 3001-15 (2002).
Gu, Y. et al., Hematopoietic Cell Regulation by Rac1 and Rac2 Guanosine Triphosphatases, Science, 302: 445-9 (2003).
Haapala K et al: Androgen receptor alterations in prostate cancer relapsed during a combined androgen blockade byorchiectomy and bicalutamide, Laboratory Investigation, Nature Publishing Group, The United States Andcanadian Academy of Pathology, Inc., vol. 81, No. 12, Dec. 2001, pp. 1647-1651.
Hara Takahito et al: Novel mutations of androgen receptor: a possible mechanism of bicalutamide withdrawal syndrome, Cancer Research, American Association for Cancer Research, vol. 63, No. 1, Jan. 2003, pp. 149-153.

(56) References Cited

OTHER PUBLICATIONS

Heinlein, C.A. and Chawnshang Chang, Androgen Receptor in Prostate Cancer, Endocr Rev, 25(2): 276-308 (2004).
Heller, R.A. et al., Discovery and Analysis of Inflammatory Disease-Related Genes Using cDNA Microarrays, Proc Natl Acad Sci USA, 94:2150-5 (1997).
Hirata, S. et al., Isoform/Variant mRNAs for Sex Steroid Hormone Receptors in Humans, Trends Endocrin Met, 14(3): 124-9 (2003).
Hu, R. et al., Ligand-Independent Androgen Receptor Variants Derived from Spicing of Cryptic Exons Signify Hormone-Refractory Protstate Cancer, Cancer Res, 69(1): 16-22 (2009).
Huggins, M.D., C. and C.V. Hodges, M.D., Studies on Prostatic Cancer: I. The Effect of Castraction, of Estrogen and of Androgen Injection on Serum Phosphates in Metastatic Carcinoma of the Prostate, Cancer Res, 1: 293-7 (1941).
International Preliminary Report on Patentability dated Oct. 19, 2010 by the International Searching Authority for International Patent Application No. PCT/US2009/002392, which was filed on Apr. 6, 2009 and published as WO 2009/128936 on Oct. 22, 2009 (Inventor—Luo et al.; Applicant—The Johns Hopkins University) (8 pages).
International Search Report and Written Opinion dated Dec. 4, 2009 by the International Searching Authority for International Patent Application No. PCT/US2009/002392, which was filed on Apr. 6, 2009 and published as WO 2009/128936 on Oct. 22, 2009 (Inventor—Luo et al.; Applicant—The Johns Hopkins University) (11 pages).
Issue Notification dated Sep. 29, 2015 by the US Patent and Trademark Office for U.S. Appl. No. 12/988,299, filed Jan. 18, 2011 and published as US 2011/0110926 on May 12, 2011 (Inventor—Luo et al.; Applicant—The Johns Hopkins University) (1 pages).
Jagla, M. et al., A Splicing Variant of the Androgen Receptor Detected in a Metastatic Prostate Cancer Exhibits Exclusively Cytoplasmic Actions, Endocrin, 148(9): 4334-4343 (2007).
Jocelyn Ceraline et al: Constitutive activation of the androgen receptor by a point mutation in the hinge region: A new mechanism for androgen-independent growth in prostate cancer, International Journal of Cancer, vol. 108, No. 1, Jan. 2004, pp. 152-157.
Johnson, L.G., Gene Therapy for Cystic Fibrosis, Chest, 107: 77S-83S (1995).
Kaarbo, Mari et al., Androgen Signaling and Its Interactions with Other Signaling Pathways in Prostate Cancer, BioEssays, 29: 1227-38 (2007).
Kittler, R. et al., An Endoribonuclease-Prepared siRNA Screen in Human Cells Identifies Genes Essential for Cell Division, Nature, 432: 1036-40 (2004).
Ko et al., Androgen Receptor Down-Regulation in Prostate Cancer with Phosphorodiamidate Morpholino Antisense Oligomers, J Urol, 172(3): 1140-4 (2004).
Lam, K.S., et al., A New Type of Synthetic Peptide Library for Identifying Ligand-Binding Activity, Nature, 354:82-4 (1991).
Lapouge Gaelle et al: Specific properties of a C-terminal truncated androgen receptor detected in hormone refractory prostate cancer, Advances in Experimental Medicine and Biology, vol. 617, Jan. 2008 pp. 529-534.
Libertini, S.J. et al., Evidence for Calpain-Mediated Androgen Receptor Cleavage as a Mechanism for Androgen Independence, Cancer Res, 67(19): 9001-5 (2007).
Linja, M.J. and Tapio Visakorpi, Alterations of Androgen Receptor in Prostate Cancer, J Steriod Biochem, 92: 255-64 (2004).
Lockhart, D.J. et al., Expression Monitoring by Hybridization to High-Density Oligonucleotide Arrays, Nat Biotechnol, 14: 1675-80 (1996).
Luo, J. et al., Human Prostate Cancer and Benign Prostatic Hyperplasia: Molecular Dissection by Gene Expression Profiling, Cancer Res, 61: 4683-8 (2001).
MacBeath, G. and S.L. Schreiber, Printing Proteins as Microarrays for High-Throughput Function Determination, Science, 289: 1760-3 (2000).
MacCallum, R.M. et al., Antibody-Antigen Interactions: Contact Analysis and Binding Site Topography, J Mol Biol, 262(5): 732-45 (1996).
Maroni, M.D., P.D. and E.D. Crawford, M.D., The Benefits of Early Androgen Blockade, Best Pract Res Cl En, 22(2): 317-29 (2008).
Miller, A.D. and G.J. Rosman, Improved Retroviral Vectors for Gene Transfer and Expression, Biotechniques, 7(9): 980-990 (1989).
Miller, A.D., Retrovirus Packaging Cells, Human Gene Therapy, 1:5-14 (1990).
Miyamoto, A. et al., Increased Proliferation of B Cells and Auto-Immunity in Mice Lacking Protein Kinase Cd, Nature, 416: 865-9 (2002).
Miyoshi, H. et al., Stable and Efficient Gene Transfer into the Retina Using an HIV-Based Lentiviral Vector, Proc Natl Acad Sci USA, 94: 10319-23 (1997).
Montgomery, R.B. et al., Maintenance of Intratumoral Androgens in Metastatic Prostate Cancer: A Mechanism for Castration-Resistant Tumor Growth, Cancer Res, 68(11): 4447-54 (2008).
Mostaghel, E.A. and P.S. Nelson, Intracrine Androgen Metabolism in Prostate Cancer Progression: Mechanisms of Castration Resistance and Therapeutic Implications, Best Pract Res Cl En, 22(2): 243-58 (2008).
Non-Final Office Action dated Jun. 5, 2014 by the US Patent and Trademark Office for U.S. Appl. No. 12/988,299, filed Jan. 18, 2011 and published as US 2011/0110926 on May 12, 2011 (Inventor—Luo et al.; Applicant—The Johns Hopkins University) (9 pages).
Non-Final Office Action dated Jun. 20, 2012 by the US Patent and Trademark Office for U.S. Appl. No. 12/988,299, filed Jan. 18, 2011 and published as US 2011/0110926 on May 12, 2011 (Inventor—Luo et al.; Applicant—The Johns Hopkins University) (5 pages).
Notice of Allowance dated Jun. 26, 2015 by the US Patent and Trademark Office for U.S. Appl. No. 12/988,299, filed Jan. 18, 2011 and published as US 2011/0110926 on May 12, 2011 (Inventor—Luo et al.; Applicant—The Johns Hopkins University) (7 pages).
Ono, T. et al., Plasmid DNAs Directly Injected into Mouse Brain with Lipofectin can be Incorporated and Expressed by Brain Cells, Neurosci Lett, 117:259-63 (1990).
Otto, D. and K. Unsicker, Basic FGF Reverses Chemical and Morphological Deficits in the Nigrostriatal System of MPTP-Treated Mice, J Neurosci, 10(6): 1912-21 (1990).
Pan, Q. et al., Quantitative Microarray Profiling Provides Evidence Against Widespread Coupling of Alternative Splicing with Nonsense-Mediated mRNA Decay to Control Gene Expression, Genes & Dev, 20:153-8 (2006).
Paul, W.E., Fundamental Immunology, 3rd Edition, New York: Raven Press, pp. 292-295 (1993).
Paull, K.D. et al., The Synthesis of XTT: A New Tetrazolium Reagent that is Bioreducible to a Water-Soluble Formazan, J Heterocyclic Chem, 25: 911-4 (1988).
Petty, R.D., Comparison of MTT and ATP-Based Assays for the Measurement of Viable Cell Number, J Biolumin Chemilumin, 10:29-34 (1995).
Preliminary Amendment filed on Oct. 15, 2010 with the US Patent and Trademark Office for U.S. Appl. No. 12/988,299, filed Jan. 18, 2011 and published as US 2011/0110926 on May 12, 2011 (Inventor—Luo et al.; Applicant—The Johns Hopkins University) (11 pages).
Response After Final Office Action filed on Mar. 3, 2015 with the US Patent and Trademark Office for U.S. Appl. No. 12/988,299, filed Jan. 18, 2011 and published as US 2011/0110926 on May 12, 2011 (Inventor—Luo et al.; Applicant—The Johns Hopkins University) (8 pages).
Response to Advisory Action filed on Apr. 19, 2015 with the US Patent and Trademark Office for U.S. Appl. No. 12/988,299, filed Jan. 18, 2011 and published as US 2011/0110926 on May 12, 2011 (Inventor—Luo et al.; Applicant—The Johns Hopkins University) (6 pages).
Response to Advisory Action filed on May 14, 2015 with the US Patent and Trademark Office for U.S. Appl. No. 12/988,299, filed Jan. 18, 2011 and published as US 2011/0110926 on May 12, 2011 (Inventor—Luo et al.; Applicant—The Johns Hopkins University) (6 pages).
Response to Final Office Action filed on Dec. 12, 2013 with the US Patent and Trademark Office for U.S. Appl. No. 12/988,299, filed

(56) References Cited

OTHER PUBLICATIONS

Jan. 18, 2011 and published as US 2011/0110926 on May 12, 2011 (Inventor—Luo et al.; Applicant—The Johns Hopkins University) (9 pages).
Response to Non-Final Office Action filed on Aug. 7, 2014 with the US Patent and Trademark Office for U.S. Appl. No. 12/988,299, filed Jan. 18, 2011 and published as US 2011/0110926 on May 12, 2011 (Inventor—Luo et al.; Applicant—The Johns Hopkins University) (10 pages).
Response to Non-Final Office Action filed on Sep. 20, 2012 with the US Patent and Trademark Office for U.S. Appl. No. 12/988,299, filed Jan. 18, 2011 and published as US 2011/0110926 on May 12, 2011 (Inventor—Luo et al.; Applicant—The Johns Hopkins University) (12 pages).
Response to Restriction Requirement filed on Mar. 29, 2012 with the US Patent and Trademark Office for U.S. Appl. No. 12/988,299, filed Jan. 18, 2011 and published as US 2011/0110926 on May 12, 2011 (Inventor—Luo et al.; Applicant—The Johns Hopkins University) (4 pages).
Restriction Requirement dated Feb. 29, 2012 by the US Patent and Trademark Office for U.S. Appl. No. 12/988,299, filed Jan. 18, 2011 and published as US 2011/0110926 on May 12, 2011 (Inventor—Luo et al.; Applicant—The Johns Hopkins University) (8 pages).
Rosenberg, S.A. et al., Gene Transfer into Humans—Immunotherapy of Patients with Advanced Melanoma, Using Tumor-Infiltrating Lymphocytes Modified by Retroviral Gene Transduction, New Engl J Med, 323(9): 570-8 (1990).
Ruefli-Brasse, A.A. et al., Regulation of NF-κB-Dependent Lymphocyte Activation and Development by Paracaspase, Science, 302: 1581-4 (2003).
Saramäki, O.R. et al., Genetic Aberrations in Prostate Cancer by Microarray Analysis, Int J Cancer, 119: 1322-9 (2006).
Schena, M. et al., Parallel Human Genome Analysis: Microarray-Based Expression Monitoring of 1000 Genes, Proc Natl Acad Sci USA, 93: 10614-9 (1996).
Scher, H.I. and C.L. Sawyers, Biology of Progressive, Castration-Resistant Prostate Cancer: Directed Therapies Targeting the Androgen-Receptor Signaling Axis, J Clin Oncol, 23(32): 8253-61 (2005).
Shang, Y. et al., Formation of the Androgen Receptor Transcription Complex, Mol Cell, 9: 601-10 (2002).
Sharp, D., Conference: Gene Therapy, The Lancet, 337: 1277-8 (1991).
Skolnick, J. and J.S. Fetrow, From Genes to Protein Structure and Function: Novel Applications of Computational Approaches in the Genomic Era, Trends Biotechnol, 18(1): 34-9 (2000).
Small, E.J. and C.J. Ryan, The Case for Secondary Hormonal Therapies in the Chemotherapy Age, J Urol, 176: S66-71 (2006).
Straubinger, R.M. and D. Papahadjopoulos, Liposomes as Carriers for Intracellular Delivery of Nucleic Acids, Method Enzymol, 101: 512-27 (1983).
Supplementary European Search Report and Written Opinion completed on Jul. 26, 2011 by the European Patent Office for European Patent Application No. 09733012.0, which was filed on Apr. 16, 2009 and published as 2300041 on Mar. 30, 2011 (Inventor—Luo et al.; Applicant—The Johns Hopkins University) (10 pages).
Suzuki, H. et al., Interfocal Heterogeneity of PTEN/MMAC1 Gene Alterations in Multiple Metastatic Prostate Cancer Tissues, Cancer Res, 58: 204-9 (1998).
Tepper, C.G. et al., Characterization of a Novel Androgen Receptor Mutation in a Relapsed CWR22 Prostate Cancer Xenograft and Cell Line, Cancer Res, 62: 6606-14 (2002).
Tolstoshev, P. and W.F. Anderson, Gene Expression Using Retroviral Vectors, Curr Opin Biotech, 1:55-61 (1990).
Tyagi, S. and F.R. Kramer, Molecular Beacons: Probes that Fluoresce Upon Hybridization, Nat Biotechnol, 14: 303-8 (1996).
Vajdos, F.F. et al., Comprehensive Functional Maps of the Antigen-Binding Site of an Anti-ErbB2 Antibody Obtained with Shotgun Scanning Mutagenesis, J Mol Biol, 320(2): 415-28 (2002).

W D Tilley et al: Mutations in the Androgen Receptor Gene Are Associated with Progression of Human Prostate Cancer to Androgen Independence , Clin Cancer Res, vol. 2, Jan. 1996, pp. 277-285.
Wahl, R.L. et al., Improved Radioimaging and Tumor Localization with Monoclonal F(ab')2, J Nucl Med, 24: 316-25 (1983).
Wu, C.H. et al., Targeting Genes: Delivery and Persistent Expression of a Foreign Gene Driven by Mammalian Regulatory Elements in Vivo, J Biol Chem, 264(29): 16985-7 (1989).
Wu, G.Y. and C.H. Wu, Receptor-Mediated Gene Delivery and Expression in Vivo, J Biol Chem, 263(29): 14621-4 (1988).
Wu, H. et al., Humanization of a murine monoclonal antibody by simultaneous optimization of framework and CDR residues, J Mol Biol, 294(1): 151-62 (1999).
Zhou, Z. et al., A Ligand-Dependent Bipartite Nuclear Targeting Signal in the Human Androgen Receptor, J Biol Chem, 269(18): 13115-23 (1994).
Zhu, H. et al., Analysis of Yeast Protein Kinases Using Protein Chips, Nat Genet, 26: 283-9 (2000).
Zhu, X. et al., Identification of an Exon 3 Deletion Splice Variant Androgen Receptor mRNA in Human Breast Cancer, Intl J Cancer, 72(4): 574-80 (1997).
Zuckermann, R.N. et al., Discovery of Nanomolar Ligands for 7-Transmembrane G-Protein-Coupled Receptors from a Diverse N-(Substituted)glycine Peptoid Library, J Med Chem, 37: 2678-85 (1994).
Anderson, W.F., Prospects for Human Gene Therapy, Science, 226(4673):401-9 (1984).
Balic et al., Androgen Receptor Length Polymorphism Associated with Prostate Cancer Risk in Hispanic Men, J Urol, 168(5): 2245-8 (2002).
Brigham, K.L. et al., In Vivo Transfection of Murine Lungs with a Functioning Prokaryotic Gene Using a Liposome Vehicle, Am J Med Sci, 298(4): 278-81 (1989).
Brinkmann, A.O. et al., Mechanisms of Androgen Receptor Activation and Function, J Steriod Biochem Mol Biol, 69(1-06): 307-13 (1999).
Cordon-Cardo, C., Androgen Receptor Level in the Prostatectomy Specimen Predicts Time to Disease Progression Post Androgen Suppression Therapy, J Clin Oncol, 25(18S): 5065 (2007).
Cornetta, K. et al., Gene Transfer into Primates and Prospects for Gene Therapy in Humans, Prog Nucleic Acid Res Mol Biol, 36: 311-22 (1989).
Cory, A.H. et al., Use of an Aqueous Soluble Tetrazolium/Formazan Assay for Cell Growth Assays in Culture, Cancer Commun, 3(7): 207-12 (1991).
Cree, A.I. et al., Methotrexate Chemosensitivity by ATP Luminescence in Human Leukemia Cell Lines and in Breast Cancer Primary Cultures: Comparison of the TCA-100 Assay with a Clonogenic Assay, Anticancer Drugs, 6(3): 398-404 (1995).
Devlin, J.J. et al., Random Peptide Libraries: A Source of Specific Protein Binding Molecules, Science, 249(4967): 404-6 (1990).
Friedmann, T., Progress Toward Human Gene Therapy, Science, 244(4910) 1275-81 (1989).
Gallop, M.A. et al., Applications of Combinatorial Technologies to Drug Discovery. 1. Background and Peptide Combinatorial Libraries, J Med Chem, 37(9): 1233-51 (1994).
Houghten, R.A. et al., The Use of Synthetic Peptide Combinatorial Libraries for the Identification of Bioactive Peptides, Biotechniques, 13(3): 412-21 (1992).
Jenster, G. et al., Domains of the Human Androgen Receptor Involved in Steroid Binding Transcriptional Activation and Subcellular Localization, Mol Endocrin, 5(10): 1396-1404 (1991).
Kangas, L. et al., Bioluminescence of Cellular ATP: A New Method for Evaluating Cytotoxic Agents in Vitro, Med Biol, 62(6): 338-43 (1984).
Kido, M. et al., Use of a Retroviral Vector with an Internal Opsin Promoter to Direct Gene Expression to Retinal Photorecptor Cells, Curr Eye Res, 15(8): 833-44 (1996).
Lam, K.S., Application of Combinatorial Library Methods in Cancer Research and Drug Discovery, Anticancer Drug Des, 12(3): 145-67 (1997).

(56) References Cited

OTHER PUBLICATIONS

Le Gal La Salle, G. et al., An Adenovirus Vector for Gene Transfer into Neurons and Glia in the Brain, Science, 259(5097: 988-90 (1993).
Moen, R.C., Directions in Gene Therapy, Blood Cells, 17(2): 407-16 (1991).
Naldini, L. et al., In Vivo Gene Delivery and Stable Transduction of Nondividing Cells by a Lentiviral Vector, Science, 272(5259): 263-7 (1996).
Otto, D. et al., Basic Fibroblast Growth Factor and Nerve Growth Factor Administered in Gel Foam Rescue Medial Septal Neurons after Fimbria Fornix Transection, J Neurosci Res, 22(1): 83-91 (1989).
Quigley, C.A. et al., Complete Androgen Insensitiveity due to Deletion of Exon C of the Androgen Receptor Gene Highlights the Functional Importance of the Second Zinc Finger of the Androgen Receptor in Vivo, Mol Endocrinol, 6(7): 1103-12 (1992).
Scott, J.K. and G.P. Smith, Searching for Peptide Ligands with an Epitope Library, Science, 249(4967): 386-90 (1990).
Wolff, J.A. et al., Direct Gene Transfer into Mouse Muscle in Vivo, Science, 247(4949 pt. 1): 1465-8 (1990).
U.S. Appl. No. 12/988,299 (U.S. Pat. No. 9,146,238), filed Oct. 15, 2010 (Sep. 29, 2015), Luo et al. (The Johns Hopkins University).
CA, 2721506, Oct. 15, 2010, Luo et al. (The Johns Hopkins University).
DE, 602009035993.2 (2300041), Apr. 16, 2008 (Jan. 27, 2016), Luo et al. (The Johns Hopkins University).
EP, 09733012.0 (2300041), Nov. 15, 2010 (Mar. 30, 2011), Luo et al. (The Johns Hopkins University).
EP, 16152616.5 (3062106), Apr. 16, 2009 (Aug. 31, 2016), Luo et al. (The Johns Hopkins University).
ES, 09733012.0 (2300041), Apr. 16, 2009 (Jan. 27, 2016), Luo et al. (The Johns Hopkins University).
FR, 09733012.0 (2300041), Apr. 16, 2009 (Jan. 27, 2016), Luo et al. (The Johns Hopkins University).
GB, 09733012.0 (2300041), Apr. 16, 2009 (Jan. 27, 2016), Luo et al. (The Johns Hopkins University).
IT, 502016000040894 (2300041), Apr. 16, 2009 (Jan. 27, 2016), Luo et al. (The Johns Hopkins University).
PCT, PCT/US2009/002392 (WO 2009/128936), Apr. 16, 2009 (Oct. 22, 2009), Luo et al. (The Johns Hopkins University).
Anders et al., HTSeq—A Python framework to work with high-throughput sequencing data, Bioinformatics (doi: 10.1093/bioinformatics/btu638) (2014).
Andersen et al., Regression of castrate-recurrent prostate cancer by a small-molecule inhibitor of the amino-terminus domain of the androgen receptor. Cancer Cell, 17:535-46 (2010).
Antonarakis, E.S. et al., AR-V7 and resistance to enzalutamide and abiraterone in prostate cancer. N Engl J Med 371:1028-38 (2014).
Armstrong, A.I. et al., Biomarkers in the management and treatment of men with metastatic castration-resistant prostate cancer. Eur Urol 61:549-59 (2012).
Arora, V.K. et al., Glucocorticoid receptor confers resistance to antiandrogens by bypassing androgen receptor blockade. Cell, 155(6):1309-22 (2013).
Aryee et al., DNA methylation alterations exhibit intraindividual stability and interindividual heterogeneity in prostate cancer metastases. Sci Transl Med, 5(169):169ra10 (2013).
Attard et al., Phase I clinical trial of a selective inhibitor of CYP17, abiraterone acetate, confirms that castration-resistant prostate cancer commonly remains hormone driven. J Clin Oncol, 26:4563-71 (2008).
Balbas et al., Overcoming mutation-based resistance to antiandrogens with rational drug design. eLife, 2:e00499 (2013).
Basch, E. et al, Systemic therapy in men with metastatic castration-resistant prostate cancer: American Society of Clinical Oncology and Cancer Care Ontario clinical practice guideline. J Clin Oncol, 32:3436-48 (2014).
Carver et al., Reciprocal feedback regulation of PI3K and androgen receptor signaling in PTEN-deficient prostate cancer. Cancer Cell, 19:575-86 (2013).
Chang, K. H. et al., A Gain-of-Function Mutation in DHT Synthesis in Castration-Resistant Prostate Cancer. Cell, 154(5):1074-84 (2013).
Chee et al., Accessing Genetic Information with High-Density DNA Arrays. Science, 274(5287):610-4 (1996).
Darshan et al., Taxane-induced blockade to nuclear accumulation of the androgen receptor predicts clinical responses in metastatic prostate cancer. Cancer Res, 71: 6019-29 (2011).
De Bono, J.S. et al., Abiraterone and increased survival in metastatic prostate cancer. N Engl J Med, 364:1995-2005 (2011).
De Bono, J.S. et al: Prednisone plus cabazitaxel or mitoxantrone for metastatic castration-resistant prostate cancer progressing after docetaxel treatment: a randomised open-label trial. Lancet, 376:1147-54 (2010).
De Leeuw et al., Novel actions of next-generation taxanes benefit advanced stages of prostate cancer. Clin Cancer Res, 21:795-807 (2015).
Dehm, S.M. et al., Splicing of a novel androgen receptor exon generates a constitutively active androgen receptor that mediates prostate cancer therapy resistance. Cancer Res, 68: 5469-77 (2008).
Efstathiou, E. et al., MDV3100 effects on androgen receptor (AR) signaling and bone marrow testosterone concentration modulation: A preliminary report. ASCO Meeting Abstracts, 29:4501 (2011).
Efstathiou, E. et al., Effects of abiraterone acetate on androgen signaling in castrate-resistant prostate cancer in bone. J Clin Oncol, 30(6):637-43 (2012).
Eisenhauer, E.A. et al., New response evaluation criteria in solid tumours: revised RECIST guideline (version 1.1). Eur J Cancer, 45:228-247 (2009).
Gan, L. et al., Inhibition of the androgen receptor as a novel mechanism of taxol chemotherapy in prostate cancer. Cancer Res, 69:8386-94 (2009).
Guo, Z. et al. A Novel Androgen Receptor Splice Variant Is Up-regulated during Prostate Cancer Progression and Promotes Androgen Depletion-Resistant Growth. Cancer Res, 69:2305-13 (2009).
Hacia et al., Detection of heterozygous mutations in BRCA1 using high density oligonucleotide arrays and two-colour fluorescence analysis. Nat Genet, 14(4):441 (1996).
Hornberg, E. et al., Expression of Androgen Receptor Splice Variants in Prostate Cancer Bone Metastases is Associated with Castration-Resistance and Short Survival. PLoS ONE, 6:e19059 (2011).
Hu et al., Ligand-independent androgen receptor variants derived from splicing of cryptic exons signify hormone-refractory prostate cancer. Cancer Res, 69:16-22 (2009).
Hu, R. et al., A snapshot of the expression signature of androgen receptor splicing variants and their distinctive transcriptional activities. The Prostate, 71:1656-67 (2011).
Hu, R. et al., Distinct transcriptional programs mediated by the ligand-dependent full-length androgen receptor and its splice variants in castration-resistant prostate cancer. Cancer Res, 72:3457-62 (2012).
Itakura et al., Synthesis and Use of Synthetic Oligonucleotides. Ann Rev Biochem, 53:323-56 (1984).
Joseph, J.D. et al., a clinically relevant androgen receptor mutation confers resistance to second-generation antiandrogens enzalutamide and ARN-509. Cancer Discov, 3(9):1020-9 (2013).
Kantoff et al., Sipuleucel-T immunotherapy for castration-resistant prostate cancer. N Engl J Med, 363: 411-22 (2010).
Karantanos, T. et al., Understanding the mechanisms of androgen deprivation resistance in prostate cancer at the molecular level. Eur Urol, epub ahead of print (doi: 10.1016/j.eururo.2014.09.049) (2014).
Kirby, B.J. et al., Functional characterization of circulating tumor cells with a prostate-cancer-specific microfluidic device. PLoS One 7: e35976 (2012).
Kozal et al., Extensive polymorphisms observed in HIV-1 clade B protease gene using high-density oligonucleotide arrays. Nat Med, 2(7):753-9 (1996).
Li, Y. et al., Androgen receptor splice variants mediate enzalutamide resistance in castration-resistant prostate cancer cell lines. Cancer Res, 73: 483-9 (2013).

(56) References Cited

OTHER PUBLICATIONS

Liu, W. et al., Copy number analysis indicates monoclonal origin of lethal metastatic prostate cancer. Nat Med, 15:559-65 (2009).
Lockhart et al., Expression monitoring by hybridization to high-density oligonucleotide arrays. Nat Biotechnol, 14(13):1675-80 (1996).
Longo, D.L., New therapies for castration-resistant prostate cancer. N Engl J Med, 363:479-81 (2010).
Mitsiades, N. et al., Distinct patterns of dysregulated expression of enzymes involved in androgen synthesis and metabolism in metastatic prostate cancer tumors. Cancer Res, 72:6142-52 (2012).
Mostaghel, E.A. et al., Resistance to CYP17A1 inhibition with abiraterone in castration-resistant prostate cancer: induction of steroidogenesis and androgen receptor splice variants. Clin Cancer Res, 17:5913-25 (2011).
Nadiminty, N. et al., NF-kappaB2/p52 induces resistance to enzalutamide in prostate cancer: role of androgen receptor and its variants. Mol cancer Ther, 12:1629-37 (2013).
Narang et al., Chemical Synthesis of Deoxyoligonucleotides by the Modified Triester Method. Methods Enzymol, 65(1):610-20 (1980).
Norris, J.D. et al., The homeodomain protein HOXB13 regulates the cellular response to androgens. Mol Cell, 36(3):405-16 (2009).
O'Donnell, A. et al., Hormonal impact of the 17alpha-hydroxylase/C(17,20)-lyase inhibitor abiraterone acetate (CB7630) in patients with prostate cancer. Br J Cancer, 90(2):2317-25 (2004).
Parker, C. et al, Alpha emitter radium-223 and survival m metastatic prostate cancer. N Engl J Med, 369: 213-23 (2013).
Plymate, S.R. et al., Taxane resistance in prostate cancer mediated by AR-Independent GATA2 regustion of IGF2. Cancer Cell, 27:158-9 (2015).
Ravindranathan, P. et al., Peptidomimetic targeting of critical androgen receptor-coregulator interactions in prostate cancer. Nat Commun, 4:1923 (2013).
Roberts et al., RNA-peptide fusions for the in vitro selection of peptides and proteins. Proc Natl Acad Sci USA, 94(23):12297-302 (1997).
Robinson et al., Integrative genomics viewer. Nat Biotechnol, 29:24-6 (2011).
Ryan, C. J. et al., Abiraterone in Metastatic Prostate Cancer without Previous Chemotherapy. N Engl J Med, 368:138-48 (2013).
Ryan, C. J. et al., Androgen Receptor Rediscovered: The New Biology and Targeting the Androgen Receptor Therapeutically. J Clin Oncol, 29(27):3651-3658 (2011).
Sadar, D. Small Molecule Inhibitors Targeting the "Achilles' Heel" of Androgen Receptor Activity. Cancer Res, 71:1208-13 (2011).
Sahu, B. et al., FoxA1 Specifies Unique Androgen and Glucocorticoid Receptor Binding Events in Prostate Cancer Cells.Cancer Res, 73:1570-80 (2013).
Scher, H.I. et al., Increased survival with enzalutamide in prostate cancer after chemotherapy. N Engl J Med, 367:1187-97 (2012).
Scher, H.I. et al., Design and end points of clinical trials for patients with progressive prostate cancer and castrate levels of testosterone: recommendations of the Prostate Cancer Clinical Trials Working Group. J Clin Oncol, 26: 1148-59 (2008).
Scher, H.I. et al., Antitumour activity of MDV3100 in castration-resistant prostate cancer: a phase 1-2 study. Lancet, 375:1437-46 (2010).
Seruga, B. et al., Drug resistance in metastatic castration-resistant prostate cancer. Nat Rev Clin Oncol, 8:12-23 (2011).
Steplewski et al., Effects of Restraint Stress on Inoculated Tumor Growth and Immune Response in Rats. Cancer Res, 45: 5128-33 (1985).
Subramanan, A. et al., Gene set enrichment analysis: A knowledge-based approach for interpreting genome-wide expression profiles. Proc Natl Acad Sci USA, 102:15545-50 (2005).
Tannock, I.F. et al., Docetaxel plus prednisone or mitoxantrone plus prednisone for advanced prostate cancer. N Engl J Med, 351 (15):1502-12 (2004).

Thadani-Mulero et al., Androgen receptor on the move: boarding the microtubule expressway to the nucleus. Cancer Res, 72:4611-5 (2012).
Thadani-Mulero et al., Androgen receptor splice variants determine taxane sensitivity in prostate cancer. Cancer Res, 74:2270-82 (2014).
Therasse, P.et al., New Guidelines to Evaluate the Response to Treatment in Solid Tumors. J Natl Cancer Inst, 92:205-16 (2000).
Tran, C. et al., Development of a Second-Generation Antiandrogen for Treatment of Advanced Prostate Cancer. Science, 324:787-90 (2009).
Van Soest, R.J. et al., Targeting the androgen receptor confers in vivo cross-resistance between enzalutamide and docetaxel, but not cabazitaxel, in castration-resistant prostate cancer. Eur. Urol.; epub ahead of print (10.1016/j.euro.2014.11.033) (2014).
Verhoeyen et al., Engineering of Antibodies. BioEssays. 8 (2):74-8 (1988).
Watson, P.A. et al., Constitutively active androgen receptor splice variants expressed in castration-resistant prostate cancer require full-length androgen receptor. Proc Natl Acad Sci USA, 107(39):16759-65 (2010).
Yu, Y. et al., Expression and Function of the Progesterone Receptor in Human Prostate Stroma Provide Novel Insights to Cell Proliferation Control. J Clin Endocrinol Metab, 98: 2887-96 (2013).
Yu et al., Rapid Induction of Androgen Receptor Splice Variants by Androgen Deprivation in Prostate Cancer. Clin Cancer Res. 20(6): 1590-1600 (2014).
Zhang, X. et al., Androgen Receptor Variants Occur Frequently in Castration Resistant Prostate Cancer Metastases. PLoS ONE, 6(11): e27970 (2011).
Zhu et al., Tubulin-targeting chemotherapy 1mpairs androgen receptor activity in prostate cancer. Cancer Res, 70: 7992-8002 (2010).
International Search Report and Written Opinion dated Jan. 12, 2016 by the International Searching Authority for International Application No. PCT/US2015/046806, which was filed on Aug. 25, 2015 and published as WO/2016/033114 on Mar. 3, 2016 (Applicant—The John Hopkins University) (13 pages).
International Preliminary Report on Patentability dated Feb. 28, 2017 by the International Searching Authority for International Application No. PCT/US2015/046806, which was filed on Aug. 25, 2015 and published as WO/2016/033114 on Mar. 3, 2016 (Applicant—The John Hopkins University) (9 pages).
Certificate of Patent issued on Jan. 27, 2016 by the European Patent Office for European Patent Application No. 0933012.0, which was filed on Nov. 15, 2010 and granted as 2300041 on Mar. 30, 2011 (Inventor—Luo et al.; Applicant—The Johns Hopkins University) (1 page).
Preliminary Amendment filed on Feb. 22, 2017 by the United States Patent and Trademark Office for U.S. Appl. No. 15/505,882, filed Feb. 22, 2017 (Inventor—Luo et al.; Applicant—The Johns Hopkins University) (11 pages).
Antonarakis, et al., "Androgen Receptor Splice Variant 7 and Efficacy of Taxane Chemotherapy in Patients With Metastatic Castration-Resistant Prostate Cancer",JAMA Oncol. 1(5):582-591 (2015).
Nakazawa et al., "Androgen Receptor Splice Variants in the Era of Enzalutamide and Abiraterone", Horm Cancer.5(5):265-273, (2014).
Extended European Search Report dated Dec. 8, 2017, by the European Patent Office for EP Application No. 15835018.1, which was filed on Aug. 25, 2015 and published as EP 3186393 A1 on Jul. 5, 2017 (Applicant—The Johns Hopkins University) (8 pages).
Jenster G et al: "Functional domains of the human androgen receptor", Journal of Steroid Biochemistry and Molecular Biology, Elsevier Science Ltd. vol. 41, No. 3-8,(1992), pp. 671-675.
Communication pursuant to Article 94(3) EPC dated Apr. 19, 2018 by the European Patent Office for EP Application No. 16152616.5, which was filed on Apr. 16, 2009 and published as EP 3062106 on Aug. 31, 2016 (Applicant—The John Hopkins University) (8 pages).
Jiang et al. "Detection of androgen receptor mutations in circulating tumor cells in castration-resistant prostate cancer" Clin. Chem. 56(9): 1492-1495 (2010).

(56) References Cited

OTHER PUBLICATIONS

Non Final Rejection dated Oct. 19, 2018 by the USPTO for U.S. Appl. No. 15/309,986, filed Nov. 9, 2016 and published as US 2017/0268063 A1 on Sep. 21, 2017 (Inventor—Jun Luo, et al.)(10 pages).
Notice of Reasons for Refusal dated Jun. 3, 2019 by the Japanese Patent Office for JP Application No. 2017-511236, which was filed on Aug. 25, 2015 and published as 2017-534248 on Nov. 24, 2017 (Applicant—Unknown) (Original—4 pages//Translation—3 pages).
Androgen receptor splice variant-7 predicts resistance to enzalutamide in patients with castration-resistant prostate cancer, Proceedings: AACR Annual Meeting 2014, Apr. 5-9, 2014, (Abstract No. 2910).
Final Rejection dated May 17, 2019 by the USPTO Office for U.S. Appl. No. 15/309,986, filed Nov. 9, 2016 and published as US-2017-0268063-A1 on Sep. 21, 2017 (Inventor—Luo et al) (10 pages).
Emmanuel S Antonarakis et al: "Androgen receptor splice variant-7 predicts resistance to enzalutamide in patients with castration-resistant prostate cancer | Cancer Research", Cancer Research, (2014) (Abstract).
EP Communication pursuant to Article 94(3) EPC dated Mar. 28, 2019 by the European Patent Office for EP Application No. 15835018.1, which was filed on Aug. 25, 2015 (Applicant—The John Hopkins University) (7 pages).
Non Final Rejection dated Jul. 25, 2019 by the USPTO for U.S. Appl. No. 15/505,882, filed Feb. 22, 2017 and published as US 2017/0275673 A1 on Sep. 28, 2017 (Inventor—Jun Luo) (17 pages).
Commmunication pursuant to Article 94(3) EPC dated Aug. 6, 2019 by the European Patent Office for EP Application No. 16152616.5, which was filed on Apr. 16, 2009 and published as EP 3062106 on Aug. 31, 2016 (Applicant—The John Hopkins University) (4 pages).
Commmunication pursuant to Article 94(3) EPC dated Jul. 8, 2019 by the European Patent Office for EP Application No. 15796390.1, which was filed on May 19, 2015 and published as EP 3146081 on Mar. 29, 2017 (Applicant—The John Hopkins University) (6 pages).
Final Rejection dated Jan. 6, 2020 by the USPTO for U.S. Appl. No. 15/505,882, filed Feb. 22, 2017 and published as US 2017-0275673 A1 on Sep. 28, 2017 (Inventor—Jun Luo) (19 Pages).
EP Communication dated Feb. 21, 2020 by the European Patent Office for EP Application No. 15835018.1, which was filed on Aug. 25, 2015 and published as EP 3186393 A1 on Jul. 5, 2017 (Applicant—The John Hopkins University) (8 pages).

\* cited by examiner

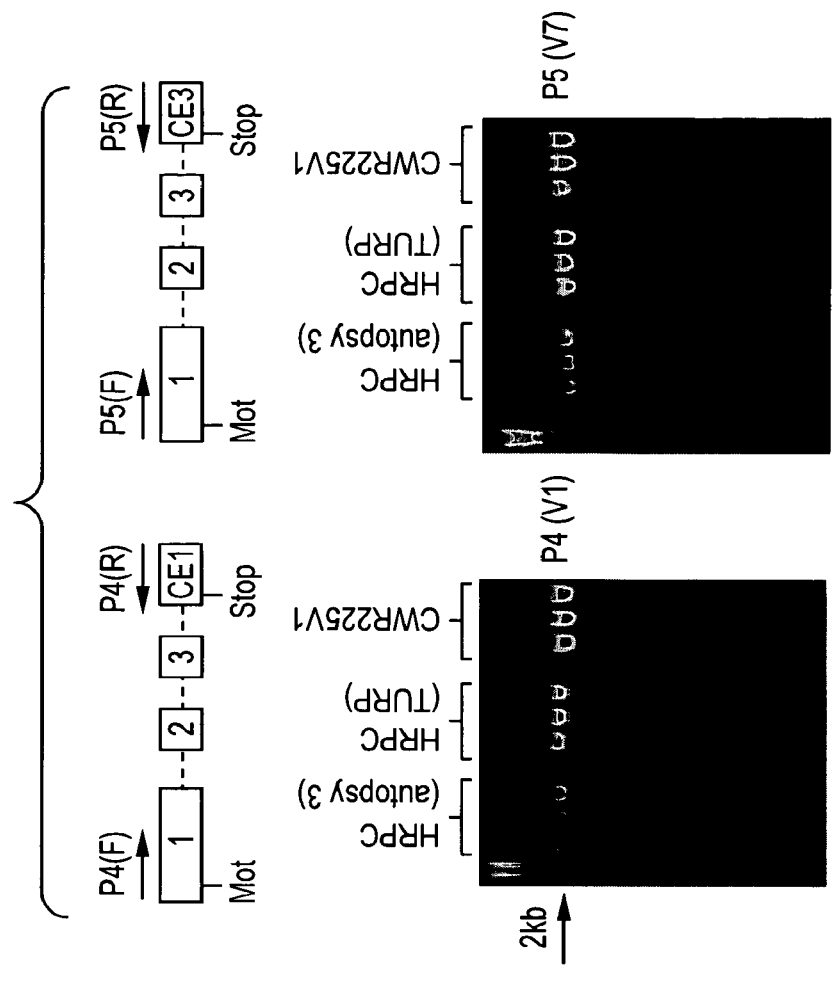
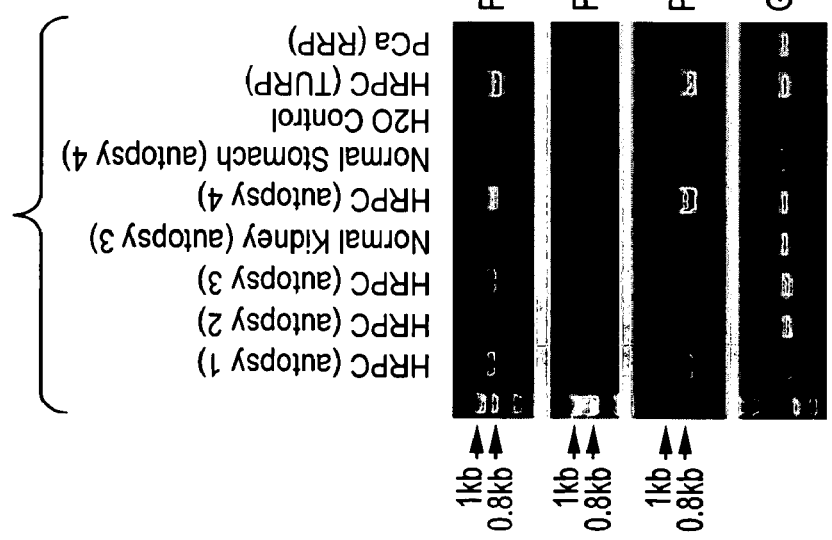

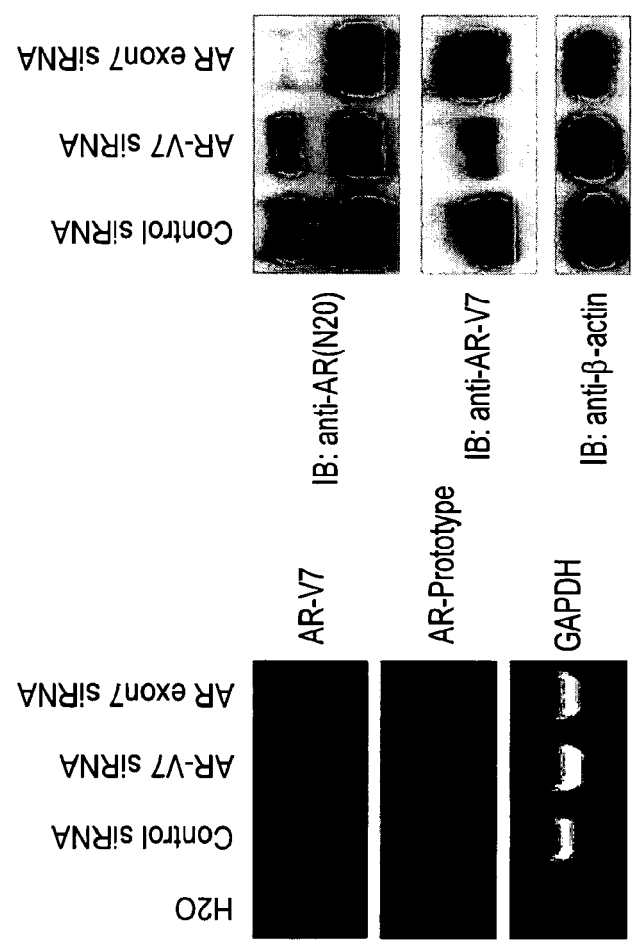

FIG. 12B

A&G EIA Work Sheet

Project: JHU019
Antigen Name: 1. JHU014-BSA (peptide)  2. JHU016-BSA (peptide)
Conjugation: ☐ None  ☒ BSA (both)  ☐ Other
Operator: KK
Date: 10-03-08

Antigen Concentrations: 0.5 mg/ml (both)
Amounts of Ag to be used for coating: 100ng/well in ☒ Sodium Bicarbonate Buffer  ☐ Other 96 well formats used in this assay:

| Plate # | 1 | 2 | 3 | 4 | 5 | 6 | 7 | 8 | 9 | 10 | 11 | 12 |
|---|---|---|---|---|---|---|---|---|---|---|---|---|
| A | | | | | | | | | | | | |
| B | Mouse1 1:1K | Mouse1 1:5K | Mouse1 1:10K | Mouse1 1:50K | Mouse1 1:100K | NC | Mouse2 1:1K | Mouse2 1:5K | Mouse2 1:10K | Mouse2 1:50K | Mouse2 1:100K | NC |
| C | Mouse3 1:1K | Mouse3 1:5K | Mouse3 1:10K | Mouse3 1:50K | Mouse3 1:100K | NC | Mouse4 1:1K | Mouse4 1:5K | Mouse4 1:10K | Mouse4 1:50K | Mouse4 1:100K | NC |
| D | Mouse5 1:1K | Mouse5 1:5K | Mouse5 1:10K | Mouse5 1:50K | Mouse5 1:100K | NC | Mouse6 1:1K | Mouse6 1:5K | Mouse6 1:10K | Mouse6 1:50K | Mouse6 1:100K | NC |
| E | Mouse1 1:1K | Mouse1 1:5K | Mouse1 1:10K | Mouse1 1:50K | Mouse1 1:100K | NC | Mouse2 1:1K | Mouse2 1:5K | Mouse2 1:10K | Mouse2 1:50K | Mouse2 1:100K | NC |
| F | Mouse3 1:1K | Mouse3 1:5K | Mouse3 1:10K | Mouse3 1:50K | Mouse3 1:100K | NC | Mouse4 1:1K | Mouse4 1:5K | Mouse4 1:10K | Mouse4 1:50K | Mouse4 1:100K | NC |
| G | Mouse5 1:1K | Mouse5 1:5K | Mouse5 1:10K | Mouse5 1:50K | Mouse5 1:100K | NC | Mouse6 1:1K | Mouse6 1:5K | Mouse6 1:10K | Mouse6 1:50K | Mouse6 1:100K | NC |
| H | | | | | | | | | | | | |

Rows B–D: JHU014-BSA; Rows E–G: JHU016-BSA

Coating of antigen: O/N hr at 4°C  Volume/well: 100ul
Blocking Solution
Blocking Agent: ☒ Milk  ☐ BSA  ☐ Other:
Buffer: ☒ PBS  ☐ Other:
Concentration of blocking solution: 5% or ___ mg/ml
Blocking condition: ✓1hr at RT °C Primary Antibody: Great α-mouse IgG (H+L) @ 1-2000 Lot# 393738A
Primary Ab dilutions: Serial in 5% Milk-PBS Substrate: TMB  TB#2
Other: ___  Lot#: ___
Location: ___
Location: ___

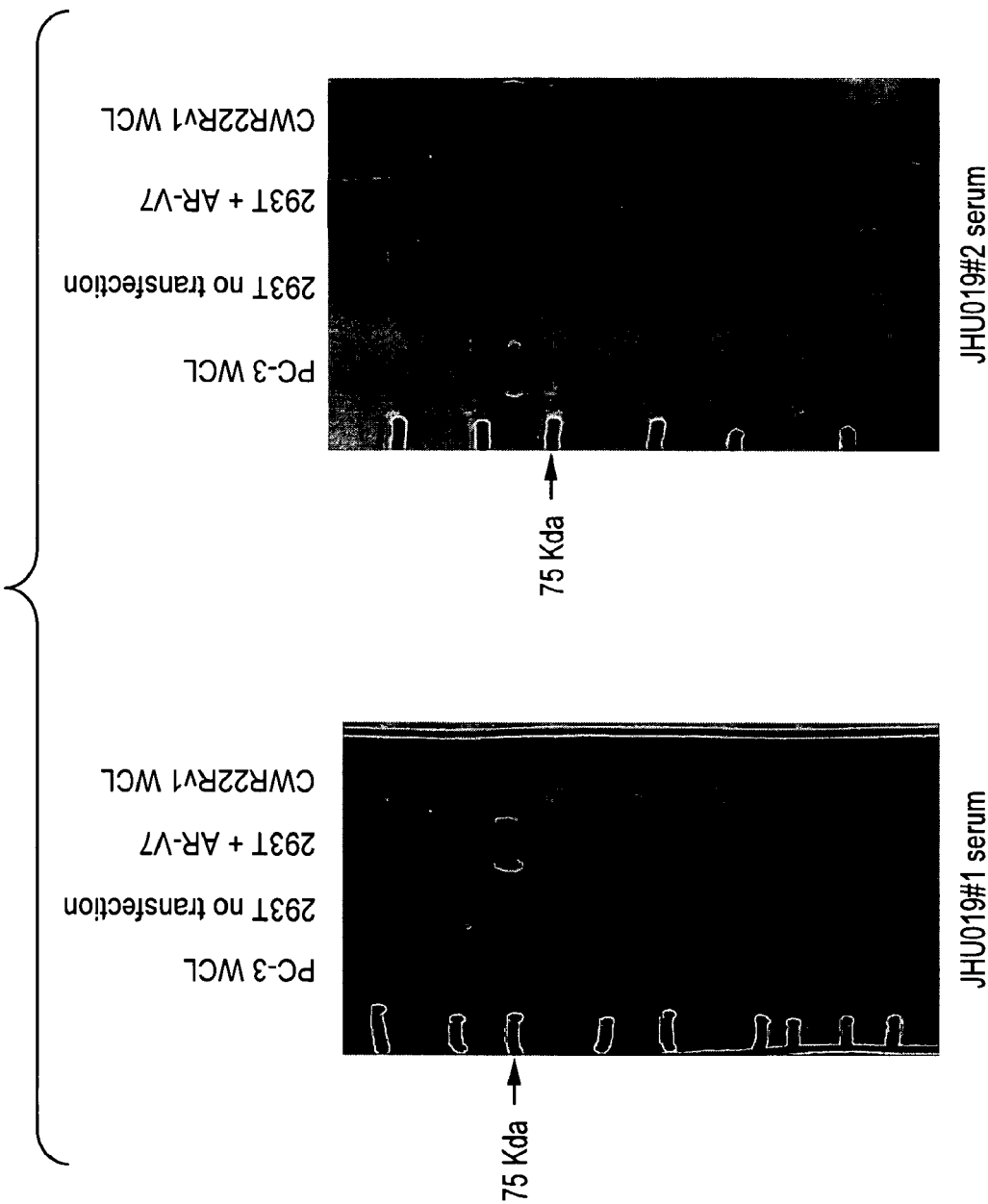

FIG. 14B

A&G EIA Work Sheet

Project: JHU019    Operator: KK    Date: 12-01-08
Antigen Name: 1. JHU014-BSA  ☒ peptide  ☐ protein  ☐ Others
Conjugation:  ☐ None  ☒ BSA (both)    ☐ Other
                                       ☐
Antigen Concentrations: 0.5 mg/ml
Amounts of Ag to be used for coating: 100 ng/well in ☒  Sodium Bicarbonate Buffer ☐ Other 96 well formats used in this assay:                                    Initial

| Plate # 4 | 1 | 2 | 3 | 4 | 5 | 6 | 7 | 8 | 9 | 10 | 11 | 12 |
|---|---|---|---|---|---|---|---|---|---|---|---|---|
| A | | | | | | | | | | | | |
| B | | | | | | | | | | | | |
| C | | | | | | | | | | | | |
| D | | | | | | | | | | | | |
| E | | | | | | | | | | | | |
| F | | | | | | | | | | | | |
| G | | | | | | | | | | | | |
| H | | | | NC | PC | | | | | | | |

Coating of antigen:   O/N  hr at  4 °C   Volume/well: 100ul
Blocking Solution
Blocking Agent:    ☒ Milk      ☐ BSA       ☐ Other:_____
Buffer:            ☒ PBS       ☐ Other: _____
            Concentration of blocking solution: 5%  or ___ mg/ml
            Blocking condition: ☒ 1hr at RT °C Primary Antibody:   ☐ tail bleed   ☒ culture sup   ☐ ascites   ☐ BioRx Sup   ☐ Pur Ab
Primary Ab dilutions: 1:2 in 5% Milk-PBS Secondary Antibody: HRP goat anti-mouse IgG:   ☒ H+L  ☐ Gamma  ☐ Mu Lot # 310004811
                    Other:_____
Substrate:  TMB     Lot #

Positive Control: Sample: M#2 cardiac (11/14/08)    Concentration/dilution: 1:1K
                  Location: 4H5
Negative Control: Sample: 5% Milk-PBS               Concentration/dilution: _____
                  Location: 4H4

FIG. 15B

A&G EIA Work Sheet

Project: JHU019      Operator: KK     Date: 12-04-08
Antigen Name: JHU014-BSA   ☒ peptide   ☐ protein   ☐ Others
Conjugation:   ☐ None   ☒ BSA          ☐ Other Antigen Concentrations: 0.5 mg/ml
Amounts of Ag to be used for coating: 100 ng/well in ☒ Sodium Bicarbonate Buffer ☐ Other 96 well formats used in this assay:            Confirmatory

| Plate # | 1 | 2 | 3 | 4 | 5 | 6 | 7 | 8 | 9 | 10 | 11 | 12 |
|---|---|---|---|---|---|---|---|---|---|---|---|---|
| A |  | 1A1 | 1A12 | 1C8 | 1E5 | 1F12 | 1H1 | 1H6 | 1H12 | 2A1 | 2A2 |  |
| B |  | 2A12 | 2B1 | 2B6 | 2D11 | 2D12 | 2E1 | 2E2 | 2E3 | 2H1 | 3A1 |  |
| C |  | 3A2 | 3A8 | 3A12 | 3B5 | 3H1 | 3H3 | 3H12 | 4A1 | 4E3 | 4E4 |  |
| D |  | 4F7 | 4G11 | 4G12 | NC | PC |  |  |  |  |  |  |
| E |  |  |  |  |  |  |  |  |  |  |  |  |
| F |  |  |  |  |  |  |  |  |  |  |  |  |
| G |  |  |  |  |  |  |  |  |  |  |  |  |
| H |  |  |  |  |  |  |  |  |  |  |  |  |

(Rows A–D: 2°Ab=Goat x-Mouse IgG (Gamma); Rows E–H: 2°Ab=Goat x-Mouse IgG)

Coating of antigen: O/N hr at 4 °C   Volume/well: 100ul
Blocking Solution
Blocking Agent:    ☒ Milk    ☐ BSA    ☐ Other: _____
Buffer:            ☒ PBS    ☐ Other: _____
               Concentration of blocking solution: 5%
               Blocking condition: 1hr at RT Primary Antibody:   ☐ tail bleed   ☒ culture sup   ☐ ascites   ☐ BioRx Sup   ☐ Pur Ab
Primary Ab dilutions: 1:2 in 5% Milk-PBS Secondary Antibody: HRP goat anti-mouse IgG:   ☐ H+L   ☒ Gamma   ☒ Mu Lot # Gamma:51202611
               Other: _____             Mu:383028A
Substrate: TMB Positive Control:   Sample: JHU019 M#2 cardiac bleed 11/14/08 (1:1K)
                  Location: D6, H6
Negative Control: Sample: 5% Milk-PBS
                  Location: D5, H5

Selection of the positive monoclonal anti-AR-V7 hybridomas

SEQUENCE LISTING

<160> NUMBER OF SEQ ID NOS: 47

<210> SEQ ID NO 1
<211> LENGTH: 1198
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1

```
tgtcactatg gagctctcac atgtggaagc tgcaaggtct tcttcaaaag agccgctgaa      60
gggaaacaga agtacctgtg cgccagcaga aatgattgca ctattgataa attccgaagg     120
aaaaattgtc catcttgtcg tcttcggaaa tgttatgaag cagggatgac tctgggagaa     180
aaattccggg ttggcaattg caagcatctc aaaatgacca gaccctgaag aaaggctgac     240
ttgcctcatt caaaatgagg gctctagagg gctctagtgg atagtctgga gaaacctggc     300
gtctgaggct taggagctta ggttttttgct cctcaacaca gactttgacg ttggggttgg     360
gggctactct cttgattgct gactccctcc agcgggacca atagtgtttt cctacctcac     420
agggatgttg tgaggacggg ctgtagaagt aatagtggtt accactcatg tagttgtgag     480
tatcatgatt attgtttcct gtaatgtggc ttggcattgg caaagtgctt tttgattgtt     540
cttgatcaca tatgatgggg gccaggcact gactcaggcg gatgcagtga agctctggct     600
cagtcgcttg cttttcgtgg tgtgctgcca ggaagaaact ttgctgatgg gactcaaggt     660
gtcaccttgg acaagaagca actgtgtctg tctgaggttc ctgtggccat ctttatttgt     720
gtattaggca attcgtattt cccccttagg ttctagcctt ctggatccca gccagtgacc     780
tagatcttag cctcaggccc tgtcactgag ctgaaggtag tagctgatcc acagaagttc     840
agtaaacaag gaccagattt ctgcttctcc aggagaagaa gccagccaac cctctcttc      900 aaacacactg agagactaca gtccgacttt ccctcttaca tctagcctta ctgtagccac     960
actccttgat tgctctctca catcacatgc ttctcttcat cagttgtaag cctctcattc    1020
ttctcccaag ccagactcaa atattgtatt gatgtcaaag aagaatcact tagagtttgg    1080
aatatcttgt tctctctctg ctccatagct tccatattga caccagtttc tttctagtgg    1140
agaagtggag tctgtgaagc cagggaaaca cacatgtgag agtcagaagg actctccc      1198
```

<210> SEQ ID NO 2
<211> LENGTH: 842
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 2

```
tgtcactatg gagctctcac atgtggaagc tgcaaggtct tcttcaaaag agccgctgaa      60
gggaaacaga agtacctgtg cgccagcaga aatgattgca ctattgataa attccgaagg     120
aaaaattgtc catcttgtcg tcttcggaaa tgttatgaag cagggatgac tctgggagct     180
gttgttgttt ctgaaagaat cttgagggtg tttggagtct cagaatggct tccttaaaga     240
ctaccttcag actctcagct gctcatccac aacagagatc agcctttctt tgtagatgat     300
tcattcctgg ctgcatttga aaccacata ttgttaattg cttgacgaat ttaaatccct     360
tgactacttt tcatttcaga aaacacttac aaaaaaagtc caaatgagga ccttccctcc     420
agtgaattag ctgtggcttt ctcacagtcc atagttagga taaatgtaaa gccatttctc     480
atttttctcc gcactttcca agggtacact ccttgtttcc aagatggaat gagaaataaa     540
gaagtgccct tcctgccatc ttctcccctg acctttcct ccttcccact ttcctcctat     600 tcctcccccaa acatgattta tttctgcgtt ttgcaactct tgagttctca gcatttagta     660
aatggtgttg gtccctgttg attccttcct ctcctggacc atggaaggta gtaggccttt     720
cagaaatttc aggtagcagc caaaccccag aagaagagaa ggaacacaga gacctagacc     780
```

```
atgtgagaac ctgaggtgtg cagcatttac ttcacagatt cgtctagcat atttgagagg    840
tg                                                                   842
```

<210> SEQ ID NO 3
<211> LENGTH: 959
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

```
tgtcactatg gagctctcac atgtggaagc tgcaaggtct tcttcaaaag agccgctgaa     60
gggaaacaga agtacctgtg cgccagcaga atgattgca ctattgataa attccgaagg    120
aaaaattgtc catcttgtcg tcttcggaaa tgttatgaag cagggatgac tctgggaggg    180
aaacagaagt acctgtgcgc cagcagaaat gattgcacta ttgataaatt ccgaaggaaa    240
aattgtccat cttgtcgtct tcggaaatgt tatgaagcag gatgactct gggagctgtt    300 gttgtttctg aaagaatctt gagggtgttt ggagtctcag aatggcttcc ttaaagacta    360
ccttcagact ctcagctgct catccacaac agagatcagc ctttctttgt agatgattca    420
ttcctggctg catttgaaaa ccacatattg ttaattgctt gacgaattta atcccttga     480 ctacttttca tttcagaaaa cacttacaaa aaagtccaa atgaggacct ccctccagt    540 gaattagctg tggctttctc acagtccata gttaggataa atgtaaagcc atttctcatt    600
tttctccgca ctttccaagg gtacactcct tgtttccaag atggaatgag aaataaagaa    660
gtgcccttcc tgccatcttc tccctgacc cttcctcct tcccactttc ctcctattcc      720
tccccaaaca tgatttattt ctgcgttttg caactcttga gttctcagca tttagtaaat   780
ggtgttggtc cctgttgatt ccttcctctc ctggaccatg gaaggtagta ggccttttcag   840 aaattttcagg tagcagccaa accccagaag aagagaagga acacagagac ctagaccatg   900
tgagaacctg aggtgtgcag catttacttc acagattcgt ctagcatatt tgagaggtg    959
```

<210> SEQ ID NO 4
<211> LENGTH: 1126
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

```
tgtcactatg gagctctcac atgtggaagc tgcaaggtct tcttcaaaag agccgctgaa     60 ggattttca gaatgaacaa attaaaagaa tcatcagaca ctaaccccaa gccatactgc    120
atggcagcac caatgggact gacagaaaac aacagaaata ggaagaaatc ctacagagaa    180
acaaacttga agctgtctc atggcctttg aatcatactt aagttttatg atggaaggat    240
acgactatga agaaagacac agagcaacat cagacagtca agaatttcag agccagctgg    300
catgcagtgg acctcatgcc agcccatttt atgactattt agggaaacag aagtacctgt    360
gcgccagcag aaatgattgc actattgata aattccgaag gaaaaattgt ccatcttgtc    420
gtcttcggaa atgttatgaa gcagggatga ctctgggagc agctgttgtt gtttctgaaa    480
gaatcttgag ggtgtttgga gtctcagaat ggcttcctta agactaccct tcagactctc    540
agctgctcat ccacaacaga gatcagcct tctttgtaga tgattcattc ctggctgcat    600
ttgaaaacca catattgtta attgcttgac gaatttaaat cccttgacta cttttcattt    660
```

| | | | | |
|---|---|---|---|---|
| cagaaaacac | ttacaaaaaa | agtccaaatg | aggaccttcc | ctccagtgaa ttagctgtgg | 720 |
| ctttctcaca | gtccatagtt | aggataaatg | taaagccatt | tctcattttt ctccgcactt | 780 |
| tccaagggta | cactccttgt | ttccaagatg | gaatgagaaa | taagaagtg cccttcctgc | 840 |
| catcttctcc | cctgacccct | tcctccttcc | cactttcctc | ctattcctcc ccaaacatga | 900 |
| tttatttctg | cgttttgcaa | ctcttgagtt | ctcagcattt | agtaaatggt gttggtccct | 960 |
| gttgattcct | tcctctcctg | gaccatggaa | ggtagtaggc | ctttcagaaa tttcaggtag | 1020 |
| cagccaaacc | ccagaagaag | agaaggaaca | cagagaccta | gaccatgtga gaacctgagg | 1080 |
| tgtgcagcat | ttacttcaca | gattcgtcta | gcatatttga | gaggtg | 1126 |

<210> SEQ ID NO 5
<211> LENGTH: 1243
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 5

| | | | | |
|---|---|---|---|---|
| tgtcactatg | gagctctcac | atgtggaagc | tgcaaggtct | tcttcaaaag agccgctgaa | 60 |
| gggaaacaga | agtacctgtg | cgccagcaga | aatgattgca | ctattgataa attccgaagg | 120 |
| aaaaattgtc | catcttgtcg | tcttcggaaa | tgttatgaag | cagggatgac tctgggagga | 180 |
| tttttcagaa | tgaacaaatt | aaaagaatca | tcagacacta | accccaagcc atactgcatg | 240 |
| gcagcaccaa | tgggactgac | agaaaacaac | agaaatagga | gaaatcctta cagagaaaca | 300 |
| aacttgaaag | ctgtctcatg | gcctttgaat | catacttaag | ttttatgatg gaaggatacg | 360 |
| actatgaaga | aagacacaga | gcaacatcag | acagtcaaga | atttcagagc cagctggcat | 420 |
| gcagtggacc | tcatgccagc | ccattttatg | actatttagg | gaaacagaag tacctgtgcg | 480 |
| ccagcagaaa | tgattgcact | attgataaat | tccgaaggaa | aaattgtcca tcttgtcgtc | 540 |
| ttcggaaatg | ttatgaagca | gggatgactc | tgggagcagc | tgttgttgtt tctgaaagaa | 600 |
| tcttgagggt | gttggagtc | tcagaatggc | ttccttaaag | actaccttca gactctcagc | 660 |
| tgctcatcca | aacagagat | cagccttct | ttgtagatga | ttcattcctg gctgcatttg | 720 |
| aaaaccacat | attgttaatt | gcttgacgaa | tttaaatccc | ttgactactt ttcatttcag | 780 |
| aaaacactta | caaaaaagt | ccaaatgagg | accttccctc | cagtgaatta gctgtggctt | 840 |
| tctcacagtc | catagttagg | ataaatgtaa | agccatttct | cattttctc cgcactttcc | 900 |
| aagggtacac | tccttgtttc | caagatggaa | tgagaaataa | agaagtgccc ttcctgccat | 960 |
| cttctcccct | gacccttcc | tcttcccac | tttcctccta | ttcctcccca acatgatttt | 1020 |
| atttctgcgt | tttgcaactc | ttgagttctc | agcatttagt | aaatggtgtt ggtccctgtt | 1080 |
| gattccttcc | tctcctggac | catggaaggt | agtaggcctt | tcagaaattt caggtagcag | 1140 |
| ccaaacccca | gaagaagaga | aggaacacag | agacctagac | catgtgagaa cctgaggtgt | 1200 |
| gcagcattta | cttcacagat | tcgtctagca | tatttgagag | gtg | 1243 |

<210> SEQ ID NO 6
<211> LENGTH: 888
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 6

```
ggaaacagaa gtacctgtgc gccagcagaa atgattgcac tattgataaa ttccgaagga      60
aaaattgtcc atcttgtcgt cttcggaaat gttatgaagc agggatgact ctgggagact     120
agaattccaa agaccctcag gctggtgatg caagtgggaa gtctcatttc tgagaagtgc     180
tgcttcctac ccacaattct tgatagctg agtgctttag ctgatctgca taactgaggt      240
gtgcaccaag gagcagaatt actctataaa ttttggcatc aacatgtgca acttgtgact     300
cagcactttg aaactctggg gattttttg tttggttggt ttttgtttta agatgtcctg      360
tggtatagtg gaaatagtac aatagactca gatacagaga ggccttgttt ctagtcttgg     420
ttctgtcact tactatcttg atgtccttgc acaaatcacc agacctctct gagcctcagt     480
ttctccaacc acactgtggg aataataaaa tcttttttac ggcattgttg taagtatgca     540
gagaaactgg tacacagtag ccacacaatc aatgtcaccg tacccttcag cccttctttt     600
gtggatgaaa aatggtcttt gtgctcccag tcaccactgg ggtctgttct ctctctctct     660
gctgttacag tgtggctttg gttcttgttt ctttgttctt tggtctgtaa attacccttg     720
aaacaaccct tgaaatttcc actccatgac ctaaatcgtc atccctaaat tggttacata     780
catatttggt gacactttgg aggggaaaag ctttatgtct ctctaacgtg tagttcttaa     840
gggaatttgc atatggaaaa aacagagact gcgtctctta attcctcc                  888
```

<210> SEQ ID NO 7
<211> LENGTH: 968
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 7

```
ggaaacagaa gtacctgtgc gccagcagaa atgattgcac tattgataaa ttccgaagga      60
aaaattgtcc atcttgtcgt cttcggaaat gttatgaagc agggatgact ctgggagcag     120
gcagcagagt gtcataaaga attaacaacg tggaactcag ttactgggat tcttccatt      180
ctcctttgat tctctagact agaattccaa agaccctcag gctggtgatg caagtgggaa     240
gtctcatttc tgagaagtgc tgcttcctac ccacaattct tgatagctg agtgctttag      300
ctgatctgca taactgaggt gtgcaccaag gagcagaatt actctataaa ttttggcatc     360
aacatgtgca acttgtgact cagcactttg aaactctggg gattttttg tttggttggt      420
ttttgtttta agatgtcctg tggtatagtg gaaatagtac aatagactca gatacagaga     480
ggccttgttt ctagtcttgg ttctgtcact tactatcttg atgtccttgc acaaatcacc     540
agacctctct gagcctcagt ttctccaacc acactgtggg aataataaaa tcttttttac     600
ggcattgttg taagtatgca gagaaactgg tacacagtag ccacacaatc aatgtcaccg     660
tacccttcag cccttctttt gtggatgaaa aatggtcttt gtgctcccag tcaccactgg     720
ggtctgttct ctctctctct gctgttacag tgtggctttg gttcttgttt ctttgttctt    780
tggtctgtaa attacccttg aaacaaccct tgaaatttcc actccatgac ctaaatcgtc    840
atccctaaat tggttacata catatttggt gacactttgg aggggaaaag ctttatgtct    900
ctctaacgtg tagttcttaa gggaatttgc atatggaaaa aacagagact gcgtctctta    960
attcctcc                                                             968
```

<210> SEQ ID NO 8

```
<211> LENGTH: 75
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Cys His Tyr Gly Ala Leu Thr Cys Gly Ser Cys Lys Val Phe Phe Lys
1               5                   10                  15

Arg Ala Ala Glu Gly Lys Gln Lys Tyr Leu Cys Ala Ser Arg Asn Asp
            20                  25                  30

Cys Thr Ile Asp Lys Phe Arg Arg Lys Asn Cys Pro Ser Cys Arg Leu
        35                  40                  45

Arg Lys Cys Tyr Glu Ala Gly Met Thr Leu Gly Glu Lys Phe Arg Val
    50                  55                  60

Gly Asn Cys Lys His Leu Lys Met Thr Arg Pro
65                  70                  75

<210> SEQ ID NO 9
<211> LENGTH: 78
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Cys His Tyr Gly Ala Leu Thr Cys Gly Ser Cys Lys Val Phe Phe Lys
1               5                   10                  15

Arg Ala Ala Glu Gly Lys Gln Lys Tyr Leu Cys Ala Ser Arg Asn Asp
            20                  25                  30

Cys Thr Ile Asp Lys Phe Arg Arg Lys Asn Cys Pro Ser Cys Arg Leu
        35                  40                  45

Arg Lys Cys Tyr Glu Ala Gly Met Thr Leu Gly Ala Val Val Val Ser
    50                  55                  60

Glu Arg Ile Leu Arg Val Phe Gly Val Ser Glu Trp Leu Pro
65                  70                  75

<210> SEQ ID NO 10
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Cys His Tyr Gly Ala Leu Thr Cys Gly Ser Cys Lys Val Phe Phe Lys
1               5                   10                  15

Arg Ala Ala Glu Gly Lys Gln Lys Tyr Leu Cys Ala Ser Arg Asn Asp
            20                  25                  30

Cys Thr Ile Asp Lys Phe Arg Arg Lys Asn Cys Pro Ser Cys Arg Leu
        35                  40                  45

Arg Lys Cys Tyr Glu Ala Gly Met Thr Leu Gly Gly Lys Gln Lys Tyr
    50                  55                  60

Leu Cys Ala Ser Arg Asn Asp Cys Thr Ile Asp Lys Phe Arg Arg Lys
65                  70                  75                  80

Asn Cys Pro Ser Cys Arg Leu Arg Lys Cys Tyr Glu Ala Gly Met Thr
                85                  90                  95
```

Leu Gly Ala Val Val Ser Glu Arg Ile Leu Arg Val Phe Gly Val
            100             105             110

Ser Glu Trp Leu Pro
        115

<210> SEQ ID NO 11
<211> LENGTH: 73
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Cys His Tyr Gly Ala Leu Thr Cys Gly Ser Cys Lys Val Phe Phe Lys
1               5                   10                  15

Arg Ala Ala Glu Gly Phe Phe Arg Met Asn Lys Leu Lys Glu Ser Ser
            20                  25                  30

Asp Thr Asn Pro Lys Pro Tyr Cys Met Ala Ala Pro Met Gly Leu Thr
        35                  40                  45

Glu Asn Asn Arg Asn Arg Lys Lys Ser Tyr Arg Glu Thr Asn Leu Lys
    50                  55                  60

Ala Val Ser Trp Pro Leu Asn His Thr
65                  70

<210> SEQ ID NO 12
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Cys His Tyr Gly Ala Leu Thr Cys Gly Ser Cys Lys Val Phe Phe Lys
1               5                   10                  15

Arg Ala Ala Glu Gly Lys Gln Lys Tyr Leu Cys Ala Ser Arg Asn Asp
            20                  25                  30

Cys Thr Ile Asp Lys Phe Arg Arg Lys Asn Cys Pro Ser Cys Arg Leu
        35                  40                  45

Arg Lys Cys Tyr Glu Ala Gly Met Thr Leu Gly Gly Phe Phe Arg Met
    50                  55                  60

Asn Lys Leu Lys Glu Ser Ser Asp Thr Asn Pro Lys Pro Tyr Cys Met
65                  70                  75                  80

Ala Ala Pro Met Gly Leu Thr Glu Asn Asn Arg Asn Arg Lys Lys Ser
                85                  90                  95

Tyr Arg Glu Thr Asn Leu Lys Ala Val Ser Trp Pro Leu Asn His Thr
            100                 105                 110

<210> SEQ ID NO 13
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gly Lys Gln Lys Tyr Leu Cys Ala Ser Arg Asn Asp Cys Thr Ile Asp
1               5                   10                  15

Lys Phe Arg Arg Lys Asn Cys Pro Ser Cys Arg Leu Arg Lys Cys Tyr

```
                   20                  25                  30

Glu Ala Gly Met Thr Leu Gly Asp
        35                  40

<210> SEQ ID NO 14
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gly Lys Gln Lys Tyr Leu Cys Ala Ser Arg Asn Asp Cys Thr Ile Asp
1               5                   10                  15

Lys Phe Arg Arg Lys Asn Cys Pro Ser Cys Arg Leu Arg Lys Cys Tyr
            20                  25                  30

Glu Ala Gly Met Thr Leu Gly Ala Gly Ser Arg Val Ser
        35                  40                  45

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tgtcactatg gagctctcac atgtgg                                              26

<210> SEQ ID NO 16
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cacctctcaa atatgctaga cgaatctgt                                           29

<210> SEQ ID NO 17
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tgtcactatg gagctctcac atgtgg                                              26

<210> SEQ ID NO 18
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gtactcattc aagtatcaga tatgcggtat cat                                      33

<210> SEQ ID NO 19
```

<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 19
tgtcactatg gagctctcac atgtgg     26

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 20
ctgtggatca gctactacct tcagctc     27

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 21
gttgctcccg caagtttcct tctc     24

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 22
ctgttgtgga tgagcagctg agagtct     27

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 23
gttgctcccg caagtttcct tctc     24

<210> SEQ ID NO 24
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 24
tttgaatgag gcaagtcagc ctttct     26

<210> SEQ ID NO 25
<211> LENGTH: 32

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ccatcttgtc gtcttcggaa atgttatgaa gc                                32

<210> SEQ ID NO 26
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ctgttgtgga tgagcagctg agagtct                                      27

<210> SEQ ID NO 27
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ccatcttgtc gtcttcggaa atgttatgaa gc                                32

<210> SEQ ID NO 28
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tttgaatgag gcaagtcagc ctttct                                       26

<210> SEQ ID NO 29
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ccatcttgtc gtcttcggaa atgttatgaa gc                                32

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
agcttctggg ttgtctcctc agtgg                                        25

<210> SEQ ID NO 31
<211> LENGTH: 24
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 31
tacgaaagga ggagctcaat gcaa                                              24

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
agatctcatt tgggtgcttc cggt                                              24

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Cys Lys His Leu Lys Met Thr Arg Pro
1               5

<210> SEQ ID NO 34
<211> LENGTH: 4314
<212> TYPE: DNA
<213> ORGANISM: Homo sapiens

<400> SEQUENCE: 34
cgagatcccg gggagccagc ttgctgggag agcgggacgg tccggagcaa gcccagaggc        60
agaggaggcg acagagggaa aaagggccga gctagccgct ccagtgctgt acaggagccg       120
aagggacgca ccacgccagc cccagcccgg ctccagcgac agccaacgcc tcttgcagcg       180
cggcggcttc gaagccgccg cccggagctg ccctttcctc ttcggtgaag tttttaaaag       240
ctgctaaaga ctcggaggaa gcaaggaaag tgcctggtag gactgacggc tgcctttgtc       300
ctcctcctct ccaccccgcc tccccccacc ctgccttccc ccctccccc gtcttctctc        360 ccgcagctgc ctcagtcggc tactctcagc aacccccct caccacccctt ctccccaccc      420 gcccccccgc cccgtcggc ccagcgctgc cagcccgagt ttgcagagag gtaactccct        480
ttggctgcga gcgggcgagc tagctgcaca ttgcaaagaa ggctcttagg agccaggcga       540
ctggggagcg gcttcagcac tgcagccacg acccgcctgg ttaggctgca cgcggagaga       600
accctctgtt ttcccccact ctctctccac ctcctcctgc cttccccacc ccgagtgcgg       660
agccagagat caaaagatga aaaggcagtc aggtcttcag tagccaaaaa acaaaacaaa       720
caaaaacaaa aaagccgaaa taaagaaaa agataataac tcagttctta tttgcaccta       780
cttcagtgga cactgaattt ggaaggtgga ggattttgtt tttttctttt aagatctggg       840
catcttttga atctaccctt caagtattaa gagacagact gtgagcctag cagggcagat       900
cttgtccacc gtgtgtcttc ttctgcacga gactttgagg ctgtcagagc gcttttttgcg      960 tggttgctcc cgcaagtttc cttctctgga gcttcccgca ggtgggcagc tagctgcagc      1020
gactaccgca tcatcacagc ctgttgaact cttctgagca agagaagggg aggcggggta     1080
```

```
agggaagtag gtggaagatt cagccaagct caaggatgga agtgcagtta gggctgggaa      1140
gggtctaccc tcggccgccg tccaagacct accgaggagc tttccagaat ctgttccaga      1200
gcgtgcgcga agtgatccag aacccgggcc ccaggcaccc agaggccgcg agcgcagcac      1260
ctcccggcgc cagtttgctg ctgctgcagc agcagcagca gcagcagcag cagcagcagc      1320
agcagcagca gcagcagcag cagcagcagc agcaagagac tagccccagg cagcagcagc      1380
agcagcaggg tgaggatggt tctccccaag cccatcgtag aggccccaca ggctacctgg      1440
tcctggatga ggaacagcaa ccttcacagc cgcagtcggc cctggagtgc caccccgaga      1500
gaggttgcgt cccagagcct ggagccgccg tggccgccag caaggggctg ccgcagcagc      1560
tgccagcacc tccggacgag gatgactcag ctgccccatc cacgttgtcc ctgctgggcc      1620
ccactttccc cggcttaagc agctgctccg ctgaccttaa agacatcctg agcgaggcca      1680
gcaccatgca actccttcag caacagcagc aggaagcagt atccgaaggc agcagcagcg      1740
ggagagcgag ggaggcctcg ggggctccca cttcctccaa ggacaattac ttagggggca      1800
cttcgaccat ttctgacaac gccaaggagt tgtgtaaggc agtgtcggtg tccatgggcc      1860
tgggtgtgga ggcgttggag catctgagtc aggggaaca gcttcggggg gattgcatgt       1920
acgcccccact tttgggagtt ccacccgctg tgcgtccac tccttgtgcc ccattggccg      1980
aatgcaaagg ttctctgcta gacgacgcg caggcaagag cactgaagat actgctgagt       2040
attcccctt caagggaggt tacaccaaag gctagaagg cgagagccta ggctgctctg       2100
gcagcgctgc agcaggggagc tccgggacac ttgaactgcc gtctaccctg tctctctaca      2160
agtccggagc actggacgag gcagctgcgt accagagtcg cgactactac aactttccac      2220
tggctctggc cggaccgccg ccccctccgc cgcctcccca tccccacgct cgcatcaagc      2280
tggagaaccc gctggactac ggcagcgcct gggcggctgc ggcggcgcag tgccgctatg      2340
gggacctggc gagcctgcat ggcgcgggtg cagcgggacc cggttctggg tcaccctcag      2400
ccgccgcttc ctcatcctgg cacactctct tcacagccga agaaggccag ttgtatggac      2460
cgtgtggtgg tggtggggt ggtggcggc gcggcggcgg cggcggcggc ggcggcggcg       2520
gcggcggcgg cggcgaggcg ggagctgtag ccccctacgg ctacactcgg cccccctcagg     2580
ggctggcggg ccaggaaagc gacttcaccg cacctgatgt gtggtaccct ggcggcatgg      2640
tgagcagagt gccctatccc agtcccactt gtgtcaaaag cgaaatgggc ccctggatgg      2700
atagctactc cggaccttac ggggacatgc gtttggagac tgccagggac catgttttgc      2760
ccattgacta ttactttcca ccccagaaga cctgcctgat ctgtggagat gaagcttctg      2820
ggtgtcacta tggagctctc acatgtggaa gctgcaaggt cttcttcaaa agagccgctg      2880
aagggaaaca gaagtacctg tgcgccagca gaaatgattg cactattgat aaattccgaa      2940
ggaaaaattg tccatcttgt cgtcttcgga atgttatga agcagggatg actctgggag       3000
cccggaagct gaagaaactt ggtaatctga actacagga ggaaggagag gcttccagca       3060
ccaccagccc cactgaggag acaacccaga agctgacagt gtcacacatt gaaggctatg      3120
aatgtcagcc catctttctg aatgtcctgg aagccattga ccaggtgta gtgtgtgctg       3180
gacacgacaa caaccagccc gactcctttg cagccttgct ctctagcctc aatgaactgg      3240
gagagagaca gcttgtacac gtggtcaagt gggccaaggc cttgcctggc ttccgcaact      3300
tacacgtgga cgaccagatg gctgtcattc agtactcctg gatggggctc atggtgtttg      3360
ccatgggctg gcgatccttc accaatgtca actccaggat gctctacttc gcccctgatc      3420
```

-continued

```
tggttttcaa tgagtaccgc atgcacaagt cccggatgta cagccagtgt gtccgaatga    3480
ggcacctctc tcaagagttt ggatggctcc aaatcacccc ccaggaattc ctgtgcatga    3540
aagcactgct actcttcagc attattccag tggatgggct gaaaaatcaa aaattctttg    3600
atgaacttcg aatgaactac atcaaggaac tcgatcgtat cattgcatgc aaaagaaaaa    3660
atcccacatc ctgctcaaga cgcttctacc agctcaccaa gctcctggac tccgtgcagc    3720
ctattgcgag agagctgcat cagttcactt tgacctgct aatcaagtca cacatggtga     3780
gcgtggactt tccggaaatg atggcagaga tcatctctgt gcaagtgccc aagatccttt    3840
ctgggaaagt caagcccatc tatttccaca cccagtgaag cattggaaac cctatttccc    3900
caccccagct catgccccct ttcagatgtc ttctgcctgt tataactctg cactactcct    3960
ctgcagtgcc ttggggaatt tcctctattg atgtacagtc tgtcatgaac atgttcctga    4020
attctatttg ctgggctttt tttttctctt tctctccttt cttttcttc ttccctccct     4080
atctaaccct cccatggcac cttcagactt tgcttcccat tgtggctcct atctgtgttt    4140
tgaatggtgt tgtatgcctt taaatctgtg atgatcctca tatggcccag tgtcaagttg    4200
tgcttgttta cagcactact ctgtgccagc cacacaaacg tttacttatc ttatgccacg    4260
ggaagtttag agagctaaga ttatctgggg aaatcaaaac aaaaacaagc aaac          4314
```

<210> SEQ ID NO 35
<211> LENGTH: 920
<212> TYPE: PRT
<213> ORGANISM: Homo sapiens

<400> SEQUENCE: 35

```
Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
            20                  25                  30

Val Ile Gln Asn Pro Gly Pro Arg His Pro Glu Ala Ala Ser Ala Ala
        35                  40                  45

Pro Pro Gly Ala Ser Leu Leu Leu Leu Gln Gln Gln Gln Gln Gln Gln
    50                  55                  60

Gln Gln Gln Gln Gln Gln Gln Gln Gln Gln Gln Gln Gln Gln Gln Gln
65                  70                  75                  80

Glu Thr Ser Pro Arg Gln Gln Gln Gln Gln Gly Glu Asp Gly Ser
                85                  90                  95

Pro Gln Ala His Arg Arg Gly Pro Thr Gly Tyr Leu Val Leu Asp Glu
            100                 105                 110

Glu Gln Gln Pro Ser Gln Pro Gln Ser Ala Leu Glu Cys His Pro Glu
        115                 120                 125

Arg Gly Cys Val Pro Glu Pro Gly Ala Ala Val Ala Ala Ser Lys Gly
    130                 135                 140

Leu Pro Gln Gln Leu Pro Ala Pro Pro Asp Glu Asp Ser Ala Ala
145                 150                 155                 160

Pro Ser Thr Leu Ser Leu Leu Gly Pro Thr Phe Pro Gly Leu Ser Ser
                165                 170                 175

Cys Ser Ala Asp Leu Lys Asp Ile Leu Ser Glu Ala Ser Thr Met Gln
            180                 185                 190

Leu Leu Gln Gln Gln Gln Gln Glu Ala Val Ser Glu Gly Ser Ser Ser
        195                 200                 205

Gly Arg Ala Arg Glu Ala Ser Gly Ala Pro Thr Ser Ser Lys Asp Asn
    210                 215                 220
```

```
Tyr Leu Gly Gly Thr Ser Thr Ile Ser Asp Asn Ala Lys Glu Leu Cys
225                 230                 235                 240

Lys Ala Val Ser Val Ser Met Gly Leu Gly Val Glu Ala Leu Glu His
            245                 250                 255

Leu Ser Pro Gly Glu Gln Leu Arg Gly Asp Cys Met Tyr Ala Pro Leu
        260                 265                 270

Leu Gly Val Pro Pro Ala Val Arg Pro Thr Pro Cys Ala Pro Leu Ala
            275                 280                 285

Glu Cys Lys Gly Ser Leu Leu Asp Asp Ser Ala Gly Lys Ser Thr Glu
        290                 295                 300

Asp Thr Ala Glu Tyr Ser Pro Phe Lys Gly Tyr Thr Lys Gly Leu
305                 310                 315                 320

Glu Gly Glu Ser Leu Gly Cys Ser Gly Ser Ala Ala Gly Ser Ser
                325                 330                 335

Gly Thr Leu Glu Leu Pro Ser Thr Leu Ser Leu Tyr Lys Ser Gly Ala
            340                 345                 350

Leu Asp Glu Ala Ala Ala Tyr Gln Ser Arg Asp Tyr Asn Phe Pro
            355                 360                 365

Leu Ala Leu Ala Gly Pro Pro Pro Pro Pro Pro His Pro His
370                 375                 380

Ala Arg Ile Lys Leu Glu Asn Pro Leu Asp Tyr Gly Ser Ala Trp Ala
385                 390                 395                 400

Ala Ala Ala Ala Gln Cys Arg Tyr Gly Asp Leu Ala Ser Leu His Gly
                405                 410                 415

Ala Gly Ala Ala Gly Pro Gly Ser Gly Ser Pro Ser Ala Ala Ala Ser
                420                 425                 430

Ser Ser Trp His Thr Leu Phe Thr Ala Glu Glu Gly Gln Leu Tyr Gly
            435                 440                 445

Pro Cys Gly Gly Gly Gly Gly Gly Gly Gly Gly Gly Gly Gly
            450                 455                 460

Gly Gly Gly Gly Gly Gly Gly Gly Glu Ala Gly Ala Val Ala Pro
465                 470                 475                 480

Tyr Gly Tyr Thr Arg Pro Pro Gln Gly Leu Ala Gly Gln Glu Ser Asp
                485                 490                 495

Phe Thr Ala Pro Asp Val Trp Tyr Pro Gly Gly Met Val Ser Arg Val
            500                 505                 510

Pro Tyr Pro Ser Pro Thr Cys Val Lys Ser Glu Met Gly Pro Trp Met
            515                 520                 525

Asp Ser Tyr Ser Gly Pro Tyr Gly Asp Met Arg Leu Glu Thr Ala Arg
            530                 535                 540

Asp His Val Leu Pro Ile Asp Tyr Tyr Phe Pro Pro Gln Lys Thr Cys
545                 550                 555                 560

Leu Ile Cys Gly Asp Glu Ala Ser Gly Cys His Tyr Gly Ala Leu Thr
                565                 570                 575

Cys Gly Ser Cys Lys Val Phe Phe Lys Arg Ala Ala Glu Gly Lys Gln
            580                 585                 590

Lys Tyr Leu Cys Ala Ser Arg Asn Asp Cys Thr Ile Asp Lys Phe Arg
            595                 600                 605

Arg Lys Asn Cys Pro Ser Cys Arg Leu Arg Lys Cys Tyr Glu Ala Gly
            610                 615                 620

Met Thr Leu Gly Ala Arg Lys Leu Lys Lys Leu Gly Asn Leu Lys Leu
625                 630                 635                 640
```

Gln Glu Glu Gly Glu Ala Ser Ser Thr Thr Ser Pro Thr Glu Glu Thr
             645                 650                 655

Thr Gln Lys Leu Thr Val Ser His Ile Glu Gly Tyr Glu Cys Gln Pro
         660                 665                 670

Ile Phe Leu Asn Val Leu Glu Ala Ile Glu Pro Gly Val Val Cys Ala
         675                 680                 685

Gly His Asp Asn Asn Gln Pro Asp Ser Phe Ala Ala Leu Leu Ser Ser
         690                 695                 700

Leu Asn Glu Leu Gly Glu Arg Gln Leu Val His Val Val Lys Trp Ala
705                 710                 715                 720

Lys Ala Leu Pro Gly Phe Arg Asn Leu His Val Asp Asp Gln Met Ala
                 725                 730                 735

Val Ile Gln Tyr Ser Trp Met Gly Leu Met Val Phe Ala Met Gly Trp
             740                 745                 750

Arg Ser Phe Thr Asn Val Asn Ser Arg Met Leu Tyr Phe Ala Pro Asp
         755                 760                 765

Leu Val Phe Asn Glu Tyr Arg Met His Lys Ser Arg Met Tyr Ser Gln
770                 775                 780

Cys Val Arg Met Arg His Leu Ser Gln Glu Phe Gly Trp Leu Gln Ile
785                 790                 795                 800

Thr Pro Gln Glu Phe Leu Cys Met Lys Ala Leu Leu Leu Phe Ser Ile
                 805                 810                 815

Ile Pro Val Asp Gly Leu Lys Asn Gln Lys Phe Phe Asp Glu Leu Arg
             820                 825                 830

Met Asn Tyr Ile Lys Glu Leu Asp Arg Ile Ile Ala Cys Lys Arg Lys
         835                 840                 845

Asn Pro Thr Ser Cys Ser Arg Arg Phe Tyr Gln Leu Thr Lys Leu Leu
850                 855                 860

Asp Ser Val Gln Pro Ile Ala Arg Glu Leu His Gln Phe Thr Phe Asp
865                 870                 875                 880

Leu Leu Ile Lys Ser His Met Val Ser Val Asp Phe Pro Glu Met Met
                 885                 890                 895

Ala Glu Ile Ile Ser Val Gln Val Pro Lys Ile Leu Ser Gly Lys Val
             900                 905                 910

Lys Pro Ile Tyr Phe His Thr Gln
         915                 920

<210> SEQ ID NO 36
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Met Thr Leu Gly Glu Lys Phe Arg Val Gly Asn Cys Lys His Leu Lys
1               5                   10                  15

Met Thr Arg Pro
            20

<210> SEQ ID NO 37
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
tgtcactatg gagctctcac atgtgg                                          26

<210> SEQ ID NO 38
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
cattgtggcc aacatgacac ttca                                            24

<210> SEQ ID NO 39
<211> LENGTH: 1290
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
tgtcactatg gagctctcac atgtggaagc tgcaaggtct tcttcaaaag agccgctgaa     60
gggaaacaga agtacctgtg cgccagcaga aatgattgca ctattgataa attccgaagg   120
aaaaattgtc catcttgtcg tcttcggaaa tgttatgaag cagggatgac tctgggagac   180
aacttacctg agcaagctgc tttttggaga catttgcaca tcttttggga tcacgttgtt   240
aagaagtaga actaagggaa aaacacgcag ccacccagaa atcggtagag ccttcagctc   300
atctgttatt aatatttctg tgacaacaga tatctaggaa gtaaacagga aattgcatcg   360
ctatcctgca tcacctttt tggaatcagg ttccattctt ctcagtccag ttcaaccttg   420
tgatactttt tagatctcaa ccaaggcata gaaatatatt tcccttgct taataccca    480 tggaaccaat gcccctgtgg ttgaagtaaa aattgattgt tgagggacat ttcagccctc   540
tagcagtcaa caattaaaaa catgtaagca ccgagcacct gcagaaaact tggactggca   600
tttggatcta agaagaaaat ctgcatcttg accaagatga aaagtcacca gcccaagctt   660
gtgcagtgaa gtgtcatgtt ggccacaatg aaactgaaag agactgatga ctctcctcag   720
ggtggaaaat gaggcatgga agctttgatt agtgagctgt taggcacaca gacattaatt   780
tcaaagcatt ctcatctcca gtctgagtaa taatgcttat agtattatgc aattgtttgg   840
ctgctgcaag aaattcagca gactccaaca agtagtcttt cttggtctct gagtgactgt   900
aacttaaatt ctacctccct tctcttctcc tacatcttct cactcccac cccacccca    960 catacacaca attcttgtcc actatgttca gagagatgca cgcacacata tatatgtata  1020
tatatagtat atttgtcaat aaagcagaaa agaagaaaaa actccaagta aacaattttc  1080
catttcccca tctcacttct gtcttacaag tggataggaa aagaaaaacc cccagtaaaa  1140
aatggcaacc gcccacctcc ccaactttac atgctgcttc ctatgttaga ggatctgtct  1200
taggcatctg attatggagc ctgctagata caagcccgta tttagactgc tacagtcaac  1260
aatgtctctc tttcatacta gaaaaattcc                                   1290

<210> SEQ ID NO 40
<211> LENGTH: 82
<212> TYPE: PRT
<213> ORGANISM: Artificial Sequence
<220> FEATURE:

```
<223> OTHER INFORMATION: Description of Artificial Sequence: Synthetic
      polypeptide

<400> SEQUENCE: 40

Cys His Tyr Gly Ala Leu Thr Cys Gly Ser Cys Lys Val Phe Phe Lys
1               5                   10                  15

Arg Ala Ala Glu Gly Lys Gln Lys Tyr Leu Cys Ala Ser Arg Asn Asp
                20                  25                  30

Cys Thr Ile Asp Lys Phe Arg Arg Lys Asn Cys Pro Ser Cys Arg Leu
            35                  40                  45

Arg Lys Cys Tyr Glu Ala Gly Met Thr Leu Gly Asp Asn Leu Pro Glu
        50                  55                  60

Gln Ala Ala Phe Trp Arg His Leu His Ile Phe Trp Asp His Val Val
65                  70                  75                  80

Lys Lys

<210> SEQ ID NO 41
<211> LENGTH: 19
<212> TYPE: RNA
<213> ORGANISM: Homo sapiens

<400> SEQUENCE: 41
ucaaggaacu cgaucguau                                              19

<210> SEQ ID NO 42
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
guaguuguga guaucauga                                              19

<210> SEQ ID NO 43
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Met Thr Leu Gly Ala Val Val Ser Glu Arg Ile Leu Arg Val Phe
1               5                   10                  15

Gly Val Ser Glu Trp Leu Pro
                20

<210> SEQ ID NO 44
<211> LENGTH: 57
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Arg Ala Ala Glu Gly Phe Phe Arg Met Asn Lys Leu Lys Glu Ser Ser
1               5                   10                  15

Asp Thr Asn Pro Lys Pro Tyr Cys Met Ala Ala Pro Met Gly Leu Thr
                20                  25                  30
```

```
Glu Asn Asn Arg Asn Arg Lys Lys Ser Tyr Arg Glu Thr Asn Leu Lys
        35                  40                  45

Ala Val Ser Trp Pro Leu Asn His Thr
    50                  55

<210> SEQ ID NO 45
<211> LENGTH: 57
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Met Thr Leu Gly Gly Phe Phe Arg Met Asn Lys Leu Lys Glu Ser Ser
1               5                   10                  15

Asp Thr Asn Pro Lys Pro Tyr Cys Met Ala Ala Pro Met Gly Leu Thr
            20                  25                  30

Glu Asn Asn Arg Asn Arg Lys Lys Ser Tyr Arg Glu Thr Asn Leu Lys
        35                  40                  45

Ala Val Ser Trp Pro Leu Asn His Thr
    50                  55

<210> SEQ ID NO 46
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Met Thr Leu Gly Asp
1               5

<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Met Thr Leu Gly Ala Gly Ser Arg Val Ser
1               5                   10
```

COMPOSITIONS AND METHODS FOR TREATING OR PREVENTING PROSTATE CANCER AND FOR DETECTING ANDROGEN RECEPTOR VARIANTS

RELATED APPLICATIONS/PATENTS & INCORPORATION BY REFERENCE

This application is a continuation of and claims priority to U.S. patent application Ser. No. 12/988,299, filed on Oct. 15, 2010, which is a National Stage Application of PCT/US2009/02392, filed on Apr. 16, 2009, which claims the benefit of U.S. Provisional Application No. 61/124,328, filed on Apr. 16, 2008 and U.S. Provisional Application No. 61/114,153, filed on Nov. 13, 2008. The entire contents of the aforementioned applications are hereby incorporated by reference.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. More generally, documents or references are cited in this text, either in a Reference List before the claims, or in the text itself; and, each of these documents or references ("herein-cited references"), as well as each document or reference cited in each of the herein-cited references (including any manufacturer's specifications, instructions, etc.), is hereby expressly incorporated herein by reference.

SEQUENCE LISTING

The present application contains a sequence listing that has been submitted in ASCII format via EFS-Web on Aug. 3, 2015, containing the file name SL 36406.0009 U2-, which is 40,635 bytes in size, created on Jul. 23, 2015, comprises 47 sequences, and is herein incorporated by reference in its entirety.

BACKGROUND OF THE INVENTION

Prostate cancer (PCa) depends on androgenic signaling for growth and survival. Androgens exert their cellular and physiologic effects through binding to the androgen receptor (AR), a member of the steroid hormone receptor family of transcription factors. The human AR gene is located on chromosome Xq11-12 and spans approximately 180 kb of DNA with eight known exons. The prototype AR protein contains several functional domains. The NH2-terminal domain (NTD), encoded by exon 1, constitutes approximately 60% of the 110-kDa full-length protein and is the transcriptional regulatory region of the protein. The central DNA-binding domain (DBD) is encoded by exons 2 and 3, whereas exons 4 to 8 code for the COOH-terminal ligand-binding domain (LBD). Androgen binding to the AR LBD allows entry of the ligand-bound receptor into the nucleus and subsequent transcriptional regulation of androgen-responsive genes.

Hormonal therapy has been used since 1941 for the treatment of metastatic prostate cancer. Hormone deprivation therapies employing surgical and/or medical castration as well as their combination with anti-androgens have since become the mainstay of systemic treatment for advanced prostate cancer. Hormonal therapies for advanced PCa target AR-mediated functions by suppressing the production of androgens and/or androgen binding to the AR LBD. Although these therapies often result in a period of clinical regression, they are not curative due to progression to hormone-refractory PCa (HRPC) for which effective therapeutic options are limited. In a contemporary clinical setting, the length of clinical remission, often assessed by serum prostate-specific antigen (PSA) measurements, varies substantially due to a wide spectrum of clinical phenotypes among treated patients. Almost invariably, however, prostate cancer develops castration-resistant phenotype and progresses to a life-threatening stage, despite hormone therapies. The widespread use of hormone deprivation therapies is manifested in the observation that almost all patients who die from prostate cancer had received and failed hormone-deprivation therapies.

A few lines of evidence have established that, unlike human breast cancer, prostate cancer progression upon hormone therapy is not due to loss of dependence on hormonal signaling but, instead, characterized by sustained androgenic signaling that bypasses the requirement for physiological levels of androgens. First, with only certain exceptions, prostate cancer patients dying from castration-resistant prostate cancer have very high levels of serum PSA, the production of which is driven by androgenic signaling. Second, castration-resistant prostate cancers have elevated expression levels of the key mediator of androgenic signaling, the AR, and this is a very consistent molecular feature in tissues derived from patients with castration-resistant prostate cancer. Third, a subset of prostate cancers that relapsed following hormone therapy continue to respond to second-line hormone therapies designed to disrupt the AR signaling axis, suggesting that AR-mediated androgenic signaling is still operating among these tumors. While it is possible that AR-negative prostate cancer cells may give rise to androgen-independent prostate carcinoma, prostate tumors comprised of mainly AR-negative malignant cells (i.e., small cells and neuroendocrine cells) are rare.

AR-mediated functions are not completely abrogated by the existing hormone therapies. HRPC continues to depend on AR-mediated functions but bypasses the requirement for physiologic levels of androgens. Molecular alterations involving AR itself, such as AR overexpression and gain-of-function AR LBD mutations, are common in HRPC and allow for continued AR-mediated genomic functions under the presence of reduced or altered ligands. Despite the established clinical relevance of these well-characterized AR alterations in HRPC, only a few previous studies have suggested an alternative mechanism for HRPC and investigated the putative role of AR variants lacking the AR LBD.

Accordingly, a need remains to for more effective compositions and methods for the treatment of prostate cancer.

SUMMARY OF THE INVENTION

Included in the present invention are a number of novel AR variants. These novel AR variants are encoded by spliced transcripts and do not have the protein domains needed to bind to androgens but are constitutively active and drive AR signaling in the complete absence of androgens. The present inventors have performed a comprehensive in silico sequence analysis and tiling expression microarray analysis of the human AR genomic locus and uncovered multiple novel ARDLBD variants with intact coding potential for the full AR NTD and AR DBD. The present inventors have shown that an antibody generated against one of the AR variants detects AR variant protein frequently in HRPC specimens. Accordingly, the expression pattern and the validated androgen-independent function of these newly identified AR variants contribute a new understanding to the molecular mechanism of HRPC that will affect the overall management of patients with advanced PCa.

In one aspect, the invention features a method of determining if a subject will respond to androgen therapy, the method comprising determining the level of expression or biological activity of an androgen receptor variant polypeptide in a subject sample wherein an alteration in the level of expression or biological activity relative to the expression or biological activity in a reference indicates that the subject will respond to androgen therapy.

In another aspect, the invention features a method of determining if a subject will respond to androgen therapy, the method comprising determining the level of expression or biological activity of an androgen receptor variant nucleic acid in a subject sample wherein an alteration in the level of expression relative to the expression in a reference indicates that the subject will respond to androgen therapy.

In one embodiment, the subject is has or has a propensity to develop prostate cancer.

In one aspect, the present invention provides a method of diagnosing a subject as having, or having a propensity to develop prostate cancer, the method comprising determining the level of expression of an androgen receptor variant nucleic acid in a subject sample wherein an alteration in the level of expression relative to the expression in a reference indicates that the subject has or has a propensity to develop an androgen related disease or disorder. In one aspect, the present invention provides a method of diagnosing a subject as having, or having a propensity to develop prostate cancer, the method comprising determining the level of expression or biological activity of an androgen receptor variant polypeptide in a subject sample wherein an alteration in the level of expression or biological activity relative to the expression or biological activity in a reference indicates that the subject has or has a propensity to develop an androgen related disease or disorder.

In another aspect, the invention provides a method of determining the risk of recurrence of prostate cancer, the method comprising determining the level of expression of an androgen receptor variant nucleic acid molecule in a subject sample, wherein an increased level of expression relative to a reference indicates that the subject has an increased risk of recurrence of an androgen related disease or disorder.

In still another aspect, the invention provides a method of determining the risk of recurrence of prostate cancer in a subject, the method comprising determining the level of expression or activity of an androgen receptor variant polypeptide in a subject sample, wherein an increased level of expression or activity relative to the level of expression or activity in a reference indicates that the subject has an increased risk of recurrence of an androgen related disease or disorder.

In another aspect, the invention provides a method of monitoring a subject diagnosed as having prostate cancer, the method comprising determining the expression of an androgen receptor variant nucleic acid molecule in a subject sample, wherein an alteration in the level of expression relative to the level of expression in a reference indicates the severity of the disease or disorder in the subject.

In still another aspect, the invention provides a method of monitoring a subject diagnosed as having prostate cancer, the method comprising determining the level of expression or activity of an androgen receptor variant polypeptide in a subject sample, wherein an alteration in the level of expression or activity relative to the level of activity in a reference indicates the severity of the androgen related disease or disorder in the subject.

In another aspect, the invention provides a method of determining the progression of prostate cancer in a subject, the method comprising determining the expression of an androgen receptor variant nucleic acid molecule in a subject sample, wherein an alteration in the level of expression relative to the level of expression in a reference indicates the progression of the disease or disorder in the subject.

In another aspect, the invention provides a method of diagnosing a subject as having, or having a propensity to develop, an androgen related disease or disorder, the method comprising determining the level of expression of an androgen receptor variant nucleic acid molecule in a subject sample, wherein an increased level of expression relative to a reference indicates that the subject has or has a propensity to develop an androgen related disease or disorder.

In still another aspect, the invention provides a method of diagnosing a subject as having, or having a propensity to develop, an androgen related disease or disorder, the method comprising determining the level of expression of an androgen receptor variant polypeptide in a subject sample, wherein an increased level of expression relative to the level of expression in a reference indicates that the subject has or has a propensity to develop an androgen related disease or disorder.

In one embodiment of any one of the above aspects, the level of expression is determined in an immunological assay.

In one embodiment of any one of the methods described herein, the method is used to determine if a subject will be responsive to androgen therapy.

In another embodiment of any one of the above aspects, the subject is being treated for an androgen related disease or disorder.

In another embodiment of any one of the above aspects, the alteration is an increase. In a related embodiment, the increase corresponds to a failure to respond to androgen therapy.

In another embodiment of any one of the above aspects, the reference is a control subject sample.

In another embodiment of any one of the above aspects, the reference is a subject sample obtained at an earlier time point.

In yet another embodiment of any one of the above aspects, the reference is a subject sample obtained before surgical treatment.

In another embodiment, the reference is the level of androgen receptor variant polypeptide or nucleic acid molecule present in a control sample obtained from subjects with a disease of a lesser severity. In a related embodiment, the disease of lesser severity is an early stage non-aggressive prostate cancer.

In another embodiment of any one of the above aspects, the subject sample is a biological sample.

In another embodiment of any one of the above aspects, the method is used to diagnose a subject as having prostate cancer.

In another embodiment of any one of the above aspects, the method is used to determine the treatment regimen for a subject having prostate cancer.

In another embodiment of any one of the above aspects, the method is used to monitor the condition of a subject being treated for prostate cancer.

In another embodiment of any one of the above aspects, the method is used to determine the prognosis of a subject having prostate cancer. In still another embodiment of any one of the above aspects, the method is used to determine the prognosis of a subject following androgen therapy. In a related embodiment, a poor prognosis determines an aggressive treatment regimen for the subject.

In another embodiment of any one of the above aspects, the method further comprises obtaining a biological sample from the subject.

In another related embodiment, the androgen related disease or disorder is selected from the group consisting of: prostate cancer, androgenic alopecia, infertility, irregular menstrual periods, excessive hair growth, acne, obesity, insulin resistance, and polycystic ovarian syndrome.

In a further embodiment, the androgen related disease or disorder is prostate cancer.

In another embodiment of any one of the above aspects, the prostate cancer is hormone refractory prostate cancer.

In another embodiment of any one of the above aspects, the prostate cancer is hormone naïve prostate cancer.

In another embodiment of any one of the above aspects, the expression of an androgen receptor variant nucleic acid molecule detected using a hybridization reaction comprising hybridizing the sample to one or more primer sets.

In one embodiment, the hybridization reaction is a polymerase chain reaction. In another embodiment, each primer set comprises a forward primer and a reverse primer, wherein the forward primer is complementary to a nucleic acid sequence corresponding to a nucleic acid sequence selected from SEQ ID NOs 1-7, or SEQ ID NO: 39 or fragments thereof, and the reverse primer is reverse complementary to a nucleic acid sequence corresponding to a nucleic acid sequence selected from SEQ ID NOs 1-7 or SEQ ID NO: 39.

In a related embodiment, the primer set is selected from the group consisting of: (P1): TGTCACTATGGAGCTCTCACATGTGG (SEQ ID NO: 15) and CACCTCTCAAATATGCTAGACGAATCTGT (SEQ ID NO: 16); (P2) TGTCACTATGGAGCTCTCACATGTGG (SEQ ID NO: 17) and GTACTCATTCAAGTATCAGATATGCGGTATCAT (SEQ ID NO: 18); (P3) TGTCACTATGGAGCTCTCACATGTGG (SEQ ID NO: 19) and CTGTGGATCAGCTACTACCTTCAGCTC (SEQ ID NO: 20); (P4) GTTGCTCCCGCAAGTTTCCTTCTC (SEQ ID NO: 21) and CTGTTGTGGATGAGCAGCTGAGAGTCT (SEQ ID NO: 22); (P5) GTTGCTCCCGCAAGTTTCCTTCTC (SEQ ID NO: 23) and TTTGAATGAGGCAAGTCAGCCTTTCT (SEQ ID NO: 24); (P6) CCATCTTGTCGTCTTCGGAAATGT TATGAAGC (SEQ ID NO: 25) and CTGTTGTGGATGAGCAGCTGAGAGTCT (SEQ ID NO: 26); (P7) CCATCTTGTCGTCTTCGGAAATGTT ATGAAGC (SEQ ID NO: 27) and TTTGAATGAGGCAAGTCAGCCTTTCT (SEQ ID NO: 28); (P8) CCATCTTGTCGTCTTCGGAAATG TTATGAAGC (SEQ ID NO: 29) and AGCTTCTGGGTTGTCTCCTCAGTGG (SEQ ID NO: 30); (P9)-Tgtcactatggagctctcacatgtgg (SEQ ID NO: 37) and Cattgtggccaacatgacacttca (SEQ ID NO: 38).

In another aspect, the invention features a method for identifying a subject as having or having a propensity to develop prostate cancer, the method comprising detecting an alteration in the sequence of an androgen receptor nucleic acid molecule relative to the sequence or expression of a reference molecule.

In one embodiment, the alteration is detected using a hybridization reaction comprising hybridizing the sample to one or more primer sets. In a related embodiment, the hybridization reaction is a polymerase chain reaction. In a further related embodiment, the primer sets are selected from the group consisting of: (P1): TGTCACTATGGAGCTCTCACATGTGG (SEQ ID NO: 15) and CACCTCTCAAATATGCTAGACGAATCTGT (SEQ ID NO: 16); (P2) TGTCACTATGGAGCTCTCACATGTGG (SEQ ID NO: 17) and GTACTCATTCAAGTATCAGATATGCGGTATCAT (SEQ ID NO: 18); (P3) TGTCACTATGGAGCTCTCACATGTGG (SEQ ID NO: 19) and CTGTGGATCAGCTACTACCTTCAGCTC (SEQ ID NO: 20); (P4) GTTGCTCCCGCAAGTTTCCTTCTC (SEQ ID NO: 21) and CTGTTGTGGATGAGCAGCTGAGAGTCT (SEQ ID NO: 22); (P5) GTTGCTCCCGCAAGTTTCCTTCTC (SEQ ID NO: 23) and TTTGAATGAGGCAAGTCAGCCTTTCT (SEQ ID NO: 24); (P6) CCATCTTGTCGTCTTCGGAAATGT TATGAAGC (SEQ ID NO: 25) and CTGTTGTGGATGAGCAGCTGAGAGTCT (SEQ ID NO: 26); (P7) CCATCTTGTCGTCTTCGGAAATGTT ATGAAGC (SEQ ID NO: 27) and TTTGAATGAGGCAAGTCAGCCTTTCT (SEQ ID NO: 28); (P8) CCATCTTGTCGTCTTCGGAAATG TTATGAAGC (SEQ ID NO: 29) and AGCTTCTGGGTTGTCTCCTCAGTGG (SEQ ID NO: 30); (P9) Tgtcactatggagctctcacatgtgg (SEQ ID NO: 37) and Cattgtggccaacatgacacttca (SEQ ID NO: 38).

In another aspect, the invention features an androgen receptor variant antibody that specifically binds to an androgen receptor variant (AR-V) protein or fragment thereof.

In one embodiment, the antibody specifically binds to an androgen receptor variant-7 (AR-V7) protein.

In one embodiment, the antibody specifically binds to an androgen receptor variant-8 (AR-V8) protein.

In another embodiment, the antibody specifically binds to an androgen receptor variant-1 (AR-V 1) protein.

In still another further embodiment, the antibody binds to a CKHLKMRP epitope of an AR-V polypeptide, corresponding to SEQ ID NO: 33.

In another embodiment of any one of the above aspects, the antibody is monoclonal.

In another aspect, the invention features a polypeptide comprising an isolated androgen receptor protein variant, or fragment thereof, having substantial identity to androgen receptor variant 1, 2, 3, 4, 5, 6, 7 or 8 (AR-V1-AR-V8), wherein the variant is upregulated in prostate cancer.

In one embodiment, the androgen receptor protein variant is at least 85% identical to androgen receptor variant 1, 2, 3, 4, 5, 6, 7 or 8.

In another embodiment, the androgen receptor protein variant comprises at least the androgen receptor NH2 terminal domain (NTD) and DNA binding domain (DBD).

In another related embodiment, the polypeptide is linked to a detectable amino acid sequence.

In still another related embodiment, the polypeptide is linked to an affinity tag.

In another embodiment of the above aspects, the nucleic acid molecule encodes a polypeptide of any one of the above.

In another embodiment, the invention features a vector comprising the nucleic acid molecule of any one of the above aspects.

In another aspect, the invention features an isolated androgen receptor variant inhibitory nucleic acid molecule, wherein the inhibitory nucleic acid molecule specifically binds at least a fragment of a nucleic acid molecule encoding an androgen receptor variant protein.

In one embodiment, the vector comprises a nucleic acid molecule encoding the nucleic acid molecule of the above aspects.

In another embodiment, the vector is an expression vector.

In still another embodiment, the nucleic acid molecule is operably linked to a promoter.

In still another embodiment, the promoter is suitable for expression in a mammalian cell.

In another embodiment, the invention features a host cell comprising a nucleic acid molecule of any one of the above aspects.

In one embodiment, the cell expresses an androgen receptor variant protein.

In another embodiment, the cell is in vitro. In another embodiment, the cell is in vivo.

In still another embodiment, the cell is a mammalian cell. In still another embodiment, the cell is a human cell.

In another aspect, the invention features a double-stranded RNA corresponding to at least a portion of an androgen receptor variant nucleic acid molecule that encodes an androgen receptor variant protein, wherein the double-stranded RNA is capable of altering the level of protein encoded by the androgen receptor variant nucleic acid molecule.

In one embodiment, the RNA is an siRNA.

In another aspect, the invention features an antisense nucleic acid molecule, wherein the antisense nucleic acid molecule is complementary to an androgen receptor variant nucleic acid molecule that encodes an androgen receptor variant protein, and wherein the antisense is capable of altering expression from the nucleic acid molecule to which it is complementary.

In another aspect, the invention features a primer capable of binding to an androgen receptor variant nucleic acid molecule encoding an androgen receptor variant protein variant.

In one embodiment, the primer is capable of binding to an androgen receptor variant nucleic acid molecule, wherein the primer is selected from the group consisting of: (SEQ ID NO: 15), (SEQ ID NO: 16), (SEQ ID NO: 17), (SEQ ID NO: 18), (SEQ ID NO: 19), (SEQ ID NO: 20), (SEQ ID NO: 21), (SEQ ID NO: 22), (SEQ ID NO: 23), (SEQ ID NO: 24), (SEQ ID NO: 25), (SEQ ID NO: 26), (SEQ ID NO: 27), (SEQ ID NO: 28), (SEQ ID NO: 29), (SEQ ID NO: 30), (SEQ ID NO: 37) and (SEQ ID NO: 38).

In another aspect, the invention features an androgen receptor biomarker purified on a biochip.

In another aspect, the invention features a microarray comprising at least two nucleic acid molecules, or fragments thereof, fixed to a solid support, wherein at least one of the nucleic acid molecules is an androgen receptor variant nucleic acid molecule.

In another aspect, the invention features a microarray comprising at least two polypeptides, or fragments thereof, bound to a solid support, wherein at least one of the polypeptides on the support is an androgen receptor variant polypeptide.

In another aspect, the invention features a kit for the diagnosis of prostate cancer in a subject comprising a primer set that detects an androgen receptor variant nucleic acid molecule, or fragment thereof, and written instructions for use of the kit for detection of prostate cancer.

In another aspect the invention features a diagnostic kit for the diagnosis of an androgen related disease or disorder in a subject comprising a primer set that detects an androgen receptor variant nucleic acid molecule, or fragment thereof, and written instructions for use of the kit for detection of an androgen related disease or disorder.

In still another aspect, the invention features a diagnostic kit for the diagnosis of prostate cancer in a subject comprising an antibody that specifically binds an androgen receptor variant polypeptide, or fragment thereof, and written instructions for use of the kit for detection of prostate cancer.

In another aspect, the invention features a kit identifying a subject as having or having a propensity to develop prostate cancer, comprising an adsorbent, wherein the adsorbent retains an androgen receptor variant biomarker, and written instructions for use of the kit for detection of prostate cancer.

In another aspect, the invention features a kit for determining if a subject will respond to androgen therapy, the kit comprising a primer set to detect an androgen receptor variant nucleic acid molecule, or fragment thereof, and written instructions for use of the kit for determining if a subject will respond to androgen therapy.

In still another aspect, the invention features a kit for determining if a subject will respond to androgen therapy, the kit comprising an antibody that specifically binds an androgen receptor variant polypeptide, or fragment thereof, and written instructions for use of the kit for determining if a subject will respond to androgen therapy.

In another aspect, the invention features a method of altering the expression of an androgen receptor variant nucleic acid molecule in a cell, the method comprising contacting the cell with an effective amount of a compound capable of altering the expression of the androgen receptor variant nucleic acid molecule.

In one embodiment, the compound is an antisense nucleic acid molecule, a small interfering RNA (siRNA), or a double stranded RNA (dsRNA) that inhibits the expression of an androgen receptor variant nucleic acid molecule.

In one aspect, the invention features a method of altering androgen receptor variant protein expression in a cell, the method comprising contacting the cell with a compound capable of altering the expression of an androgen receptor variant polypeptide.

In another aspect, the invention features a method of treating or preventing prostate cancer, the method comprising administering to a subject in need thereof an effective amount of a pharmaceutical composition that alters expression of an androgen receptor variant polypeptide.

In still another aspect, the invention features a method of identifying a compound that inhibits prostate cancer the method comprising contacting a cell that expresses an androgen receptor variant nucleic acid molecule with a candidate compound, and comparing the level of expression of the nucleic acid molecule in the cell contacted by the candidate compound with the level of expression in a control cell not contacted by the candidate compound, wherein an alteration in expression of the androgen receptor variant nucleic acid molecule identifies the candidate compound as a compound that inhibits prostate cancer.

In one embodiment, the alteration in expression is a decrease in transcription.

In another embodiment, the alteration in expression is a decrease in translation.

Aspect, the invention features a method of identifying a compound that inhibits prostate cancer, the method comprising contacting a cell that expresses an androgen receptor variant polypeptide with a candidate compound, and comparing the level of expression of the polypeptide in the cell contacted by the candidate compound with the level of polypeptide expression in a control cell not contacted by the candidate compound, wherein an alteration in the expression of the androgen receptor variant polypeptide identifies the candidate compound as a compound that inhibits prostate cancer.

In still another aspect, the invention features a method of identifying a compound that inhibits prostate cancer, the method comprising contacting a cell that expresses an androgen receptor variant polypeptide with a candidate compound, and comparing the biological activity of the polypeptide in the cell contacted by the candidate compound with the level of biological activity in a control cell not contacted by the candidate compound, wherein an alteration in the biological activity of the androgen receptor variant polypeptide identifies the candidate compound as a candidate compound that inhibits prostate cancer.

In one embodiment of the above aspects, the cell is a human cell. In another embodiment of the above aspects, the cell is a neoplastic cell.

In another embodiment of the above aspects, the cell is in vitro. In another embodiment of the above aspects, the cell is in vivo.

In still another embodiment of the above aspects, the alteration in expression is assayed using an immunological assay, an enzymatic assay, or a radioimmunoassay.

In one embodiment, the androgen receptor variant polypeptide comprises a sequence selected from the group consisting of: SEQ ID NO: 8, SEQ ID NO: 9, SEQ ID NO: 10, SEQ ID NO: 11, SEQ ID NO: 12, SEQ ID NO: 13, SEQ ID NO: 14, and SEQ ID NO: 40 or fragments thereof.

In one embodiment of any one of the above aspects, the androgen receptor variant polypeptide comprises SEQ ID NO: 8, or a fragment thereof. In still another embodiment, the androgen receptor variant polypeptide comprises SEQ ID NO: 9, or a fragment thereof. In still another embodiment, the androgen receptor variant polypeptide comprises SEQ ID NO: 40, or a fragment thereof.

In one embodiment of any one of the above aspects, the androgen receptor variant nucleic acid comprises a sequence selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7 and SEQ ID NO: 39 or fragments thereof.

In another embodiment, the androgen receptor variant nucleic acid comprises SEQ ID NO: 1, or a fragment thereof. In still another embodiment, the androgen receptor variant nucleic acid comprises SEQ ID NO: 2. In still another embodiment, the androgen receptor variant nucleic acid comprises SEQ ID NO: 39.

In another embodiment of any one of the above aspects, the prostate cancer is hormone refractory prostate cancer. In another embodiment of any one of the above aspects, the prostate cancer is hormone naive prostate cancer.

In another embodiment of any one of the above aspects, SEQ ID NO: 1-SEQ ID NO: 7 and SEQ ID NO: 39 can correspond to a nucleic acid sequence, or fragment thereof, and SEQ ID NO: 8-SEQ ID NO: 15 and SEQ ID NO: 40 can correspond to an amino acid sequence, or fragment thereof, as follows:

SEQ ID NO: 1

```
TGTCACTATGGAGCTCTCACATGTGGAAGCTGCAAGGTCTTCTTCAAAAGAGCCG

CTGAAGGGAAACAGAAGTACCTGTGCGCCAGCAGAAATGATTGCACTATTGATA

AATTCCGAAGGAAAAATTGTCCATCTTGTCGTCTTCGGAAATGTTATGAAGCAGG

GATGACTCTGGGAAAAAATTCCGGGTTGGCAATTGCAAGCATCTCAAAATGAC

CAGACCCTGAAGAAAGGCTGACTTGCCTCATTCAAAATGAGGGCTCTAGAGGGC

TCTAGTGGATAGTCTGGAGAAACCTGGCGTCTGAGGCTTAGGAGCTTAGGTTTTT

GCTCCTCAACACAGACTTTGACGTTGGGGTTGGGGGCTACTCTCTTGATTGCTGA

CTCCCTCCAGCGGGACCAATAGTGTTTTCCTACCTCACAGGGATGTTGTGAGGAC

GGGCTGTAGAAGTAATAGTGGTTACCACTCATGTAGTTGTGAGTATCATGATTAT

TGTTTCCTGTAATGTGGCTTGGCATTGGCAAAGTGCTTTTTGATTGTTCTTGATCA

CATATGATGGGGCCAGGCACTGACTCAGGCGGATGCAGTGAAGCTCTGGCTCA

GTCGCTTGCTITICGTGGTGTGCTGCCAGGAAGAAACTTTGCTGATGGGACTCAA

GGTGTCACCTTGGACAAGAAGCAACTGTGTCTGTCTGAGGTTCCTGTGGCCATCT

TTATTTGTGTATTAGGCAATTCGTATTTCCCCCTTAGGTTCTAGCCTTCTGGATCC

CAGCCAGTGACCTAGATCTTAGCCTCAGGCCCTGTCACTGAGCTGAAGGTAGTAG

CTGATCCACAGAAGTTCAGTAAACAAGGACCAGATTTCTGCTTCTCCAGGAGAA

GAAGCCAGCCAACCCCTCTCTTCAAACACACTGAGAGACTACAGTCCGACTTTCC

CTCTTACATCTAGCCTTACTGTAGCCACACTCCTTGATTGCTCTCTCACATCACAT

GCTTCTCTTCATCAGTTGTAAGCCTCTCATTCTTCTCCCAAGCCAGACTCAAATAT

TGTATTGATGTCAAAGAAGAATCACTTAGAGTTTGGAATATCTTGTTCTCTCTCG

CTCCATAGCTTCCATATTGACACCAGTTTCTTTCTAGTGGAGAAGTGGAGTCTGT

GAAGCCAGGGAAACACACATGTGAGAGTCAGAAGGACTCTCCC
```

SEQ ID NO: 2

<u>TGTCACTATGGAGCTCTCACATGTGG</u>AAGCTGCAAGGTC'TTCTTCAAAAGAGCCG
CTGAAGGGAAACAGAAGTACCTGTGCGCCAGCAGAAATGATTGCACTATTGATA
AATTCCGAAGGAAAAATTGTCCATCTTGTCGTCTTCGGAAATGTTATGAAGCAGG
GATGACTCTGGGA*CTGTTGTTGTTTCTGAAAGAATCTTGAGGGTGTTTGGAGTC
TCAGAATGGCTTCCTTAAAGACTACCTTCAGACTCTCAGCTGCTCATCCACAACA
GAGATCAGCCTTTCTTTGTAGATGATTCATTCCTGGCTGCATTTGAAAACCACAT
ATTGTTAATTGCTTGACGAATTTAAATCCCTTGACTACTTTTCATTTCAGAAAACA
CTTACAAAAAAGTCCAAATGAGGACCTTCCCTCCAGTGAATTAGCTGTGGCTTT
CTCACAGTCCATAGTTAGGATAAATGTAAAGCCATTTCTCATTTTTCTCCGCACTT
TCCAAGGGTACACTCCTTGTTTCCAAGATGGAATGAGAAATAAAGAAGTGCCCTT
CCTGCCATCTTCTCCCCTGACCCTTTCCTCCTTCCCACTTTCCTCCTATTCCTCCCC
AAACATGATTTATTTCTGCGTTTTGCAACTCTTGAGTTCTCAGCATTTAGTAAATG
GTGTTGGTCCCTGTTGATTCCTTCCTCTCCTGGACCATGGAAGGTAGTAGGCCTTT
CAGAAATTTCAGGTAGCAGCCAAACCCCAGAAGAAGAGAAGGAACACAGAGAC
CTAGACCATGTGAGAACCTGAGGTGTGCAGCATTTACTTC<u>ACAGATTCGTCTAGC
ATATTTGAGAGGTG</u>

SEQ ID NO: 3

<u>TGTCACTATGGAGCTCTCACATGTGG</u>AAGCTGCAAGGTCTTCTTCAAAAGAGCCG
CTGAAGGGAAACAGAAGTACCTGTGCGCCAGCAGAAATGATTGCACTATTGATA
AATTCCGAAGGAAAAATTGTCCATCTTGTCGTCTTCGGAAATGTTATGAAGCAGG
GATGACTCTGGGAGGGAAACAGAAGTACCTGTGCGCCAGCAGAAATGATTGCAC
TATTGATAAATTCCGAAGGAAAAATTGTCCATCTTGTCGTCTTCGGAAATGTTAT
GAAGCAGGGATGACTCTGGGA*CTGTTGTTGTTTCTGAAAGAATCTTGAGGGTGT
TTGGAGTCTCAGAATGGCTTCCTTAAAGACTACCTTCAGACTCTCAGCTGCTCAT
CCACAACAGAGATCAGCC TTTCTTTGTAGATGATTCATTCCTGGCTGCATTTGAA
AACCACATATTGTTAATTGCTTGACGAATTTAAATCCCTTGACTACTTTTCATTTC
AGAAAACACTTACAAAAAAGTCCAAATGAGGACCTTCCCTCCAGTGAATTAGC
TGTGGCTTTCTCACAGTCCATAGTTAGGATAAATGTAAAGCCATTTCTCATTTTTC
TCCGCACTTTCCAAGGGTACACTCCTTGTTTCCAAGATGGAATGAGAAATAAAGA
AGTGCCCTTCCTGCCATCTTCTCCCCTGACCCTTTCCTCCTTCCCACTTTCCTCCTA
TTCCTCCCCAAACATGATTTATTTCTGCGTTTTGCAACTCTTGAGTTCTCAGCATT
TAGTAAATGGTGTTGGTCCCTGTTGAT*CCTTCCTCTCCTGGACCATGGAAGGTA
GTAGGCCTTTCAGAAATTTCAGGTAGCAGCCAAACCCCAGAAGAAGAGAAGGAA
CACAGAGACCTAGACCATGTGAGAACCTGAGGTGTGCAGCATTTACTTC<u>ACAGA
TTCGTCTAGCATATTTGAGAGGTG</u>

SEQ ID NO: 4

<u>TGTCACTATGGAGCTCTCACATGTGG</u>AAGCTGCAAGGTCTTCTTCAAAAGAGCCG
CTGAA*GATTTTTCAGAATGAACAAATTAAAAGAATCATCAGACACTAACCCCA
AGCCATACTGCATGGCAGCACCAATGGGACTGACAGAAAACAACAGAAATAGG
AAGAAATCCTACAGAGAAACAAACTTGAAAGCTGTCTCATGGCCTTTGAATCAT
ACTTAAGTTTTATGATGGAAGGATACGACTATGAAGAAAGACACAGAGCAACAT

-continued

CAGACAGTCAAGAATTTCAGAGCCAGCTGGCATGCAGTGGACCTCATGCCAGCC

CATTTTATGACTATTTAGGGAAACAGAAGTACCTGTGCGCCAGCAGAAATGATTG

CACTATTGATAAATTCCGAAGGAAAAATTGTCCATCTTGTCGTCTTCGGAAATGT

TATGAAGCAGGGATGACTCTGGGAGCAGCTGTTGTTGTTTCTGAAAGAATCTTGA

GGGTGTTTGGAGTCTCAGAATGGCTTCCTTAAAGACTACCTTCAGACTCTCAGCT

GCTCATCCACAACAGAGATCAGCCTTTCTTTGTAGATGATTCATTCCTGGCTGCAT

TTGAAAACCACATATTGTTAATTGCTTGACGAATTTAAATCCCTTGACTACTTTTC

ATTTCAGAAAACACTTACAAAAAAGTCCAAATGAGGACCTTCCCTCCAGTGAA

TTAGCTGTGGCTTTCTCACAGTCCATAGTTAGGATAAATGTAAAGCCATTTCTCAT

TTTTCTCCGCACTTTCCAAGGGTACACTCCTTGTTTCCAAGATGGAATGAGAAAT

AAAGAAGTGCCCTTCCTGCCATCTTCTCCCCTGACCCTTTCCTCCTTCCCACTTTC

CTCCTATTCCTCCCCAAACATGATTTATTTCTGCGTTTTGCAACTCTTGAGTTCTC

AGCATTTAGTAAATGGTGTTGGTCCCTGTTGATTCCTTCCTCTCCTGGACCATGGA

AGGTAGTAGGCCTTTCAGAAATTTCAGGTAGCAGCCAAACCCCAGAAGAAGAGA

AGGAACACAGAGACCTAGACCATGTGAGAACCTGAGGTGTGCAGCATTTACTTC

<u>ACAGATTCGTCTAGCATATTTGAGAGGTG</u>

<u>TGTCACTATGGAGCTCTCACATGTGG</u>AAGCTGCAAGGTCTTCTTCAAAAGAGCCG

CTGAAGGGAAACAGAAGTACCTGTGCGCCAGCAGAAATGATTGCACTATTGATA

AATTCCGAAGGAAAAATTGTCCATCTTGTCGTCTTCGGAAATGTTATGAAGCAGG

GATGACTCTGGGAGGATTTTTCAGAATGAACAAATTAAAAGAATCATCAGACAC

TAACCCCAAGCCATACTGCATGGCAGCACCAATGGGACTGACAGAAAACAACAG

AAATAGGAAGAAATCCTACAGAGAAACAAACTTGAAAGCTGTCTCATGGCCTTT

GAATCATACTTAAGTTTTATGATGGAAGGATACGACTATGAAGAAAGACACAGA

GCAACATCAGACAGTCAAGAATTTCAGAGCCAGCTGGCATGCAGTGGACCTCAT

GCCAGCCCATTTTATGACTATTTAGGGAAACAGAAGTACCTGTGCGCCAGCAGA

AATGATTGCACTATTGATAAATTCCGAAGGAAAAATTGTCCATCTTGTCGTCTTC

GGAAATGTTATGAAGCAGGGATGACTCTGGGAGCAGCTGTTGTTGTTTCTGAAAG

AATCTTGAGGGTGTTTGGAGTCTCAGAATGGCTTCCTTAAAGACTACCTTCAGAC

TCTCAGCTGCTCATCCACAACAGAGATCAGCCTTTCTTTGTAGATGATTCATTCCT

GGCTGCATTTGAAAACCACATATTGTTAATTGCTTGACGAATTTAAATCCCTTGA

CTACTTTTCATTTCAGAAAACACTTACAAAAAAGTCCAAATGAGGACCTTCCCT

CCAGTGAATTAGCTGTGGCTTTCTCACAGTCCATAGTTAGGATAAATGTAAAGCC

ATTTCTCATTTTTCTCCGCACTTTCCAAGGGTACACTCCTTGTTTCCAAGATGGAA

TGAGAAATAAAGAAGTGCCCTTCCTGCCATCTTCTCCCCTGACCCTTTCCTCCTTC

CCACTTTCCTCCTATTCCTCCCCAAACATGATTTATTTCTGCGTTTTGCAACTCTTG

AGTTCTCAGCATTTAGTAAATGGTGTTGGTCCCTGTTGATCCTTCCTCTCCTGGA

CCATGGAAGGTAGTAGGCCTTTCAGAAATTTCAGGTAGCAGCCAAACCCCAGAA

GAAGAGAAGGAACACAGAGACCTAGACCATGTGAGAACCTGAGGTGTGCAGCA

TTTACTTC<u>ACAGATTCGTCTAGCATATTTGAGAGGTG</u>

SEQ ID NO: 5

SEQ ID NO: 6

GGAAACAGAAGTACCTGTGCGCCAGCAGAAATGATTGCACTATTGATAAATTCC

GAAGGAAAAATTGTCCATCTTGTCGTCTTCGGAAATGTTATGAAGCAGGGATGAC

TCTGGGAGACTAGAATTCCAAAGACCCTCAGGCTGGTGATGCAAGTGGGAAGTC

TCATTTCTGAGAAGTGCTGCTTCCTACCCACAATTCTTTGATAGCTGAGTGCTTTA

GCTGATCTGCATAACTGAGGTGTGCACCAAGGAGCAGAATTACTCTATAAATTTT

GGCATCAACATGTGCAACTTGTGACTCAGCACTTTGAAACTCTGGGGATTTTTTT

GTTTGGTTGGTTTTTGTTTTAAGATGTCCTGTGGTATAGTGGAAATAGTACAATAG

ACTCAGATACAGAGAGGCCTTGTTTCTAGTCTTGGTTCTGTCACTTACTATCTTGA

TGTCCTTGCACAAATCACCAGACCTCTCTGAGCCTCAGTTTCTCCAACCACACTGT

GGGAATAATAAAATCTTTTTTACGGCATTGTTGTAAGTATGCAGAGAAACTGGTA

CACAGTAGCCACACAATCAATGTCACCGTACCCTTCAGCCCTTCTTTTGTGGATG

AAAAATGGTCTTTGTGCTCCCAGTCACCACTGGGGTCTGTTCTCTCTCTCTCTGCT

GTTACAGTGTGGCTTTGGTTCTTGTTTCTTTGTTCTTTGGTCTGTAAATTACCCTTG

AAACAACCCTTGAAATTTCCACTCCATGACCTAAATCGTCATCCCTAAATTGGTT

ACATACATATTTGGTGACACTTTGGAGGGGAAAAGCTTTATGTCTCTCTAACGTG

TAGTTCTTAAGGGAATTTGCATATGGAAAAAACAGAGACTGCGTCTCTTAATTCC

TCC

SEQ ID NO: 7

GGAAACAGAAGTACCTGTGCGCCAGCAGAAATGATTGCACTATTGATAAATTCC

GAAGGAAAAATTGTCCATCTTGTCGTCTTCGGAAATGTTATGAAGCAGGGATGAC

TCTGGGAGCAGGCAGCAGAGTGTCATAAAGAATTAACAACGTGGAACTCAGTTA

CTGGGATTTCTTCCATTCTCCTTTGATTCTCTAGACTAGAATTCCAAAGACCCTCA

GGCTGGTGATGCAAGTGGGAAGTCTCATTTCTGAGAAGTGCTGCTTCCTACCCAC

AATTCTTTGATAGCTGAGTGCTTTAGCTGATCTGCATAACTGAGGTGTGCACCAA

GGAGCAGAATTACTCTATAAATTTTGGCATCAACATGTGCAACTTGTGACTCAGC

ACTTTGAAACTCTGGGGATTTTTTTGTTTGGTTGGTTTTTGTTTTAAGATGTCCTGT

GGTATAGTGGAAATAGTACAATAGACTCAGATACAGAGAGGCCTTGTTTCTAGTC

TTGGTTCTGTCACTTACTATCTTGATGTCCTTGCACAAATCACCAGACCTCTCTGA

GCCTCAGTTTCTCCAACCACACTGTGGGAATAATAAAATCTTTTTTACGGCATTGT

TGTAAGTATGCAGAGAAACTGGTACACAGTAGCCACACAATCAATGTCACCGTA

CCCTTCAGCCCTTCTTTTGTGGATGAAAAATGGTCTTTGTGCTCCCAGTCACCACT

GGGGTCTGTTCTCTCTCTCTGCTGTTACAGTGTGGCTTTGGTTCTTGTTTCTTTG

TTCTTTGGTCTGTAAATTACCCTTGAAACAACCCTTGAAATTTCCACTCCATGACC

TAAATCGTCATCCCTAAATTGGTTACATACATATTTGGTGACACTTTGGAGGGGA

AAAGCTTTATGTCTCTCTAACGTGTAGTTCTTAAGGGAATTTGCATATGGAAAAA

ACAGAGACTGCGTCTCTTAATTCCTCC

SEQ ID NO: 39

TGTCACTATGGAGCTCTCACATGTGGAAGCTGCAAGGTCTTCTTCAAAAGAGCCG

CTGAAGGGAAACAGAAGTACCTGTGCGCCAGCAGAAATGATTGCACTATTGATA

AATTCCGAAGGAAAAATTGTCCATCTTGTCGTCTTCGGAAATGTTATGAAGCAGG

GATGACTCTGGGAGACAACTTACCTGAGCAAGCTGCTTTTTGGAGACATTTGCAC

-continued

```
ATCTTTTGGGATCACGTTGTTAAGAAGTAGAACTAAGGGAAAAACACGCAGCCA

CCCAGAAATCGGTAGAGCCTTCAGCTCATCTGTTATTAATATTTCTGTGACAACA

GATATCTAGGAAGTAAACAGGAAATTGCATCGCTATCCTGCATCACCTTTTTGG

AATCAGGTTCCATTCTTCTCAGTCCAGTTCAACCTTGTGATACTTTTTAGATCTCA

ACCAAGGCATAGAAATATATTTTCCCTTGCTTAATACCCCATGGAACCAATGCCC

CTGTGGTTGAAGTAAAAATTGATTGTTGAGGGACATTTCAGCCCTCTAGCAGTCA

ACAATTAAAAACATGTAAGCACCGAGCACCTGCAGAAACTTGGACTGGCATTT

GGATCTAAGAAGAAAATCTGCATCTTGACCAAGATGAAAAGTCACCAGCCCAAG

CTTGTGCAGTGAAGTGTCATGTTGGCCACAATGAAACTGAAAGAGACTGATGAC

TCTCCTCAGGGTGGAAAATGAGGCATGGAAGCTTTGATTAGTGAGCTGTTAGGCA

CACAGACATTAATTTCAAAGCATTCTCATCTCCAGTCTGAGTAATAATGCTTATA

GTATTATGCAATTGTTTGGCTGCTGCAAGAAATTCAGCAGACTCCAACAAGTAGT

CTTTCTTGGTCTCTGAGTGACTGTAACTTAAATTCTACCTCCCTTCTCTTCTCCTAC

ATCTTCTCACTCCCCACCCCACCCCCACATACACACAATTCTTGTCCACTATGTTC

AGAGAGATGCACGCACACATATATATGTATATATATAGTATATTTGTCAATAAAG

CAGAAAAGAAGAAAAAACTCCAAGTAAACAATTTTCCATTTCCCCATCTCACTTC

TGTCTTACAAGTGGATAGGAAAAGAAAAACCCCCAGTAAAAAATGGCAACCGCC

CACCTCCCCAACTTTACATGCTGCTTCCTATGTTAGAGGATCTGTCTTAGGCATCT

GATTATGGAGCCTGCTAGATACAAGCCCGTATTTAGACTGCTACAGTCAACAATG

TCTCTCTTTCATACTAGAAAAATTCC
```

SEQ ID NO: 8
C H Y G A L T C G S C K V F F K R A A E <u>G K Q K Y L C A S R N D C T I D K F R R K N C P S C R L R K C Y E A G M T L G</u> *E K F R V G N C K H L K M T R P* Stop SEQ ID NO: 9
C H Y G A L T C G S C K V F F K R A A E <u>G K Q K Y L C A S R N D C T I D K F R R K N C P S C R L R K C Y E A G M T L G</u> *A V V V S E R I L R V F G V S E W L P* Stop SEQ ID NO: 10
C H Y G A L T C G S C K V F F K R A A E <u>G K Q K Y L C A S R N D C T I D K F R R K N C P S C R L RVK CY E A G M T L G G K Q K Y L C A S R N D C T I D K F R R K N C P S C R L R K C Y E A G M T L G</u> *A V V V S E R I L R V F G V S E W L P* Stop SEQ ID NO: 11
C H Y G A L T C G S C K V F F K R A A *E G F F R M N K L E S S D T N P K Y C M A A P M G L T E N N R N R K K S Y R E T N L K A V S W P L N H T* Stop SEQ ID NO: 12
C H Y G A L T C G S C K V F F K R A A E <u>G K Q K Y L C A S R N D C T I D K F R R K N C P S C R L R K C Y E A G M T L G</u> *G F F R M N K L E S S D T N P K P Y C M A A P M G L T E N N R N R K K S Y R E T N L K A V S W P L N H T* Stop SEQ ID NO: 13
<u>G K Q K Y L C A S R N D C T I D K F R R K N C P S C R L10R K C Y E A G M T L G</u> *D* Stop SEQ ID NO: 14
<u>G K Q K Y L C A S R N D C T I D K F R R K N C P S C R L R K C Y E A G M T L G</u> *A G S R V S* Stop -continued SEQ ID NO: 40
C H Y G A L T C G S C K V F F K R A A E G <u>K Q K Y L C A S R N D C T I D K F R R</u>
<u>K N C P S C R L R K C Y E A G M T L G</u> D N L P E Q A A F W R H L H I F W D H V V K K Stop Other aspects of the invention are described in or are obvious from the following disclosure, and are within the ambit of the invention.

BRIEF DESCRIPTION OF THE DRAWINGS

The following Detailed Description, given by way of example, but not intended to limit the invention to specific embodiments described, may be understood in conjunction with the accompanying drawings, incorporated herein by reference. Various preferred features and embodiments of the present invention will now be described by way of non-limiting example and with reference to the accompanying drawings in which:

FIG. 1A-C shows the cloning of novel AR variants. A, novel AR variants lacking LBD generated by splicing of four cryptic exons. The eight canonical exons of the AR gene were represented by numbered open boxes and shown (not to scale) in relation to the genomic positions of the four cryptic exons (CE1 to CE4) in shaded boxes. The identical forward primer, P1/P2/P3(F), in exon 2 was paired with three reverse primers (P1 R, P2R, and P3R; see Table 2) designed based on Genbank entries for the three transcribed genomic fragments in intron 3 (see Table 1). Sequencing of the amplicons (from CWR22Rv1 cells) defined the 5' junctions of CE1, CE2, and CE3, and 5' and 3' junctions of CE4, as marked by vertical lines with the corresponding genomic coordinates (Human Genome Assembly March 2006, HG1 8). Note that there were four CE1-containing variants (AR-V1, AR-V2, AR-V3, and AR-V4) and that the two CE2-containing variants (AR-V5 and AR-V6) differed by an 80-bp contiguous 5' extension in CE2. Stop codons were marked with the arrowheads in the schematically illustrated transcripts. The seven translated protein sequences corresponding to the seven transcripts were shown, starting from the last four amino acids encoded by exon 3 (AR-V1, AR-V2, AR-V4, AR-V5, AR-V6, and AR-V7) or exon 2 (AR-V3), and followed by variable lengths of variant-specific sequences in light gray that matched the cryptic exons. B, detection of the AR variant transcripts by semi-quantitative RT-PCR in clinical prostate specimens using the same sets of P1, P2, and P3 primers. HRPC (autopsy), metastatic HRPC samples from autopsies; HRPC (TURP), HRPC samples from TURP; PCa (RRP), hormone-naive PCa from RRP specimens. C, amplification of full-length coding region for AR-V1 and AR-V7 using primer sets P4 and P5 (Table 2) from one HRPC autopsy sample, one TURP sample, and the CWR22Rv1 cell line. Identical forward primers, P4(F) and P5(F) located upstream of the translation start codon in exon 1, were paired with reverse primers, P4(R) and P5(R), located downstream of the stop codon in cryptic exon 1 and cryptic exon 3.

FIG. 10A-C shows reduction of the 80 KD protein band following knock down of the AR-V7 transcript or depletion of the AR-V7 protein using anti-AR-V7 antibody. A. Transcript specific knock down of prototype AR (target sequence: UCAAGGAACUCGAUCGUAU; SEQ ID NO: 34) and AR-V7 (target sequence: GUAGUUGUGAGUAU-CAUGA; SEQ ID NO: 1). B. Standard immunoblot analysis with anti-AR(N20), anti-AR-V7 and anti-β-actin antibodies following gene knock down. C. Standard immunoblot (IB) analysis with anti-AR(N20), anti-AR-V7 in CWR22Rv1 whole cell lysate following depletion of AR-V7 using anti-AR-V7 antibody. CWR22Rv1 cell lysate was incubated with protein G resin coupled to anti-AR-V7 antibody to deplete AR-V7 (anti-AR-V7 depleted) or protein G resin alone as a control (no depletion).

FIG. 12A-C shows development of polyclonal mouse anti-human AR-V7 antibody. The panels show testing initial bleeds from 6 mice immunized with peptide sequences specific to AR-V7 (CKHLKMRP; SEQ ID NO: 1). A. ELISA results (plate (A) and log sheet (B)) using two different preparations of coating peptide antigens. JHU014 (top half of the plate) antigen was the same as the immunogen, while JHU016 antigen (bottom half of the plate) has identical sequence but made separately. C. western blot to test the antibody. CWR22Rv1 whole cell lysates were used. Serum was diluted 1:1000. The molecular weight of the AR-V7 antigen is expected to be ~75-80 KD. The position of the 75 Kda protein marker was indicated by an arrow. Relatively specific positive signals were detected in mouse #2, 4, and 5.

FIG. 13 shows western blot analysis of subsequent bleeds (following boosting) from mouse #1 and #2 (Ab used at 1:1000 dilution). Specific detection of AR-V7 antigen was performed using 293 T cells transfected with control vector (293T no transfection) or vector which over-expresses AR-V7 (293T+AR-V7), as well as PC-3 (negative control) and CWR22Rv1 whole cell lysates (WCL) (positive control). Based on the result, JHU019#2 mouse was chosen for fusion and subsequent hybridoma generation.

FIG. 14A-B shows initial hybridma screening results shown in scanned image (A) of the ELISA plates and a log sheet (B). Strong positive signals were detected in well 4E4 and 2D12. The positive control is polyclonal serum at 1:1000 dilution, on plate 4 in well H5 (4H5).

FIG. 15A-B shows confirmatory ELISA results of selected clones in scanned log sheet (B) and plate image (A). Clone IDs corresponding to the original plate and well designations were shown in the log sheet to indicate their position in this assayed plate. The top half of the plate was used to detect IgG while the bottom half designed to detect IgM. 2D12 was confirmed as a strong IgG positive clone. Other candidate clones were also expanded for downstream analysis. These included 2B6 (IgM), 4F7 (IgM), 4E4 (IgM), and 1A1 (IgG). PC: positive control which was serum at 1:1000 dilution.

DETAILED DESCRIPTION OF THE INVENTION

I. Definitions

Figure 1A:
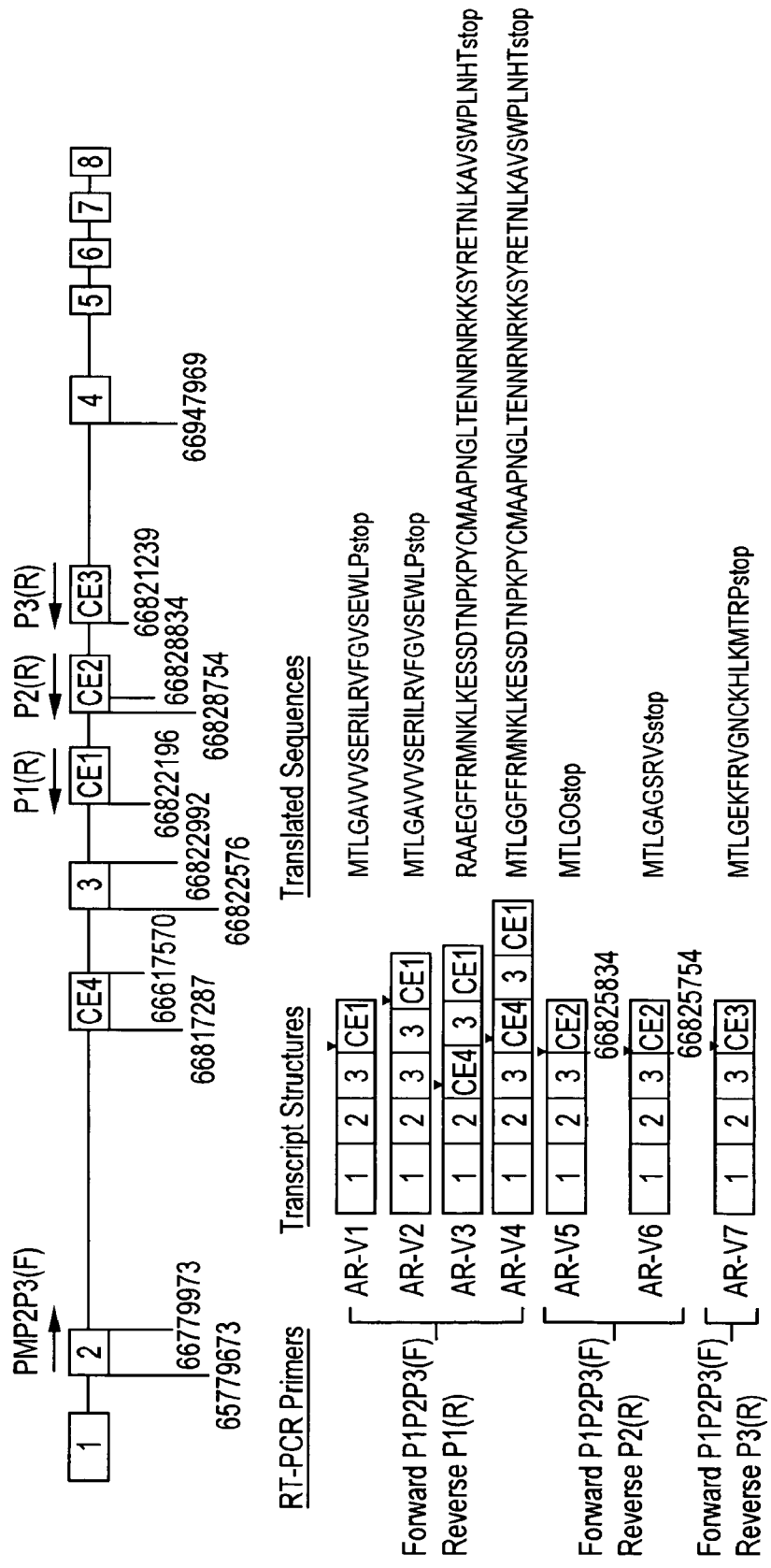

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

By "antibody" is meant any immunoglobulin polypeptide, or fragment thereof, having immunogen binding ability.

By "androgen receptor" (AR) is meant a member of the steroid hormone receptor family of molecules. AR mediates the physiologic effects of androgens by binding to DNA sequences that influence transcription or androgen-responsive genes. The wild-type AR mRNA reference sequence corresponds to GenBank database Accession No. NM 000044 (corresponding to SEQ ID NO: 34).

By "androgen receptor polypeptide" is meant a protein or protein variant, or fragment thereof, that is substantially identical to at least a portion of GenBank Accession No. NP 000035 (Corresponding to SEQ ID NO: 35) and that has an androgen receptor biological activity.

By "androgen receptor nucleic acid molecule" is meant a polynucleotide encoding an androgen receptor polypeptide or variant, or fragment thereof.

By "androgen related disease or disorder" is meant to refer to any disease or disorder that results from an imbalance of androgen in the body. Examples of androgen related diseases or disorders include prostate cancer, androgenic alopecia, infertility, irregular menstrual periods, excessive hair growth, acne, obesity and insulin resistance, and polycystic ovarian syndrome.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, for example, hydroxyproline, gamma-carboxyglutamate, and O-phosphoserine, phosphothreonine.

By "biomarker" is meant any protein or polynucleotide having an alteration in expression level or activity that is associated with a disease or disorder, for example an androgen related disease or disorder.

By "detectable amino acid sequence" or "detectable moiety" is meant a composition that when linked with the nucleic acid or protein molecule of interest renders the latter detectable, via any means, including spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

A "labeled nucleic acid or oligonucleotide probe" is one that is bound, either covalently, through a linker or a chemical bond, or noncovalently, through ionic bonds, van der Waals forces, electrostatic attractions, hydrophobic interactions, or hydrogen bonds, to a label such that the presence of the nucleic acid or probe may be detected by detecting the presence of the label bound to the nucleic acid or probe.

An "expression vector" is a nucleic acid construct, generated recombinantly or synthetically, bearing a series of specified nucleic acid elements that enable transcription of a particular gene in a host cell. Typically, gene expression is placed under the control of certain regulatory elements, including constitutive or inducible promoters, tissue-preferred regulatory elements, and enhancers.

By "fragment" is meant a portion (e.g., at least 10, 25, 50, 100, 125, 150, 200, 250, 300, 350, 400, or 500 amino acids or nucleic acids) of a protein or nucleic acid molecule that is substantially identical to a reference protein or nucleic acid and retains the biological activity of the reference. In some embodiments the portion retains at least 50%, 75%, or 80%, or more preferably 90%, 95%, or even 99% of the biological activity of the reference protein or nucleic acid described herein.

A "host cell" is any prokaryotic or eukaryotic cell that contains either a cloning vector or an expression vector. This term also includes those prokaryotic or eukaryotic cells that have been genetically engineered to contain the cloned gene(s) in the chromosome or genome of the host cell.

By "inhibitory nucleic acid" is meant a double-stranded RNA, siRNA (short interfering RNA), shRNA (short hairpin RNA), or antisense RNA, or a portion thereof, or a mimetic thereof, that when administered to a mammalian cell results in a decrease (e.g., by 10%, 25%, 50%, 75%, or even 90-100%) in the expression of a target gene. Typically, a nucleic acid inhibitor comprises at least a portion of a target nucleic acid molecule, or an ortholog thereof, or comprises at least a portion of the complementary strand of a target nucleic acid molecule.

The terms "isolated," "purified," or "biologically pure" refer to material that is free to varying degrees from components which normally accompany it as found in its native state. Various levels of purity may be applied as needed according to this invention in the different methodologies set forth herein; the customary purity standards known in the art may be used if no standard is otherwise specified.

By "isolated nucleic acid molecule" is meant a nucleic acid (e.g., a DNA, RNA, or analog thereof) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule which is transcribed from a DNA molecule, as well as a recombinant DNA which is part of a hybrid gene encoding additional polypeptide sequence.

"Microarray" is meant to refer to a collection of nucleic acid molecules or polypeptides from one or more organisms arranged on a solid support (for example, a chip, plate, or bead).

By "nucleic acid" is meant an oligomer or polymer of ribonucleic acid or deoxyribonucleic acid, or analog thereof. This term includes oligomers consisting of naturally occurring bases, sugars, and intersugar (backbone) linkages as well as oligomers having non-naturally occurring portions which function similarly. Such modified or substituted oligonucleotides are often preferred over native forms because of properties such as, for example, enhanced stability in the presence of nucleases.

"Complimentary nucleic acid sequences" refer to contiguous DNA or RNA sequences which have compatible nucleotides (e.g., A/T, G/C) in corresponding positions, such that base pairing between the sequences occurs. For example, the sense and anti-sense strands of a double-stranded DNA helix are known in the art to be complimentary.

By "protein" is meant any chain of amino acids, or analogs thereof, regardless of length or post-translational modification.

By "reference" is meant a standard or control condition.

By "siRNA" is meant a double stranded RNA. Optimally, an siRNA is 18, 19, 20, 21, 22, 23 or 24 nucleotides in length and has a 2 base overhang at its 3' end. These dsRNAs can be introduced to an individual cell or to a whole animal; for example, they may be introduced systemically via the bloodstream. Such siRNAs are used to downregulate mRNA levels or promoter activity.

By "specifically binds" is meant a molecule (e.g., peptide, polynucleotide) that recognizes and binds a protein or nucleic acid molecule of the invention, but which does not substantially recognize and bind other molecules in a sample, for example, a biological sample, which naturally includes a protein of the invention.

By "substantially identical" is meant a protein or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and most preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between e-3 and e-100 indicating a closely related sequence.

Other definitions appear in context throughout the disclosure.

METHODS OF THE INVENTION

The invention features compositions and methods useful for the diagnosis and prognosis of androgen related diseases or disorders in a subject. The invention features compositions and methods useful for detecting, treating or preventing prostate cancer. These methods and compositions are based, in part, on the discovery that expression of certain androgen receptor variants is elevated in certain prostate cancers. The invention also provides methods and compositions for altering androgen receptor variant expression, and may be useful, for example, for the treatment of androgen related diseases, such as prostate cancer.

In particular, the invention is based on the finding that particular androgen receptor variants lacking the ligand binding domain (LBD), but that retained intact coding potential for the full androgen receptor NH2-terminal domain (NTD) and DNA-binding domain (DBD), were overexpressed in hormone refractory prostate cancer. One of the variants, AR-V7, was expressed at elevated levels in a subset of hormone naïve prostate cancers that recurred after surgical treatment.

Androgen Receptor Variants

The androgen receptor (AR) is a member of the steroid hormone receptor family of molecules. The AR primarily is responsible for mediating the physiologic effects of androgens by binding to specific DNA sequences that influence transcription or androgen-responsive genes. The human AR gene is located on chromosome Xq11-12 and spans approximately 180 kb of DNA containing eight exons that code for an approximately 2,757 base pair open reading frame within a 10.6 kb mRNA (Gelmann 2002). This gene structure is evolutionarily conserved among the sex steroid hormone receptors. The AR protein product is approximately 919 amino acids long and has a number of functional domains. The first exon codes for the N-terminal domain (NTD), which is the transcriptional regulatory region of the protein, exons 2 and 3 code for the central DNA binding domain (DBD), the first part of exon 4 encodes a hinge region, and exons 4-8 code for the C-terminal ligand-binding domain (LBD). A schematic diagram of the AR gene and protein can be seen in FIG. 1A. Genomic sequence for the human AR gene was obtained from the 2006 NCBI human genome assembly (HG 18). The sequence spans nucleotides 66680599-66860844 on chromosome X. The wild-type AR mRNA reference sequence corresponds to GenBank database Accession No. NM_000044.2, shown below, and corresponding to SEQ ID NO: 34.

```
                                                    SEQ ID NO: 34
   1 cgagatcccg gggagccagc ttgctgggag agcgggacgg tccggagcaa gcccagaggc 61 agaggaggcg acagagggaa aaagggccga gctagccgct ccagtgctgt acaggagccg 121 aagggacgca ccacgccagc cccagcccgg ctccagcgac agccaacgcc tcttgcagcg 181 cggcggcttc gaagccgccg cccgagctg cccttcctc ttcggtgaag tttttaaaag 241 ctgctaaaga ctcggaggaa gcaaggaaag tgcctggtag gactgacggc tgcctttgtc 301 ctcctcctct ccacccgcc tcccccacc ctgccttccc ccctccccc gtcttctctc 361 ccgcagctgc ctcagtcggc tactctcagc caaccccct caccaccctt ctccccaccc 421 gccccccgc cccgtcggc ccagcgctgc cagcccgagt ttgcagagag gtaactccct 481 ttggctgcga gcgggcgagc tagctgcaca ttgcaaagaa ggctcttagg agccaggcga 541 ctggggagcg gcttcagcac tgcagccacg acccgcctgg ttaggctgca cgcggagaga 601 accctctgtt ttcccccact ctctctccac ctcctcctgc cttccccacc ccgagtgcgg 661 agccagagat caaaagatga aaaggcagtc aggtcttcag tagccaaaaa acaaaacaaa 721 caaaaacaaa aaagccgaaa taaaagaaaa agataataac tcagttctta tttgcaccta 781 cttcagtgga cactgaattt ggaaggtgga ggattttgtt tttttctttt aagatctggg 841 catcttttga atctaccctt caagtattaa gagacagact gtgagcctag cagggcagat 901 cttgtccacc gtgtgtcttc ttctgcacga gactttgagg ctgtcagagc gcttttttgcg 961 tggttgctcc cgcaagtttc cttctctgga gcttcccgca ggtgggcagc tagctgcagc 1021 gactaccgca tcatcacagc ctgttgaact cttctgagca agagaagggg aggcggggta 1081 agggaagtag gtggaagatt cagccaagct caaggatgga agtgcagtta gggctgggaa 1141 gggtctaccc tcggccgccg tccaagacct accgaggagc tttccagaat ctgttccaga 1201 gcgtgcgcga agtgatccag aacccgggcc ccaggcaccc agaggccgcg agcgcagcac 1261 ctcccggcgc cagtttgctg ctgctgcagc agcagcagca gcagcagcag cagcagcagc
```

-continued

```
1321 agcagcagca gcagcagcag cagcagcagc agcaagagac tagccccagg cagcagcagc
1381 agcagcaggg tgaggatggt tctccccaag cccatcgtag aggccccaca ggctacctgg
1441 tcctggatga ggaacagcaa ccttcacagc cgcagtcggc cctggagtgc caccccgaga
1501 gaggttgcgt cccagagcct ggagccgccg tggccgccag caaggggctg ccgcagcagc
1561 tgccagcacc tccggacgag gatgactcag ctgccccatc cacgttgtcc ctgctgggcc
1621 ccactttccc cggcttaagc agctgctccg ctgaccttaa agacatcctg agcgaggcca
1681 gcaccatgca actccttcag caacagcagc aggaagcagt atccgaaggc agcagcagcg
1741 ggagagcgag ggaggcctcg ggggctccca cttcctccaa ggacaattac ttaggggggca
1801 cttcgaccat ttctgacaac gccaaggagt tgtgtaaggc agtgtcggtg tccatgggcc
1861 tgggtgtgga ggcgttggag catctgagtc caggggaaca gcttcggggg gattgcatgt
1921 acgccccact tttgggagtt ccacccgctg tgcgtcccac tccttgtgcc ccattggccg
1981 aatgcaaagg ttctctgcta gacgacagcg caggcaagag cactgaagat actgctgagt
2041 attccccttt caagggaggt tacaccaaag ggctagaagg cgagagccta ggctgctag
2101 gcagcgctgc agcagggagc tccgggacac ttgaactgcc gtctacccctg tctctctaca
2161 agtccggagc actggacgag gcagctgcgt accagagtcg cgactactac aacttttccac
2221 tggctctggc cggaccgccg ccccctccgc cgcctcccca tccccacgct cgcatcaagc
2281 tggagaaccc gctggactac ggcagcgcct gggcggctgc ggcggcgcag tgccgctatg
2341 ggacctggc gagcctgcat ggcgcgggtg cagcgggacc cggttctggg tcaccctcag
2401 ccgccgcttc ctcatcctgg cacactctct tcacagccga agaaggccag ttgtatggac
2461 cgtgtggtgg tggtgggggt ggtggcggcg gcggcggcgg cggcggcggc ggcggcggcg
2521 gcggcggcgc cggcgaggcg ggagctgtag cccctacgg ctacactcgg cccctcagg
2581 ggctggcggg ccaggaaagc gacttcaccg cacctgatgt gtggtaccct ggcggcatgg
2641 tgagcagagt gccctatccc agtcccactt gtgtcaaaag cgaaatgggc ccctggatgg
2701 atagctactc cggaccttac ggggacatgc gtttggagac tgccagggac catgttttgc
2761 ccattgacta ttactttcca ccccagaaga cctgcctgat ctgtggagat gaagcttctg
2821 ggtgtcacta tggagctctc acatgtggaa gctgcaaggt cttcttcaaa agagccgctg
2881 aagggaaaca gaagtacctg tgcgccagca gaaatgattg cactattgat aaattccgaa
2941 ggaaaaattg tccatcttgt cgtcttcgga atgttatga agcagggatg actctgggag
3001 cccggaagct gaagaaactt ggtaatctga actacaggag ggaaggagag gcttccagca
3061 ccaccagccc cactgaggag acaacccaga agctgacagt gtcacacatt gaaggctatg
3121 aatgtcagcc catcttctg aatgtcctgg aagccattga ccaggtgta gtgtgtgctg
3181 gacacgacaa caaccagccc gactcctttg cagccttgct ctctagcctc aatgaactgg
3241 gagagagaca gcttgtacac gtggtcaagt gggccaaggc cttgcctggc ttccgcaact
3301 tacacgtgga cgaccagatg gctgtcattc agtactcctg gatggggctc atggtgtttg
3361 ccatgggctg gcgatccttc accaatgtca actccaggat gctctacttc gcccctgatc
3421 tggttttcaa tgagtaccgc atgcacaagt cccggatgta cagccagtgt gtccgaatga
3481 ggcacctctc tcaagagttt ggatggctcc aaatcacccc ccaggaattc tgtgcatga
3541 aagcactgct actcttcagc attattccag tggatgggct gaaaaatcaa aaattctttg
3601 atgaacttcg aatgaactac atcaaggaac tcgatcgtat cattgcatgc aaaagaaaaa
3661 atcccacatc ctgctcaaga cgcttctacc agctcaccaa gctcctggac tccgtgcagc
3721 ctattgcgag agagctgcat cagttcactt ttgacctgct aatcaagtca cacatggtga
```

```
3781 gcgtggactt tccggaaatg atggcagaga tcatctctgt gcaagtgccc aagatcctt 3841 ctgggaaagt caagcccatc tatttccaca cccagtgaag cattggaaac cctatttccc 3901 caccccagct catgccccct ttcagatgtc ttctgcctgt tataactctg cactactcct 3961 ctgcagtgcc ttggggaatt tcctctattg atgtacagtc tgtcatgaac atgttcctga 4021 attctatttg ctgggctttt tttttctctt tctctccttt cttttcttc ttccctccct 4081 atctaaccct cccatggcac cttcagactt tgcttcccat tgtggctcct atctgtgttt 4141 tgaatggtgt tgtatgcctt taaatctgtg atgatcctca tatggcccag tgtcaagttg 4201 tgcttgttta cagcactact ctgtgccagc cacacaaacg tttacttatc ttatgccacg 4261 ggaagtttag agagctaaga ttatctgggg aaatcaaaac aaaaacaagc aaac
```

The wild-type AR protein reference sequence corresponds to GenBank database Accession No. NP 000035, shown below, and corresponding to SEQ ID NO: 35.

```
                                                              SEQ ID NO: 35
   1 mevqlglgrv yprppsktyr gafqnlfqsv reviqnpgpr hpeaasaapp gaslllqqq 61 qqqqqqqqq qqqqqqqqq etsprqqqqq qgedgspqah rrgptgylvl deeqqpsqpq 121 salechperg cvpepgaava askglpqqlp appdeddsaa pstlsllgpt fpglsscsad 181 lkdilseast mqllqqqqe aysegsssgr areasgapts skdnylggts tisdnakelc 241 kaysysmglg vealehlspg eqlrgdcmya pllgvppavr ptpcaplaec kgslldsag 301 kstedtaeys pfkggytkgl egeslgcsgs aaagssgtle lpstlslyks galdeaaayq 361 srdyynfpla lagppppppp phpharikle npldygsawa aaaaqcrygd laslhgagaa 421 gpgsgspsaa assswhtlft aeegqlygpc ggggggggg ggggggggg gggeagavap 481 ygytrppqgl agqesdftap dvwypggmvs rvpypsptcv ksemgpwmds ysgpygdmrl 541 etardhvlpi dyyfppqktc licgdeasgc hygaltcgsc kvffkraaeg kqkylcasrn 601 dctidkfrrk ncpscrlrkc yeagmtlgar klkklgnlkl qeegeasstt spteettqkl 661 tvshiegyec qpiflnvlea iepgvvcagh dnnqpdsfaa llsslnelge rqlvhvvkwa 721 kalpgfrnlh vddqmaviqy swmglmvfam gwrsftnvns rmlyfapdlv fneyrmhksr 781 mysqcvrrnrh lsqefgwlqi tpqeflcmka lllfsiipvd glknqkffde lrmnyikeld 841 riiackrknp tscsrrfyql tklldsvqpi arelhqftfd llikshmvsv dfpemmaeii 901 svqvpkilsg kvkpiyfhtq
```

The present invention describes novel androgen receptor variants that lack the androgen receptor ligand binding domain (LBD). The present invention describes multiple novel androgen receptor LBD transcript variants with intact coding potential for the full androgen receptor NTD and androgen receptor DBD, but impaired coding potential for the androgen receptor LBD. Each of the variants can be uniquely identified by its variant-specific sequence. It is a finding of the present invention that these novel AR transcripts were overexpressed in hormone refractory prostate cancer (HPRC) and one of the most abundant variants, AR-V7, was expressed at elevated levels in a subset of hormone-naive PCa that recurred after surgical treatment.

Accordingly, the invention features polypeptides comprising an isolated androgen receptor protein variant, or fragment thereof, having substantial identity to androgen receptor variant 1, 2, 3, 4, 5, 6, 7 or 8 (AR-V1-AR-V8), wherein the variant is upregulated in an androgen related disease or disorder. In particular examples, the polypeptide comprising an isolated androgen receptor protein variant, or fragment thereof, having substantial identity to androgen receptor variant 1, 2, 3, 4, 5, 6, 7 or 8 (AR-V1-AR-V8) is upregulated in prostate cancer.

Preferably, the androgen receptor protein variant is at least 85% identical to androgen receptor variant 1, 2, 3, 4, 5, 6, 7 or 8.

As described herein the androgen receptor protein variant comprises the androgen receptor NH2 terminal domain (NTD), DNA binding domain (DBD), and the c-terminal variant specific peptide sequence that uniquely identifies each variant.

In certain preferred examples, the androgen receptor variant nucleic acid comprises a sequence selected from any one or more of SEQ ID NO: 1, SEQ ID NO: 39, SEQ ID NO: 2, SEQ ID NO: 3, SEQ ID NO: 4, SEQ ID NO: 5, SEQ ID NO: 6 and SEQ ID NO: 7 or fragments thereof.

SEQ ID NO: 1 corresponds to the nucleotide sequence of transcript AR V7. Most of the upstream sequence common to all androgen receptors, corresponding to nucleotide 1-2822 of SEQ ID NO: 34, is not included. The first nucleotide of the variant specific sequences is shaded.

SEQ ID NO: 2
TGTCACTATGGAGCTCTCACATGTGGAAGCTGCAAGGTCTTCTTCAAAAG
AGCCGCTGAAGGGAAACAGAAGTACCTGTGCGCCAGCAGAAATGATTGCA
CTATTGATAAATTCCGAAGGAAAAATTGTCCATCTTGTCGTCTTCGGAAA
TGTTATGAAGCAGGGATGACTCTGGGAGAAAAATTCCGGGTTGGC
AATTGCAAGCATCTCAAAATGACCAGACCCTGAAGAAAGGCTGACTTGCC
TCATTCAAAATGAGGGCTCTAGAGGGCTCTAGTGGATAGTCTGGAGAAAC
CTGGCGTCTGAGGCTTAGGAGCTTAGGTTTTTGCTCCTCAACACAGACTT
TGACGTTGGGGTTGGGGGCTACTCTCTTGATTGCTGACTCCCTCCAGCGG
GACCAATAGTGTTTTCCTACCTCACAGGGATGTTGTGAGGACGGGCTGTA
GAAGTAATAGTGGTTACCACTCATGTAGTTGTGAGTATCATGATTATTGT
TTCCTGTAATGTGGCTTGGCATTGGCAAAGTGCTTTTTGATTGTTCTTGA
TCACATATGATGGGGCCAGGCACTGACTCAGGCGGATGCAGTGAAGCTC
TGGCTCAGTCGCTTGCTTTTCGTGGTGTGCTGCCAGGAAGAAACTTTGCT
GATGGGACTCAAGGTGTCACCTTGGACAAGAAGCAACTGTGTCTGTCTGA
GGTTCCTGTGGCCATCTTTATTTGTGTATTAGGCAATTCGTATTTCCCCC
TTAGGTTCTAGCCTTCTGGATCCCAGCCAGTGACCTAGATCTTAGCCTCA
GGCCCTGTCACTGAGCTGAAGGTAGTAGCTGATCCACAGAAGTTCAGTAA
ACAAGGACCAGATTTCTGCTTCTCCAGGAGAAGAAGCCAGCCAACCCCTC
TCTTCAAACACACTGAGAGACTACAGTCCGACTTTCCCTCTTACATCTAG
CCTTACTGTAGCCACACTCCTTGATTGCTCTCTCACATCACATGCTTCTC
TTCATCAGTTGTAAGCCTCTCATTCTTCTCCCAAGCCAGACTCAAATATT
GTATTGATGTCAAAGAAGAATCACTTAGAGTTTGGAATATCTTGTTCTCT
CTCTGCTCCATAGCTTCCATATTGACACCAGTTTCTTTCTAGTGGAGAAG
TGGAGTCTGTGAAGCCAGGGAAACACACATGTGAGAGTCAGAAGGACTCT
CCC

SEQ ID NO: 2 corresponds to the nucleotide sequence of transcript AR V1. Most of the upstream sequence common to all androgen receptors, corresponding to nucleotide 1-2822 of SEQ ID NO: 34, is not included. The first nucleotide of the variant specific sequences is shaded.

SEQ ID NO: 3
TGTCACTATGGAGCTCTCACATGTGGAAGCTGCAAGGTCTTCTTCAAAAG
AGCCGCTGAAGGGAAACAGAAGTACCTGTGCGCCAGCAGAAATGATTGCA
CTATTGATAAATTCCGAAGGAAAAATTGTCCATCTTGTCGTCTTCGGAAA
TGTTATGAAGCAGGGATGACTCTGGGACTGTTGTTGTTTCTGAA
AGAATCTTGAGGGTGTTTGGAGTCTCAGAATGGCTTCCTTAAAGACTACC
TTCAGACTCTCAGCTGCTCATCCACAACAGAGATCAGCCTTTCTTTGTAG
ATGATTCATTCCTGGCTGCATTTGAAAACCACATATTGTTAATTGCTTGA
CGAATTTAAATCCCTTGACTACTTTTCATTTCAGAAAACACTTACAAAAA
AAGTCCAAATGAGGACCTTCCCTCCAGTGAATTAGCTGTGGCTTTCTCAC

AGTCCATAGTTAGGATAAATGTAAAGCCATTTCTCATTTTTCTCCGCACT
TTCCAAGGGTACACTCCTTGTTTCCAAGATGGAATGAGAAATAAAGAAGT
GCCCTTCCTGCCATCTTCTCCCCTGACCCTTTCCTCCTTCCCACTTTCCT
CCTATTCCTCCCCAAACATGATTTATTTCTGCGTTTTGCAACTCTTGAGT
TCTCAGCATTTAGTAAATGGTGTTGGTCCCTGTTGATTCCTTCCTCTCCT
GGACCATGGAAGGTAGTAGGCCTTTCAGAAATTTCAGGTAGCAGCCAAAC
CCCAGAAGAAGAGAAGGAACACAGAGACCTAGACCATGTGAGAACCTGAG
GTGTGCAGCATTTACTTCACAGATTCGTCTAGCATATTTGAGAGGTG

SEQ ID NO: 3 corresponds to the nucleotide sequence of transcript AR V2. Most of the upstream sequence common to all androgen receptors, corresponding to nucleotide 1-2822 of SEQ ID NO: 34, is not included. The first nucleotide of the variant specific sequences is shaded.

SEQ ID NO: 4
TGTCACTATGGAGCTCTCACATGTGGAAGCTGCAAGGTCTTCTTCAAAAG
AGCCGCTGAAGGGAAACAGAAGTACCTGTGCGCCAGCAGAAATGATTGCA
CTATTGATAAATTCCGAAGGAAAAATTGTCCATCTTGTCGTCTTCGGAAA
TGTTATGAAGCAGGGATGACTCTGGGAGGGAAACAGAAGTACCTGTGCGC
CAGCAGAAATGATTGCACTATTGATAAATTCCGAAGGAAAAATTGTCCAT
CTTGTCGTCTTCGGAAATGTTATGAAGCAGGGATGACTCTGGGA
CTGTTGTTGTTTCTGAAAGAATCTTGAGGGTGTTTGGAGTCTCAGAATGG
CTTCCTTAAAGACTACCTTCAGACTCTCAGCTGCTCATCCACAACAGAGA
TCAGCCTTTCTTTGTAGATGATTCATTCCTGGCTGCATTTGAAAACCACA
TATTGTTAATTGCTTGACGAATTTAAATCCCTTGACTACTTTTCATTTCA
GAAAACACTTACAAAAAAGTCCAAATGAGGACCTTCCCTCCAGTGAATT
AGCTGTGGCTTTCTCACAGTCCATAGTTAGGATAAATGTAAAGCCATTTC
TCATTTTTCTCCGCACTTTCCAAGGGTACACTCCTTGTTTCCAAGATGGA
ATGAGAAATAAAGAAGTGCCCTTCCTGCCATCTTCTCCCCTGACCCTTTC
CTCCTTCCCACTTTCCTCCTATTCCTCCCCAAACATGATTTATTTCTGCG
TTTTGCAACTCTTGAGTTCTCAGCATTTAGTAAATGGTGTTGGTCCCTGT
TGATCCTTCCTCTCCTGGACCATGGAAGGTAGTAGGCCTTTCAG
AAATTTCAGGTAGCAGCCAAACCCCAGAAGAAGAGAAGGAACACAGAGAC
CTAGACCATGTGAGAACCTGAGGTGTGCAGCATTTACTTCACAGATTCGT
CTAGCATATTTGAGAGGTG

SEQ ID NO: 4 corresponds to the nucleotide sequence of transcript AR V3. Most of the upstream sequence common to all androgen receptors, corresponding to nucleotide 1-2822 of SEQ ID NO: 34, is not included. The first nucleotide of the variant specific sequences is shaded.

SEQ ID NO: 5
TGTCACTATGGAGCTCTCACATGTGGAAGCTGCAAGGTCTTCTTCAAAAG
AGCCGCTGAAGATTTTTCAGAATGAACAAATTAAAAGAATCATC
AGACACTAACCCCAAGCCATACTGCATGGCAGCACCAATGGGACTGACAG

-continued

AAAACAACAGAAATAGGAAGAAATCCTACAGAGAAACAAACTTGAAAGCT

GTCTCATGGCCTTTGAATCATACTTAAGTTTTATGATGGAAGGATACGAC

TATGAAGAAAGACACAGAGCAACATCAGACAGTCAAGAATTTCAGAGCCA

GCTGGCATGCAGTGGACCTCATGCCAGCCCATTTTATGACTATTTAGGGA

AACAGAAGTACCTGTGCGCCAGCAGAAATGATTGCACTATTGATAAATTC

CGAAGGAAAAATTGTCCATCTTGTCGTCTTCGGAAATGTTATGAAGCAGG

GATGACTCTGGGAGCAGCTGTTGTTGTTTCTGAAAGAATCTTGAGGGTGT

TTGGAGTCTCAGAATGGCTTCCTTAAAGACTACCTTCAGACTCTCAGCTG

CTCATCCACAACAGAGATCAGCCTTTCTTTGTAGATGATTCATTCCTGGC

TGCATTTGAAAACCACATATTGTTAATTGCTTGACGAATTTAAATCCCTT

GACTACTTTTCATTTCAGAAAACACTTACAAAAAAGTCCAAATGAGGAC

CTTCCCTCCAGTGAATTAGCTGTGGCTTTCTCACAGTCCATAGTTAGGAT

AAATGTAAAGCCATTTCTCATTTTTCTCCGCACTTTCCAAGGGTACACTC

CTTGTTTCCAAGATGGAATGAGAAATAAAGAAGTGCCCTTCCTGCCATCT

TCTCCCCTGACCCTTTCCTCCTTCCCACTTTCCTCCTATTCCTCCCCAAA

CATGATTTATTTCTGCGTTTTGCAACTCTTGAGTTCTCAGCATTTAGTAA

ATGGTGTTGGTCCCTGTTGATTCCTTCCTCTCCTGGACCATGGAAGGTAG

TAGGCCTTTCAGAAATTTCAGGTAGCAGCCAAACCCCAGAAGAAGAGAAG

GAACACAGAGACCTAGACCATGTGAGAACCTGAGGTGTGCAGCATTTACT

TCACAGATTCGTCTAGCATATTTGAGAGGTG

SEQ ID NO: 5 corresponds to the nucleotide sequence of transcript AR V4. Most of the upstream sequence common to all androgen receptors, corresponding to nucleotide 1-2822 of SEQ ID NO: 34, is not included. The first nucleotide of the variant specific sequences is shaded.

SEQ ID NO: 6
TGTCACTATGGAGCTCTCACATGTGGAAGCTGCAAGGTCTTCTTCAAAAG

AGCCGCTGAAGGGAAACAGAAGTACCTGTGCGCCAGCAGAAATGATTGCA

CTATTGATAAATTCCGAAGGAAAAATTGTCCATCTTGTCGTCTTCGGAAA

TGTTATGAAGCAGGGATGACTCTGGGAAGATTTTTCAGAATGAAC

AAATTAAAGAATCATCAGACACTAACCCCAAGCCATACTGCATGGCAGC

ACCAATGGGACTGACAGAAAACAACAGAAATAGGAAGAAATCCTACAGAG

AAACAAACTTGAAAGCTGTCTCATGGCCTTTGAATCATACTTAAGTTTTA

TGATGGAAGGATACGACTATGAAGAAAGACACAGAGCAACATCAGACAGT

CAAGAATTTCAGAGCCAGCTGGCATGCAGTGGACCTCATGCCAGCCCATT

TTATGACTATTTAGGGAAACAGAAGTACCTGTGCGCCAGCAGAAATGATT

GCACTATTGATAAATTCCGAAGGAAAAATTGTCCATCTTGTCGTCTTCGG

AAATGTTATGAAGCAGGGATGACTCTGGGAGCAGCTGTTGTTGTTTCTGA

AAGAATCTTGAGGGTGTTTGGAGTCTCAGAATGGCTTCCTTAAAGACTAC

CTTCAGACTCTCAGCTGCTCATCCACAACAGAGATCAGCCTTTCTTTGTA

GATGATTCATTCCTGGCTGCATTTGAAAACCACATATTGTTAATTGCTTG

ACGAATTTAAATCCCTTGACTACTTTTCATTTCAGAAAACACTTACAAAA

AAGTCCAAATGAGGACCTTCCCTCCAGTGAATTAGCTGTGGCTTTCTCA

CAGTCCATAGTTAGGATAAATGTAAAGCCATTTCTCATTTTTCTCCGCAC

TTTCCAAGGGTACACTCCTTGTTTCCAAGATGGAATGAGAAATAAAGAAG

TGCCCTTCCTGCCATCTTCTCCCCTGACCCTTTCCTCCTTCCCACTTTCC

TCCTATTCCTCCCCAAACATGATTTATTTCTGCGTTTTGCAACTCTTGAG

TTCTCAGCATTTAGTAAATGGTGTTGGTCCCTGTTGATTCCTTCC

TCTCCTGGACCATGGAAGGTAGTAGGCCTTTCAGAAATTTCAGGTAGCAG

CCAAACCCCAGAAGAAGAGAAGGAACACAGAGACCTAGACCATGTGAGAA

CCTGAGGTGTGCAGCATTTACTTCACAGATTCGTCTAGCATATTTGAGAG

GTG

SEQ ID NO: 6 corresponds to the nucleotide sequence of transcript AR V5. Most of the upstream sequence common to all androgen receptors, corresponding to nucleotide 1-2883 of SEQ ID NO: 34, is not included. The first nucleotide of the variant specific sequences is shaded.

SEQ ID NO: 7
GGAAACAGAAGTACCTGTGCGCCAGCAGAAATGATTGCACTATTGATAAA

TTCCGAAGGAAAAATTGTCCATCTTGTCGTCTTCGGAAATGTTATGAAGC

AGGGATGACTCTGGGAACTAGAATTCCAAAGACCCTCAGGCTGG

TGATGCAAGTGGGAAGTCTCATTTCTGAGAAGTGCTGCTTCCTACCCACA

ATTCTTTGATAGCTGAGTGCTTTAGCTGATCTGCATAACTGAGGTGTGCA

CCAAGGAGCAGAATTACTCTATAAATTTTGGCATCAACATGTGCAACTTG

TGACTCAGCACTTTGAAACTCTGGGGATTTTTTTGTTTGGTTGGTTTTTG

TTTTAAGATGTCCTGTGGTATAGTGGAAATAGTACAATAGACTCAGATAC

AGAGAGGCCTTGTTTCTAGTCTTGGTTCTGTCACTTACTATCTTGATGTC

CTTGCACAAATCACCAGACCTCTCTGAGCCTCAGTTTCTCCAACCACACT

GTGGGAATAATAAAATCTTTTTTACGGCATTGTTGTAAGTATGCAGAGAA

ACTGGTACACAGTAGCCACACAATCAATGTCACCGTACCCTTCAGCCCTT

CTTTTGTGGATGAAAAATGGTCTTTGTGCTCCCAGTCACCACTGGGGTCT

GTTCTCTCTCTCTGCTGTTACAGTGTGGCTTTGGTTCTTGTTTCTTTG

TTCTTTGGTCTGTAAATTACCCTTGAAACAACCCTTGAAATTTCCACTCC

ATGACCTAAATCGTCATCCCTAAATTGGTTACATACATATTTGGTGACAC

TTTGGAGGGGAAAAGCTTTATGTCTCTCTAACGTGTAGTTCTTAAGGGAA

TTTGCATATGGAAAAAACAGAGACTGCGTCTCTTAATTCCTCC

SEQ ID NO: 7 corresponds to the nucleotide sequence of transcript AR V6. Most of the upstream sequence common to all androgen receptors, corresponding to nucleotide 1-2883 of SEQ ID NO: 34, is not included. The first nucleotide of the variant specific sequences is shaded.

SEQ ID NO: 39
GGAAACAGAAGTACCTGTGCGCCAGCAGAAATGATTGCACTATTGATAAA

TTCCGAAGGAAAAATTGTCCATCTTGTCGTCTTCGGAAATGTTATGAAGC

```
AGGGATGACTCTGGGAĜCAGGCAGCAGAGTGTCATAAAGAATTAA

CAACGTGGAACTCAGTTACTGGGATTTCTTCCATTCTCCTTTGATTCTCT

AGACTAGAATTCCAAAGACCCTCAGGCTGGTGATGCAAGTGGGAAGTCTC

ATTTCTGAGAAGTGCTGCTTCCTACCCACAATTCTTTGATAGCTGAGTGC

TTTAGCTGATCTGCATAACTGAGGTGTGCACCAAGGAGCAGAATTACTCT

ATAAATTTTGGCATCAACATGTGCAACTTGTGACTCAGCACTTTGAAACT

CTGGGGATTTTTTGTTTGGTTGGTTTTTGTTTTAAGATGTCCTGTGGTA

TAGTGGAAATAGTACAATAGACTCAGATACAGAGAGGCCTTGTTTCTAGT

CTTGGTTCTGTCACTTACTATCTTGATGTCCTTGCACAAATCACCAGACC

TCTCTGAGCCTCAGTTTCTCCAACCACACTGTGGGAATAATAAAATCTTT

TTTACGGCATTGTTGTAAGTATGCAGAGAAACTGGTACACAGTAGCCACA

CAATCAATGTCACCGTACCCTTCAGCCCTTCTTTTGTGGATGAAAAATGG

TCTTTGTGCTCCCAGTCACCACTGGGGTCTGTTCTCTCTCTCTGCTGT

TACAGTGTGGCTTTGGTTCTTGTTTCTTTGTTCTTTGGTCTGTAAATTAC

CCTTGAAACAACCCTTGAAATTTCCACTCCATGACCTAAATCGTCATCCC

TAAATTGGTTACATACATATTTGGTGACACTTTGGAGGGGAAAAGCTTTA

TGTCTCTCTAACGTGTAGTTCTTAAGGGAATTTGCATATGGAAAAA<u>ACAG</u>

<u>AGACTGCGTCTCTTAATTCCTCC</u>
```

SEQ ID NO: 39 corresponds to the nucleotide sequence of transcript AR V8. Most of the upstream sequence common to all androgen receptors, corresponding to nucleotide 1-2822 of SEQ ID NO: 34, is not included. The first nucleotide of the variant specific sequences is shaded.

```
TGTCACTATGGAGCTCTCACATGTGGAAGCTGCAAGGTCTTCTTCAAAAG

AGCCGCTGAAGGGAAACAGAAGTACCTGTGCGCCAGCAGAAATGATTGCA

CTATTGATAAATTCCGAAGGAAAAATTGTCCATCTTGTCGTCTTCGGAAA

TGTTATGAAGCAGGGATGACTCTGGGAĜACAACTTACCTGAGCAA

GCTGCTTTTTGGAGACATTTGCACATCTTTTGGGATCACGTTGTTAAGAA

GTAGAACTAAGGGAAAAACACGCAGCCACCCAGAAATCGGTAGAGCCTTC

AGCTCATCTGTTATTAATATTTCTGTGACAACAGATATCTAGGAAGTAAA

CAGGAAATTGCATCGCTATCCTGCATCACCTTTTTTGGAATCAGGTTCCA

TTCTTCTCAGTCCAGTTCAACCTTGTGATACTTTTTAGATCTCAACCAAG

GCATAGAAATATATTTTCCCTTGCTTAATACCCCATGGAACCAATGCCCC

TGTGGTTGAAGTAAAAATTGATTGTTGAGGGACATTTCAGCCCTCTAGCA

GTCAACAATTAAAAACATGTAAGCACCGAGCACCTGCAGAAAACTTGGAC

TGGCATTTGGATCTAAGAAGAAAATCTGCATCTTGACCAAGATGAAAAGT

CACCAGCCCAAGCTTGTGCAGTGAAGTGTCATGTTGGCCACAATGAAACT

GAAAGAGACTGATGACTCTCCTCAGGGTGGAAAATGAGGCATGGAAGCTT

TGATTAGTGAGCTGTTAGGCACACAGAACATTAATTTCAAAGCATTCTCAT

CTCCAGTCTGAGTAATAATGCTTATAGTATTATGCAATTGTTTGGCTGCT

GCAAGAAATTCAGCAGACTCCAACAAGTAGTCTTTCTTGGTCTCTGAGTG

ACTGTAACTTAAATTCTACCTCCCTTCTCTTCTCCTACATCTTCTCACTC

CCCACCCCACCCCCACATACACACAATTCTTGTCCACTATGTTCAGAGAG

ATGCACGCACACATATATATGTATATATATAGTATATTTGTCAATAAAGC

AGAAAAGAAGAAAAAACTCCAAGTAAACAATTTTCCATTTCCCCATCTCA

CTTCTGTCTTACAAGTGGATAGGAAAAGAAAAACCCCCAGTAAAAAATGG

CAACCGCCCACCTCCCCAACTTTACATGCTGCTTCCTATGTTAGAGGATC

TGTCTTAGGCATCTGATTATGGAGCCTGCTAGATACAAGCCCGTATTTAG

ACTGCTACAGTCAACAATGTCTCTCTTTCATACTAGAAAAATTCC
```

In certain examples, the androgen receptor variant nucleic acid comprises SEQ ID NO: 1, or fragments thereof. In other examples, the androgen receptor variant nucleic acid comprises SEQ ID NO: 39. In other examples, the androgen receptor variant nucleic acid comprises SEQ ID NO: 2.

In certain examples, the androgen receptor variant polypeptide comprises a sequence selected from one or more of SEQ ID NO: 8, SEQ ID NO: 40, SEQ ID NO: 9, SEQ ID NO: 10, SEQ ID NO; 11, SEQ ID NO; 12, SEQ ID NO: 13 and SEQ ID NO: 14 or fragments thereof. The sequences are shown below:

SEQ ID NO: 8

SEQ ID NO: 8 corresponds to the AR-V7 protein sequence. In SEQ ID NO: 8, most of the n-terminal AR NTD and AR DBD sequences common to all AR proteins (amino acid 1-569 of SEQ ID NO: 35) are not included. The bold sequence corresponds to amino acids encoded by exon 2, the underlined sequence corresponds to amino acids encoded by exon 3, followed by variant specific sequence in italics.

SEQ ID NO: 9
C H Y G A L T C G S C K V F F K R A A E <u>G K Q K Y</u>
<u>L C A S R N D C T I D K F R R K N C P S C R L R K</u>
<u>C Y E A G M T L G</u> *E K F R V G N C K H L K M T R P*
Stop SEQ ID NO: 9 corresponds to the AR-V1 protein sequence. In SEQ ID NO: 9, most of the N-terminal AR NTD and AR DBD sequences common to all AR proteins (amino acid 1-569 of SEQ ID NO: 35) are not included. The bold sequence corresponds to amino acids encoded by exon 2, the underlined sequence corresponds to amino acids encoded by exon 3, followed by variant specific sequence in italics.

SEQ ID NO: 10
C H Y G A L T C G S C K V F F K R A A E <u>G K Q K Y</u>
<u>L C A S R N D C T I D K F R R K N C P S C R L R K</u>
<u>C Y E A G M T L G</u> *A V V V S E R I L R V F G V S E*
*W L P* Stop SEQ ID NO: 10 corresponds to the AR-V2 protein sequence. In SEQ ID NO: 10, most of the n-terminal AR NTD and AR DBD sequences common to all AR proteins (amino acid 1-569 of SEQ ID NO: 35) are not included. The bold sequence corresponds to amino acids encoded by exon 2, the underlined sequence corresponds to amino acids encoded by exon 3, followed by variant specific sequence in italics. Peptide sequences encoded by exon 3 are duplicated.

SEQ ID NO: 11
C H Y G A L T C G S C K V F F K R A A E G K Q K Y

L C A S R N D C T I D K F R R K N C P S C R L R K

C Y E A G M T L G G K Q K Y L C A S R N D C T I D

K F R R K N C P S C R L R K C Y E A G M T L G A *V*

*V V S E R I L R V F G V S E W L P* Stop

SEQ ID NO: 11 corresponds to the AR-V3 protein sequence. In SEQ ID NO: 11, most of the n-terminal AR NTD and AR DBD sequences common to all AR proteins (amino acid 1-569 of SEQ ID NO: 35) are not included. The first amino acid of the variant specific sequence is shaded. The bold sequence corresponds to amino acids encoded by exon 2, followed by variant specific sequence in italics.

SEQ ID NO: 12
C H Y G A L T C G S C K V F F K R A A *E G F F R M*

*N K L K E S S D T N P K P Y C M A A P M G L T E N*

*N R N R K K S Y R E T N L K A V S W P L N H T*

Stop

SEQ ID NO: 12 corresponds to the AR-V4 protein sequence. In SEQ ID NO: 12, most of the n-terminal AR NTD and AR DBD sequences common to all AR proteins (amino acid 1-569 of SEQ ID NO: 35) are not included. The bold sequence corresponds to amino acids encoded by exon 2, the underlined sequence corresponds to amino acids encoded by exon 3, followed by variant specific sequence in italics.

SEQ ID NO: 13
C H Y G A L T C G S C K V F F K R A A E G K Q K Y

L C A S R N D C T I D K F R R K N C P S C R L R K

C Y E A G M T L G *G F F R M N K L K E S S D T N P*

*K P Y C M A A P M G L T E N N R N R K K S Y R E*

*T N L K A V S W P L N H T* Stop

SEQ ID NO: 13 corresponds to the AR-V5 protein sequence. In SEQ ID NO: 13 most of the n-terminal AR NTD and AR DBD sequences common to all AR proteins (amino acid 1-589 of SEQ ID NO: 35) are not included. Underlined sequence corresponds to amino acids encoded by exon 3, followed by variant specific sequence in italics.

SEQ ID NO: 14
G K Q K Y L C A S R N D C T I D K F R R K N C P S

C R L R K C Y E A G M T L G *D* Stop

SEQ ID NO: 14 corresponds to AR-V6 protein sequence. In SEQ ID NO: 14. most of the n-terminal AR NTD and AR DBD sequences common to all AR proteins (amino acid 1-589 of SEQ ID NO: 35) are not included. Underlined sequence corresponds to amino acids encoded by exon 3, followed by variant specific sequence in italics.

SEQ ID NO: 40
G K Q K Y L C A S R N D C T I D K F R R K N C P S

C R L R K C Y E A G M T L G A *G S R V S* Stop

SEQ ID NO: 40 corresponds to the AR-V8 protein sequence. In SEQ ID NO: 40, most of the n-terminal AR NTD and AR DBD sequences common to all AR proteins (amino acid 1-569 of SEQ ID NO: 35) are not included. The bold sequence corresponds to amino acids encoded by exon 2, the underlined sequence corresponds to amino acids encoded by exon 3, followed by variant specific sequence in italics.

C H Y G A L T C G S C K V F F K R A A E G K Q K Y

L C A S R N D C T I D K F R R K N C P S C R L R K

C Y E A G M T L G *D N L P E Q A A F W R H L H I F*

*W D H V V K K* Stop

Diagnostics and Prognostics

Prostate cancer depends on androgenic signaling for growth and survival. Androgens exert their cellular and physiologic effects through binding to the androgen receptor. It is a finding of the present invention that certain prostate cancer cells express higher levels of androgen receptor variants, in particular AR-V I-AR-V7 than corresponding normal tissues. Accordingly, expression levels of an androgen receptor variant nucleic acid molecule or polypeptide are correlated with a particular androgen related disease state (e.g., prostate cancer), and thus are useful in diagnosis. Accordingly, the present invention provides a number of diagnostic assays that are useful for the identification or characterization of an androgen related disease or disorder, e.g. prostate cancer.

In embodiments of the invention, a patient having an androgen related disease or disorder, e.g. prostate cancer, will show an increase in the expression of an androgen receptor variant nucleic acid molecule. Alterations in gene expression are detected using methods known to the skilled artisan and described herein. Such information can be used to diagnose a androgen related disease or disorder, e.g. prostate cancer. In another embodiment, an alteration in the expression of an androgen receptor variant nucleic acid molecule is detected using polymerase chain reaction (PCR), for example, real time PCR or semi quantitative real time PCR to detect changes in gene expression.

Primers used for amplification of an androgen receptor variant nucleic acid molecule, including but not limited to those primer sequences described herein, are useful in diagnostic methods of the invention. The primers of the invention embrace oligonucleotides of sufficient length and appropriate sequence so as to provide specific initiation of polymerization on a significant number of nucleic acids. Specifically, the term "primer" as used herein refers to a sequence comprising two or more deoxyribonucleotides or ribonucleotides, preferably more than three, and most preferably more than 8, which sequence is capable of initiating synthesis of a primer extension product, which is substantially complementary to a locus strand. The primer must be sufficiently long to prime the synthesis of extension products in the presence of the inducing agent for polymerization. The exact length of primer will depend on many factors, including temperature, buffer, and nucleotide composition. Primers of the invention are designed to be "substantially" complementary to each strand of the genomic locus to be amplified and include the appropriate G or C nucleotides as discussed above. This means that the primers must be sufficiently complementary to hybridize with their respective strands under conditions that allow the agent for polymerization to perform. In other words, the primers should have sufficient complementarity with the 5' and 3' flanking sequences to hybridize therewith and permit amplification of the genomic locus. While exemplary primers are provided herein, it is understood that any primer that hybridizes with the target sequences of the invention are useful in the method of the invention for detecting androgen receptor variant nucleic acid molecules.

Exemplary primer sets useful in the invention are shown below:

```
(P1):
                                    (SEQ ID NO: 15)
TGTCACTATGGAGCTCTCACATGTGG
and
                                    (SEQ ID NO: 16)
CACCTCTCAAATATGCTAGACGAATCTGT;

(P2)
                                    (SEQ ID NO: 17)
TGTCACTATGGAGCTCTCACATGTGG
and
                                    (SEQ ID NO: 18)
GTACTCATTCAAGTATCAGATATGCGGTATCAT;

(P3)
                                    (SEQ ID NO: 19)
TGTCACTATGGAGCTCTCACATGTGG
and
                                    (SEQ ID NO: 20)
CTGTGGATCAGCTACTACCTTCAGCTC;

(P4)
                                    (SEQ ID NO: 21)
GTTGCTCCCGCAAGTTTCCTTCTC
and
                                    (SEQ ID NO: 22)
CTGTTGTGGATGAGCAGCTGAGAGTCT;

(P5)
                                    (SEQ ID NO: 23)
GTTGCTCCCGCAAGTTTCCTTCTC
and
                                    (SEQ ID NO: 24)
TTTGAATGAGGCAAGTCAGCCTTTCT;

(P6)
                                    (SEQ ID NO: 25)
CCATCTTGTCGTCTTCGGAAATGTTATGAAGC
and
                                    (SEQ ID NO: 26)
CTGTTGTGGATGAGCAGCTGAGAGTCT;

(P7)
                                    (SEQ ID NO: 27)
CCATCTTGTCGTCTTCGGAAATGTTATGAAGC
and
                                    (SEQ ID NO: 28)
TTTGAATGAGGCAAGTCAGCCTTTCT;

(P8)
                                    (SEQ ID NO: 29)
CCATCTTGTCGTCTTCGGAAATGTTATGAAGC
and
                                    (SEQ ID NO: 30)
AGCTTCTGGGTTGTCTCCTCAGTGG;
and (P9)
                                    (SEQ ID NO: 37)
Tgtcactatggagctctcacatgtgg
and
                                    (SEQ ID NO: 38)
Cattgtggccaacatgacacttca.
```

In one embodiment, androgen receptor variant-specific primers amplify a desired genomic target using the polymerase chain reaction (PCR), in particular semi quantitative RT-PCR. The amplified product is then detected using standard methods known in the art. In one embodiment, a PCR product (i.e., amplicon) or real-time PCR product is detected by probe binding. In one embodiment, probe binding generates a fluorescent signal, for example, by coupling a fluorogenic dye molecule and a quencher moiety to the same or different oligonucleotide substrates (e.g., TaqMan® (Applied Biosystems, Foster City, Calif., USA), Molecular Beacons (see, for example, Tyagi et al., Nature Biotechnology 14(3):303-8, 1996), Scorpions® (Molecular Probes Inc., Eugene, Oreg., USA)). In another example, a PCR product is detected by the binding of a fluorogenic dye that emits a fluorescent signal upon binding (e.g., SYBR® Green (Molecular Probes)). Such detection methods are useful for the detection of an androgen receptor variant PCR product.

In another embodiment, hybridization with PCR probes that are capable of detecting an androgen receptor variant nucleic acid molecule, including genomic sequences, or closely related molecules, may be used to hybridize to a nucleic acid sequence derived from a patient having an androgen related disease or disorder, e.g. prostate cancer. The specificity of the probe determines whether the probe hybridizes to a naturally occurring sequence, allelic variants, or other related sequences. Hybridization techniques may be used to identify mutations indicative of a androgen related disease or disorder, e.g. prostate cancer, or may be used to monitor expression levels of these genes (for example, by Northern analysis (Ausubel et al., supra).

The invention features methods of determining if a subject will respond to androgen therapy, the method comprising determining the level of expression or biological activity of an androgen receptor variant polypeptide in a subject sample wherein an alteration in the level of expression or biological activity relative to the expression or biological activity in a reference indicates that the subject will respond to androgen therapy.

The invention also features methods of determining if a subject will respond to androgen therapy, the method comprising determining the level of expression or biological activity of an androgen receptor variant nucleic acid in a subject sample wherein an alteration in the level of expression relative to the expression in a reference indicates that the subject will respond to androgen therapy.

In preferred embodiments, the subject has prostate cancer. In other embodiments, the subject is in remission from prostate cancer.

In certain embodiments the invention features diagnostic methods. For example a subject, for example a patient, may be diagnosed for a propensity to develop a androgen related disease or disorder, e.g. prostate cancer, by direct analysis of the sequence of an androgen receptor variant nucleic acid molecule. The sequence of an androgen receptor variant nucleic acid molecule derived from a subject is compared to a reference sequence. An alteration in the sequence of the androgen receptor variant nucleic acid molecule relative to the reference indicates that the patient has or has a propensity to develop an androgen related disease or disorder, e.g. prostate cancer.

In another approach, diagnostic methods of the invention are used to assay the expression of an androgen receptor variant polypeptide in a biological sample relative to a reference (e.g., the level of androgen receptor variant polypeptide present in a corresponding control sample, or in a sample taken before a treatment, such as surgical treatment).

In one embodiment, the level of an androgen receptor variant polypeptide is detected using an antibody that specifically binds an androgen receptor variant polypeptide. Exemplary antibodies that specifically bind an androgen receptor variant polypeptide are described herein. Such antibodies are useful for the diagnosis of an androgen related disease or disorder. Methods for measuring an antibody-androgen receptor variant complex include, for example, detection of fluorescence, luminescence, chemiluminescence, absorbance, reflectance, transmittance, birefringence or refractive index. Optical methods include microscopy (both confocal and non-confocal), imaging methods and non-imaging methods. Methods for performing these assays are readily known in the art. Useful assays include, for example, an enzyme immune assay (EIA) such as enzyme-linked immunosorbent assay (ELISA), a radioimmune assay (RIA), a Western blot assay, or a slot blot assay. These methods are also described in, e.g., Methods in Cell Biology: Antibodies in Cell Biology, volume 37 (Asai, ed. 1993); Basic and Clinical Immunology (Stites & Terr, eds., 7th ed. 1991); and Harlow & Lane, supra. Immunoassays can be used to determine the quantity of androgen receptor variant in a sample, where an increase in the level of the androgen receptor variant polypeptide is diagnostic of a patient having an androgen related disease or disorder, e.g. prostate cancer.

In general, the measurement of an androgen receptor variant polypeptide or nucleic acid molecule in a subject sample is compared with a diagnostic amount present in a reference. A diagnostic amount distinguishes between a diseased tissue or, for example a neoplastic tissue, and a control tissue. The skilled artisan appreciates that the particular diagnostic amount used can be adjusted to increase sensitivity or specificity of the diagnostic assay depending on the preference of the diagnostician. In general, any significant increase (e.g., at least about 10%, 15%, 30%, 50%, 60%, 75%, 80%, or 90%) in the level of an androgen receptor variant polypeptide or nucleic acid molecule in the subject sample relative to a reference may be used to diagnose an androgen related disease or disorder, e.g. prostate cancer. In one embodiment, the reference is the level of androgen receptor variant polypeptide or nucleic acid molecule present in a control sample obtained from a patient that does not have an androgen related disease or disorder, e.g. prostate cancer. In another embodiment, the reference is the level of androgen receptor variant polypeptide or nucleic acid molecule present in a control sample obtained from subjects with a disease of less severity, e.g., early stage non-aggressive prostate cancer. In another embodiment, the reference is a baseline level of androgen receptor variant present in a biologic sample derived from a patient prior to, during, or after treatment for an androgen related disease or disorder, e.g. prostate cancer. In yet another embodiment, the reference is a standardized curve.

Types of Biological Samples

The level of an androgen receptor variant polypeptide or nucleic acid molecule can be measured in different types of biologic samples. In one embodiment, the biologic sample is a tissue sample that includes cells of a tissue or organ. Such tissue is obtained, for example, from a biopsy. In another embodiment, the biologic sample is a biologic fluid sample (e.g., blood, blood plasma, serum, urine, seminal fluids, ascites, or cerebrospinal fluid).

In certain exemplary embodiments, the sample is from prostate.

In other certain exemplary embodiments, the sample is from a subject undergoing treatment for prostate cancer.

Patient Monitoring

The disease state or treatment of a patient having prostate cancer can be monitored using the methods and compositions of the invention. In one embodiment, a microarray is used to assay the expression profile of androgen receptor variant nucleic acid molecule. Such monitoring may be useful, for example, in assessing response of a patient to androgen therapy, in assessing the remission status of a patient, or in assessing the response of a particular drug in a patient.

Therapeutics that alter the expression of an androgen receptor variant nucleic acid molecule or androgen receptor variant polypeptide (e.g., an androgen receptor variant, for example AR-V1, AR-V2, AR-V3, AR-V4, AR-V5, AR-V6, AR-V7, AR-V8, or fragments thereof), may be useful in the invention.

Kits

The invention also provides kits for the diagnosis or monitoring of an androgen related disease or disorder, e.g. prostate cancer, in a biological sample obtained from a subject. In one embodiment, the kit detects an increase in the expression of an androgen receptor variant nucleic acid molecule or polypeptide relative to a reference level of expression. In another embodiment, the kit detects an alteration in the sequence of an androgen receptor variant nucleic acid molecule derived from a subject relative to a reference sequence. In related embodiments, the kit includes reagents for monitoring the expression of an androgen receptor variant nucleic acid molecule, such as primers or probes that hybridize to an androgen receptor variant nucleic acid molecule. In other embodiments, the kit includes an antibody that binds to an androgen receptor variant polypeptide.

Optionally, the kit includes directions for monitoring an androgen receptor variant nucleic acid molecule or polypeptide levels in a biological sample derived from a subject. In other embodiments, the kit comprises a sterile container which contains the primer, probe, antibody, or other detection regents; such containers can be boxes, ampules, bottles, vials, tubes, bags, pouches, blister-packs, or other suitable container form known in the art. Such containers can be made of plastic, glass, laminated paper, metal foil, or other materials suitable for holding nucleic acids. The instructions will generally include information about the use of the primers or probes described herein and their use in diagnosing an androgen related disease or disorder, e.g. prostate cancer. Preferably, the kit further comprises any one or more of the reagents described in the diagnostic assays described herein. In other embodiments, the instructions include at least one of the following: description of the primer or probe; methods for using the enclosed materials for the diagnosis of an androgen related disease or disorder, e.g. prostate cancer; precautions; warnings; indications; clinical or research studies; and/or references. The instructions may be printed directly on the container (when present), or as a label applied to the container, or as a separate sheet, pamphlet, card, or folder supplied in or with the container.

Androgen Receptor Variant Antibodies

Antibodies are well known to those of ordinary skill in the science of immunology. As used herein, the term "antibody" means not only intact antibody molecules, but also fragments of antibody molecules that retain immunogen binding ability. Such fragments are also well known in the art and are regularly employed both in vitro and in vivo. Accordingly, as used herein, the term "antibody" means not only intact immunoglobulin molecules but also the well-known active fragments F(ab')$_2$, and Fab. F(ab')$_2$, and Fab fragments which lack the Fc fragment of intact antibody, clear more rapidly from the circulation, and may have less non-specific tissue binding of an intact antibody (Wahl et al., J. Nucl. Med. 24:316-325 (1983). The antibodies of the invention comprise whole native antibodies, bispecific antibodies; chimeric antibodies; Fab, Fab', single chain V region fragments (scFv) and fusion polypeptides.

In one embodiment, an antibody that binds an androgen receptor variant polypeptide (e.g., an androgen receptor variant, for example AR-V1, AR-V2, AR-V3, AR-V4, AR-V5, AR-V6, AR-V7, AR-V8 or fragments thereof) is monoclonal. Alternatively, the antiandrogen receptor variant antibody is a polyclonal antibody. The preparation and use of polyclonal antibodies are also known the skilled artisan. The invention also encompasses hybrid antibodies, in which one pair of heavy and light chains is obtained from a first antibody, while the other pair of heavy and light chains is obtained from a different second antibody. Such hybrids may also be formed using humanized heavy and light chains. Such antibodies are often referred to as "chimeric" antibodies.

In general, intact antibodies are said to contain "Fc" and "Fab" regions. The Fc regions are involved in complement activation and are not involved in antigen binding. An antibody from which the Fc' region has been enzymatically cleaved, or which has been produced without the Fc' region, designated an "F(ab')$_2$" fragment, retains both of the antigen binding sites of the intact antibody. Similarly, an antibody from which the Fc region has been enzymatically cleaved, or which has been produced without the Fc region, designated an "Fab'" fragment, retains one of the antigen binding sites of the intact antibody. Fab' fragments consist of a covalently bound antibody light chain and a portion of the antibody heavy chain, denoted "Fd." The Fd fragments are the major determinants of antibody specificity (a single Fd fragment may be associated with up to ten different light chains without altering antibody specificity). Isolated Fd fragments retain the ability to specifically bind to immunogenic epitopes.

Antibodies can be made by any of the methods known in the art utilizing androgen receptor variant polypeptides unique to each of the variants (e.g., an androgen receptor variant, for example AR-V1, AR-V2, AR-V3, AR-V4, AR-V5, AR-V6, AR-V7, AR-V8, or fragments thereof), or immunogenic fragments thereof, as an immunogen. One method of obtaining antibodies is to immunize suitable host animals with an immunogen and to follow standard procedures for polyclonal or monoclonal antibody production. The immunogen will facilitate presentation of the immunogen on the cell surface. Immunization of a suitable host can be carried out in a number of ways. Nucleic acid sequences encoding an androgen receptor variant polypeptide (e.g., an androgen receptor variant, for example AR-V1, AR-V2, AR-V3, AR-V4, AR-V5, AR-V6, AR-V7, or fragments thereof), or immunogenic fragments thereof, can be provided to the host in a delivery vehicle that is taken up by immune cells of the host. The cells will in turn express the receptor on the cell surface generating an immunogenic response in the host. Alternatively, nucleic acid sequences encoding an androgen receptor variant polypeptide (e.g., an androgen receptor variant, for example AR-V1, AR-V2, AR-V3, AR-V4, AR-V5, AR-V6, AR-V7, AR-V-8 or fragments thereof), or immunogenic fragments thereof, can be expressed in cells in vitro, followed by isolation of the receptor and administration of the receptor to a suitable host in which antibodies are raised.

Using either approach, antibodies can then be purified from the host. Antibody purification methods may include salt precipitation (for example, with ammonium sulfate), ion exchange chromatography (for example, on a cationic or anionic exchange column preferably run at neutral pH and eluted with step gradients of increasing ionic strength), gel filtration chromatography (including gel filtration HPLC), and chromatography on affinity resins such as protein A, protein G, hydroxyapatite, and anti-immunoglobulin.

Antibodies can be conveniently produced from hybridoma cells engineered to express the antibody. Methods of making hybridomas are well known in the art. The hybridoma cells can be cultured in a suitable medium, and spent medium can be used as an antibody source. Polynucleotides encoding the antibody of interest can in turn be obtained from the hybridoma that produces the antibody, and then the antibody may be produced synthetically or recombinantly from these DNA sequences. For the production of large amounts of antibody, it is generally more convenient to obtain an ascites fluid. The method of raising ascites generally comprises injecting hybridoma cells into an immunologically naive histocompatible or immunotolerant mammal, especially a mouse. The mammal may be primed for ascites production by prior administration of a suitable composition; e.g., Pristane.

Monoclonal antibodies (Mabs) produced by methods of the invention can be "humanized" by methods known in the art. "Humanized" antibodies are antibodies in which at least part of the sequence has been altered from its initial form to render it more like human immunoglobulins. Techniques to humanize antibodies are particularly useful when non-human animal (e.g., murine) antibodies are generated. Examples of methods for humanizing a murine antibody are provided in U.S. Pat. Nos. 4,816,567, 5,530,101, 5,225,539, 5,585,089, 5,693,762 and 5,859,205.

In certain preferred embodiments, the antibody specifically binds to an androgen receptor variant-7 (AR-V7) protein. In other embodiments, the antibody specifically binds to an androgen receptor variant-1 (AR-V1) protein. In other certain preferred embodiments, the antibody specifically binds to an androgen receptor variant-8 (AR-V8) protein.

Preferably, the antibody binds to a CKHLKMRP epitope of an AR-V7 polypeptide, corresponding to SEQ ID NO: 33.

Androgen Receptor Variant Polypeptide Expression

In general, androgen receptor variant polypeptides, variants, and fragments thereof may be produced by transformation of a suitable host cell with all or part of a polypeptide-encoding nucleic acid molecule or fragment thereof in a suitable expression vehicle.

Those skilled in the field of molecular biology will understand that any of a wide variety of expression systems may be used to provide the recombinant protein. The precise host cell used is not critical to the invention. A polypeptide of the invention may be produced in a prokaryotic host (e.g., *E. coli*) or in a eukaryotic host (e.g., *Saccharomyces cerevisiae*, insect cells, e.g., Sf21 cells, or mammalian cells, e.g., NIH 3T3, HeLa, or preferably COS cells). Such cells are available from a wide range of sources (e.g., the American Type Culture Collection, Rockland, Md.; also, see, e.g., Ausubel et al., supra). The method of transformation or transfection and the choice of expression vehicle will depend on the host system selected. Transformation and transfection methods are described, e.g., in Ausubel et al. (supra); expression vehicles may be chosen from those provided, e.g., in Cloning Vectors: A Laboratory Manual (P. H. Pouwels et al., 1985, Supp. 1987).

A variety of expression systems exist for the production of the polypeptides of the invention. Expression vectors useful for producing such polypeptides include, without limitation, chromosomal, episomal, and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof.

For example, one particular bacterial expression system for polypeptide production is the *E. coli* pET expression system (Novagen, Inc., Madison, Wis.). According to this expression system, DNA encoding a polypeptide is inserted into a pET vector in an orientation designed to allow expression. Since the gene encoding such a polypeptide is under the control of the T7 regulatory signals, expression of the polypeptide is achieved by inducing the expression of T7 RNA polymerase in the host cell. This is typically achieved using host strains that express T7 RNA polymerase in response to IPTG induction. Once produced, recombinant polypeptide is then isolated according to standard methods known in the art, for example, those described herein.

Another bacterial expression system for polypeptide production is the pGEX expression system (Pharmacia). This system employs a GST gene fusion system that is designed for high-level expression of genes or gene fragments as fusion proteins with rapid purification and recovery of functional gene products. The protein of interest is fused to the carboxyl terminus of the glutathione S-transferase protein from *Schistosoma japonicum* and is readily purified from bacterial lysates by affinity chromatography using Glutathione Sepharose 4B. Fusion proteins can be recovered under mild conditions by elution with glutathione. Cleavage of the glutathione S-transferase domain from the fusion protein is facilitated by the presence of recognition sites for site-specific proteases upstream of this domain. For example, proteins expressed in pGEX-2T plasmids may be cleaved with thrombin; those expressed in pGEX-3X may be cleaved with factor Xa.

Once the recombinant polypeptide of the invention is expressed, it is isolated, e.g., using affinity chromatography. In one example, an antibody (e.g., produced as described herein) raised against a polypeptide of the invention may be attached to a column and used to isolate the recombinant polypeptide. Lysis and fractionation of polypeptide-harboring cells prior to affinity chromatography may be performed by standard methods (see, e.g., Ausubel et al., supra).

Once isolated, the recombinant protein can, if desired, be further purified, e.g., by high performance liquid chromatography (see, e.g., Fisher, Laboratory Techniques In Biochemistry and Molecular Biology, eds., Work and Burdon, Elsevier, 1980). Polypeptides of the invention, particularly short peptide fragments, can also be produced by chemical synthesis (e.g., by the methods described in Solid Phase Peptide Synthesis, 2nd ed., 1984 The Pierce Chemical Co., Rockford, Ill.). These general techniques of polypeptide expression and purification can also be used to produce and isolate useful peptide fragments or analogs (described herein).

Androgen Receptor Variant Polypeptides and Analogs

Also included in the invention are androgen receptor variant polypeptides, variants, or fragments thereof containing at least one alteration relative to a reference sequence. Such alterations include certain polymorphic variations, mutations, deletions, insertions, or post-translational modifications. The invention further includes analogs of any naturally-occurring polypeptide of the invention. Analogs can differ from naturally-occurring polypeptides of the invention by amino acid sequence differences, by post-translational modifications, or by both. Analogs of the invention will generally exhibit at least 85%, more preferably 90%, and most preferably 95% or even 99% identity with all or part of a naturally-occurring amino acid sequence of the invention. The length of sequence comparison is at least 10, 13, 15 amino acid residues, preferably at least 25 amino acid residues, and more preferably more than 35 amino acid residues. Again, in an exemplary approach to determining the degree of identity, a BLAST program may be used, with a probability score between $e^{-3}$ and $e^{-100}$ indicating a closely related sequence. Modifications include in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally-occurring polypeptides of the invention by alterations in primary sequence. These include genetic variants, both natural and induced (for example, resulting from random mutagenesis by irradiation or exposure to ethanemethylsulfate or by site-specific mutagenesis as described in Sambrook, Fritsch and Maniatis, Molecular Cloning: A Laboratory Manual (2d ed.), CSH Press, 1989, or Ausubel et al., supra). Also included are cyclized peptides, molecules, and analogs which contain residues other than L-amino acids, e.g., D-amino acids or non-naturally occurring or synthetic amino acids.

In addition to full-length polypeptides, the invention also includes fragments of any one of the polypeptides of the invention. As used herein, the term "a fragment" means at least 5, 10, 13, or 15 amino acids. In other embodiments a fragment is at least 20 contiguous amino acids, at least 30 contiguous amino acids, or at least 50 contiguous amino acids, and in other embodiments at least 60 to 80 or more contiguous amino acids. Fragments of the invention can be generated by methods known to those skilled in the art or may result from normal protein processing (e.g., removal of amino acids from the nascent polypeptide that are not required for biological activity or removal of amino acids by alternative mRNA splicing or alternative protein processing events).

Androgen Receptor Variant Polynucleotides

In general, the invention includes any nucleic acid sequence encoding an androgen receptor variant polypeptide (e.g., androgen receptor variant, for example AR-V1, AR-V2, AR-V3, AR-V4, AR-V5, AR-V6, AR-V7, AR-V8 or fragments thereof). Also included in the methods of the invention are any nucleic acid molecule containing at least one strand that hybridizes with such a nucleic acid sequence (e.g., an inhibitory nucleic acid molecule, such as a dsRNA, siRNA, shRNA, or antisense molecule). An isolated nucleic acid molecule can be manipulated using recombinant DNA techniques well known in the art. Thus, a nucleotide sequence contained in a vector in which 5' and 3' restriction sites are known, or for which polymerase chain reaction (PCR) primer sequences have been disclosed, is considered isolated, but a nucleic acid sequence existing in its native state in its natural host is not. An isolated nucleic acid may be substantially purified, but need not be. For example, a nucleic acid molecule that is isolated within a cloning or expression vector may comprise only a tiny percentage of the material in the cell in which it resides. Such a nucleic acid is isolated, however, as the term is used herein, because it can be manipulated using standard techniques known to those of ordinary skill in the art.

Androgen Receptor Variant Polynucleotide Therapy

Polynucleotide therapy featuring a polynucleotide encoding an androgen receptor variant protein, variant, or fragment thereof is another therapeutic approach for treating a androgen related disease or disorder, e.g. prostate cancer. Such nucleic acid molecules can be delivered to cells of a subject having an androgen related disease or disorder, e.g. prostate cancer. The nucleic acid molecules must be delivered to the cells of a subject in a form in which they can be taken up so that therapeutically effective levels of an androgen receptor variant protein (e.g., androgen receptor variant, for example AR-V1, AR-V2, AR-V3, AR-V4, AR-V5, AR-V6, AR-V7, AR-V8 or fragments thereof) or fragment thereof can be produced.

Transducing viral (e.g., retroviral, adenoviral, and adeno-associated viral) vectors can be used for somatic cell gene therapy, especially because of their high efficiency of infection and stable integration and expression (see, e.g., Cayouette et al., Human Gene Therapy 8:423-430, 1997; Kido et al., Current Eye Research 15:833-844, 1996; Bloomer et al., Journal of Virology 71:6641-6649, 1997; Naldini et al., Science 272:263-267, 1996; and Miyoshi et al., Proc. Natl. Acad. Sci. U.S.A. 94:10319, 1997). For example, a polynucleotide encoding an androgen receptor variant protein, variant, or a fragment thereof, can be cloned into a retroviral vector and expression can be driven from its endogenous promoter, from the retroviral long terminal repeat, or from a promoter specific for a target cell type of interest. Other viral vectors that can be used include, for example, a vaccinia virus, a bovine papilloma virus, or a herpes virus, such as Epstein-Barr Virus (also see, for example, the vectors of Miller, Human Gene Therapy 15-14, 1990; Friedman, Science 244:1275-1281, 1989; Eglitis et al., BioTechniques 6:608-614, 1988; Tolstoshev et al., Current Opinion in Biotechnology 1:5561, 1990; Sharp, The Lancet 337:1277-1278, 1991; Cornetta et al., Nucleic Acid Research and Molecular Biology 36:311-322, 1987; Anderson, Science 226:401-409, 1984; Moen, Blood Cells 17:407-416, 1991; Miller et al., Biotechnology 7:980-990, 1989; Le Gal La Salle et al., Science 259:988-990, 1993; and Johnson, Chest 107:77S-83S, 1995). Retroviral vectors are particularly well developed and have been used in clinical settings (Rosenberg et al., N. Engl. J. Med 323:370, 1990; Anderson et al., U.S. Pat. No. 5,399,346). Most preferably, a viral vector is used to administer an androgen receptor variant polynucleotide systemically.

Non-viral approaches can also be employed for the introduction of therapeutic to a cell of a patient diagnosed as having an androgen related disease or disorder, e.g. prostate cancer. For example, a nucleic acid molecule can be introduced into a cell by administering the nucleic acid in the presence of lipofection (Feigner et al., Proc. Natl. Acad. Sci. U.S.A. 84:7413, 1987; Ono et al., Neuroscience Letters 17:259, 1990; Brigham et al., Am. J. Med. Sci. 298:278, 1989; Staubinger et al., Methods in Enzymology 101:512, 1983), asialoorosomucoid-polylysine conjugation (Wu et al., Journal of Biological Chemistry 263:14621, 1988; Wu et al., Journal of Biological Chemistry 264:16985, 1989), or by micro-injection under surgical conditions (Wolff et al., Science 247:1465, 1990). Preferably the nucleic acids are administered in combination with a liposome and protamine.

Gene transfer can also be achieved using non-viral means involving transfection in vitro. Such methods include the use of calcium phosphate, DEAE dextran, electroporation, and protoplast fusion. Liposomes can also be potentially beneficial for delivery of DNA into a cell. Transplantation of normal genes into the affected tissues of a patient can also be accomplished by transferring a normal nucleic acid into a cultivatable cell type ex vivo (e.g., an autologous or heterologous primary cell or progeny thereof), after which the cell (or its descendants) are injected into a targeted tissue.

cDNA expression for use in polynucleotide therapy methods can be directed from any suitable promoter (e.g., the human cytomegalovirus (CMV), simian virus 40 (SV40), or metallothionein promoters), and regulated by any appropriate mammalian regulatory element. For example, if desired, enhancers known to preferentially direct gene expression in specific cell types can be used to direct the expression of a nucleic acid. The enhancers used can include, without limitation, those that are characterized as tissue- or cell-specific enhancers. Alternatively, if a genomic clone is used as a therapeutic construct, regulation can be mediated by the cognate regulatory sequences or, if desired, by regulatory sequences derived from a heterologous source, including any of the promoters or regulatory elements described above.

Another therapeutic approach included in the invention involves administration of a recombinant therapeutic, such as a recombinant androgen receptor variant protein, variant, or fragment thereof, either directly to the site of a potential or actual disease-affected tissue or systemically (for example, by any conventional recombinant protein administration technique). The dosage of the administered protein depends on a number of factors, including the size and health of the individual patient. For any particular subject, the specific dosage regimes should be adjusted over time according to the individual need and the professional judgment of the person administering or supervising the administration of the compositions.

Screening Assays

As reported herein, the expression of an androgen receptor variant polypeptide is increased in neoplastic tissues, and in particular examples in neoplastic tissues from patients with progressive diseases. Accordingly, compounds that modulate the expression or activity of an androgen receptor variant polypeptide, variant, or fragment thereof are useful in the methods of the invention for the treatment or prevention of an androgen related disease or disorder, such as prostate cancer, or advanced prostate cancer. Any number of methods are available for carrying out screening assays to identify such compounds. In one approach, candidate compounds are identified that specifically bind to and alter the activity of a polypeptide of the invention (e.g., an androgen receptor variant activity). Methods of assaying such biological activities are known in the art and are described herein. The efficacy of such a candidate compound is dependent upon its ability to interact with an androgen receptor variant polypeptide, variant, or fragment. Such an interaction can be readily assayed using any number of standard binding techniques and functional assays (e.g., those described in Ausubel et al., supra). For example, a candidate compound may be tested in vitro for interaction and binding with a polypeptide of the invention. Standard methods for perturbing or reducing androgen receptor variant expression include mutating or deleting an endogenous androgen receptor variant sequence, interfering with androgen receptor variant expression using RNAi, or microinjecting an androgen receptor variant-expressing cell with an antibody that binds androgen receptor variant and interferes with its function.

Potential agonists and antagonists of an androgen receptor variant polypeptide include organic molecules, peptides, peptide mimetics, polypeptides, nucleic acid molecules (e.g., double-stranded RNAs, siRNAs, antisense polynucleotides), and antibodies that bind to a nucleic acid sequence or polypeptide of the invention and thereby inhibit or decrease its activity. Potential antagonists also include small molecules that bind to the androgen receptor variant polypeptide thereby preventing binding to cellular molecules with which the androgen receptor variant polypeptide normally interacts, such that the normal biological activity of the androgen receptor variant polypeptide is reduced or inhibited. Small molecules of the invention preferably have a molecular weight below 2,000 daltons, more preferably between 300 and 1,000 daltons, and most preferably between 400 and 700 daltons. It is preferred that these small molecules are organic molecules.

For example, a recombinant polypeptide of the invention may be purified by standard techniques from cells engineered to express the polypeptide (e.g., those described above) and may be immobilized on a column. A solution of candidate compounds is then passed through the column, and a compound specific for the androgen receptor variant polypeptide is identified on the basis of its ability to bind to the androgen receptor variant polypeptide and be immobilized on the column. To isolate the compound, the column is washed to remove non-specifically bound molecules, and the compound of interest is then released from the column and collected.

In one particular example, methods may be used to isolate a compound bound to a polypeptide microarray. Compounds isolated by this method (or any other appropriate method) may, if desired, be further purified (e.g., by high performance liquid chromatography). In addition, these candidate compounds may be tested for their ability to alter the biological activity of an androgen receptor variant polypeptide (e.g., androgen receptor variant, for example AR-V1, AR-V2, AR-V3, AR-V4, AR-V5, AR-V6, AR-V7, AR-V8 or fragments thereof).

Any in vivo protein interaction detection system, for example, any two-hybrid assay may be utilized to identify compounds that interact with an androgen receptor variant polypeptide. Interacting compounds isolated by this method (or any other appropriate method) may, if desired, be further purified (e.g., by high performance liquid chromatography). Compounds isolated by any approach described herein may be used as therapeutics to treat a androgen related disease or disorder, e.g. prostate cancer in a human patient.

In addition, compounds that inhibit the expression of an androgen receptor variant nucleic acid molecule whose expression is increased in a patient having a androgen related disease or disorder, e.g. prostate cancer, are also useful in the methods of the invention. Any number of methods are available for carrying out screening assays to identify new candidate compounds that alter the expression of an androgen receptor variant nucleic acid molecule. In one working example, candidate compounds are added at varying concentrations to the culture medium of cultured cells expressing one of the nucleic acid sequences of the invention. Gene expression is then measured, for example, by microarray analysis, Northern blot analysis (Ausubel et al., supra), or RT-PCR, using any appropriate fragment prepared from the nucleic acid molecule as a hybridization probe. The level of gene expression in the presence of the candidate compound is compared to the level measured in a control culture medium lacking the candidate molecule. A compound that promotes an alteration in the expression of an androgen receptor variant gene, or a functional equivalent thereof, is considered useful in the invention; such a molecule may be used, for example, as a therapeutic to treat a androgen related disease or disorder, e.g. prostate cancer in a human patient.

In another approach, the effect of candidate compounds is measured at the level of polypeptide production to identify those that promote an alteration in an androgen receptor variant polypeptide level. The level of androgen receptor variant polypeptide can be assayed using any standard method. Standard immunological techniques include Western blotting or immunoprecipitation with an antibody specific for an androgen receptor variant polypeptide (e.g., an androgen receptor variant, for example AR-V1, AR-V2, AR-V3, AR-V4, AR-V5, AR-V6, AR-V7, AR-V8 or fragments thereof). For example, immunoassays may be used to detect or monitor the expression of at least one of the polypeptides of the invention in an organism. Polyclonal or monoclonal antibodies (produced as described above) that are capable of binding to such a polypeptide may be used in any standard immunoassay format (e.g., ELISA, Western blot, or RIA assay) to measure the level of the polypeptide. In some embodiments, a compound that promotes a decrease in the expression or biological activity of the polypeptide is considered particularly useful. Again, such a molecule may be used, for example, as a therapeutic to delay, ameliorate, or treat a androgen related disease or disorder, e.g. prostate cancer in a human patient.

In another embodiment, a nucleic acid described herein (e.g., an androgen receptor variant nucleic acid) is expressed as a transcriptional or translational fusion with a detectable reporter, and expressed in an isolated cell (e.g., mammalian or insect cell) under the control of a heterologous promoter, such as an inducible promoter. The cell expressing the fusion protein is then contacted with a candidate compound, and the expression of the detectable reporter in that cell is compared to the expression of the detectable reporter in an untreated control cell. A candidate compound that alters the expression of the detectable reporter is a compound that is useful for the treatment of a androgen related disease or disorder, e.g. prostate cancer. In one embodiment, the compound decreases the expression of the reporter.

Each of the DNA sequences listed herein may also be used in the discovery and development of a therapeutic compound for the treatment of androgen related disease or disorder, e.g. prostate cancer. The encoded protein, upon expression, can be used as a target for the screening of drugs. Additionally, the DNA sequences encoding the amino terminal regions of the encoded protein or Shine-Delgarno or other translation facilitating sequences of the respective mRNA can be used to construct sequences that promote the expression of the coding sequence of interest. Such sequences may be isolated by standard techniques (Ausubel et al., supra).

The invention also includes novel compounds identified by the above-described screening assays. Optionally, such compounds are characterized in one or more appropriate animal models to determine the efficacy of the compound for the treatment of a androgen related disease or disorder, e.g. prostate cancer. Desirably, characterization in an animal model can also be used to determine the toxicity, side effects, or mechanism of action of treatment with such a compound. Furthermore, novel compounds identified in any of the above-described screening assays may be used for the treatment of a androgen related disease or disorder, e.g. prostate cancer in a subject. Such compounds are useful alone or in combination with other conventional therapies known in the art.

Test Compounds and Extracts

In general, compounds capable of inhibiting the growth or proliferation of a androgen related disease or disorder, e.g. prostate cancer by altering the expression or biological activity of an androgen receptor variant polypeptide, variant, or fragment thereof are identified from large libraries of either natural product or synthetic (or semi-synthetic) extracts or chemical libraries according to methods known in the art. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.).

In one embodiment, test compounds of the invention are present in any combinatorial library known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann, R. N. et al., *J. Med. Chem.* 37:2678-85, 1994); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, *Anticancer Drug Des.* 12:145, 1997).

Examples of methods for the synthesis of molecular libraries can be found in the art, for example in: DeWitt et al., *Proc. Natl. Acad. Sci. U.S.A.* 90:6909, 1993; Erb et al., *Proc. Natl. Acad. Sci. USA* 91:11422, 1994; Zuckermann et al., *J. Med. Chem.* 37:2678, 1994; Cho et al., *Science* 261:1303, 1993; Carrell et al., *Angew. Chem. Int. Ed. Engl.* 33:2059, 1994; Carell et al., *Angew. Chem. Int. Ed. Engl.* 33:2061, 1994; and Gallop et al., *J. Med. Chem.* 37:1233, 1994.

Libraries of compounds may be presented in solution (e.g., Houghten, Biotechniques 13:412-421, 1992), or on beads (Lam, *Nature* 354:82-84, 1991), chips (Fodor, *Nature* 364:555-556, 1993), bacteria (Ladner, U.S. Pat. No. 5,223,409), spores (Ladner U.S. Pat. No. 5,223,409), plasmids (Cull et al., *Proc Natl Acad Sci USA* 89:1865-1869, 1992) or on phage (Scott and Smith, *Science* 249:386-390, 1990; Devlin, *Science* 249:404-406, 1990; Cwirla et al. *Proc. Natl. Acad. Sci.* 87:6378-6382, 1990; Felici, *J. Mol. Biol.* 222: 301-310, 1991; Ladner supra.).

Those skilled in the field of drug discovery and development will understand that the precise source of a compound or test extract is not critical to the screening procedure(s) of the invention. Accordingly, virtually any number of chemical extracts or compounds can be screened using the methods described herein. Examples of such extracts or compounds include, but are not limited to, plant-, fungal-, prokaryotic- or animal-based extracts, fermentation broths, and synthetic compounds, as well as modification of existing compounds.

When a crude extract is found to alter the biological activity of an androgen receptor variant polypeptide, variant, or fragment thereof, further fractionation of the positive lead extract is necessary to isolate chemical constituents responsible for the observed effect. Thus, the goal of the extraction, fractionation, and purification process is the careful characterization and identification of a chemical entity within the crude extract having anti-neoplastic activity. Methods of fractionation and purification of such heterogenous extracts are known in the art. If desired, compounds shown to be useful agents for the treatment of a neoplasm are chemically modified according to methods known in the art.

Methods of Assaying Androgen Receptor Variant Biological Activity

Therapeutics useful in the methods of the invention include, but are not limited to, those that alter an androgen receptor variant biological activity associated with, for example cell proliferation, cell survival, cell secretion, gene expression. For example, in the case of prostate cancer, neoplastic cell growth is not subject to the same regulatory mechanisms that govern the growth or proliferation of normal cells and, accordingly, compounds that reduce the growth or proliferation of prostate cancer are useful for the treatment of prostate cancer. Methods of assaying cell growth and proliferation are known in the art. See, for example, Kittler et al. (Nature. 432 (7020):1036-40, 2004) and by Miyamoto et al. (Nature 416(6883):865-9, 2002). Assays for cell proliferation generally involve the measurement of DNA synthesis during cell replication. In one embodiment, DNA synthesis is detected using labeled DNA precursors, such as ([$^3$H]-Thymidine or 5-bromo-2'-deoxyuridine [BrdU], which are added to cells (or animals) and then the incorporation of these precursors into genomic DNA during the S phase of the cell cycle (replication) is detected (Ruefli-Brasse et al., Science 302(5650):1581-4, 2003; Gu et al., Science 302 (5644):445-9, 2003).

Assays for measuring cell viability are known in the art, and are described, for example, by Crouch et al. (J. Immunol. Meth. 160, 81-8); Kangas et al. (Med. Biol. 62, 338-43, 1984); Lundin et al., (Meth. Enzymol. 133, 27-42, 1986); Petty et al. (Comparison of J. Biolum. Chemilum. 10, 29-34, 1995); and Cree et al. (AntiCancer Drugs 6: 398-404, 1995). Cell viability can be assayed using a variety of methods, including MTT (3-(4,5-dimethylthiazolyl)-2,5-diphenyltetrazolium bromide) (Barltrop, Bioorg. & Med. Chem. Lett. 1: 611, 1991; Cory et al., Cancer Comm. 3, 207-12, 1991; Paull J. Heterocyclic Chem. 25, 911, 1988). Assays for cell viability are also available commercially. These assays include CELLTITER-GLO Luminescent Cell Viability Assay (Promega), which uses luciferase technology to detect ATP and quantify the health or number of cells in culture, and the CellTiter-Glo Luminescent Cell Viability Assay, which is a lactate dehyrodgenase (LDH) cytotoxicity assay.

Assays for measuring cell apoptosis are known to the skilled artisan. Apoptotic cells are characterized by characteristic morphological changes, including chromatin condensation, cell shrinkage and membrane blebbing, which can be clearly observed using light microscopy. The biochemical features of apoptosis include DNA fragmentation, protein cleavage at specific locations, increased mitochondrial membrane permeability, and the appearance of phosphatidylserine on the cell membrane surface. Assays for apoptosis are known in the art. Exemplary assays include TUNEL (Terminal deoxynucleotidyl Transferase Biotin-dUTP Nick End Labeling) assays, caspase activity (specifically caspase-3) assays, and assays for fas-ligand and annexin V. Commercially available products for detecting apoptosis include, for example, Apo-ONE® Homogeneous Caspase-3/7 Assay, FragEL TUNEL kit (ONCOGENE RESEARCH PRODUCTS, San Diego, Calif.), the ApoBrdU DNA Fragmentation Assay (BIOVISION, Mountain View, Calif.), and the Quick Apoptotic DNA Ladder Detection Kit (BIOVISION, Mountain View, Calif.).

Microarrays

The methods of the invention may also be used for microarray-based assays that provide for the high-throughput analysis of biomarkers. The androgen receptor variant nucleic acid molecules or polypeptides of the invention are useful as hybridizable array elements in such a microarray. The array elements are organized in an ordered fashion such that each element is present at a specified location on the substrate. Useful substrate materials include membranes, composed of paper, nylon or other materials, filters, chips, glass slides, and other solid supports. The ordered arrangement of the array elements allows hybridization patterns and intensities to be interpreted as expression levels of particular genes or proteins. Methods for making nucleic acid microarrays are known to the skilled artisan and are described, for example, in U.S. Pat. No. 5,837,832, Lockhart, et al. (Nat. Biotech. 14:1675-1680, 1996), and Schena, et al. (Proc. Natl. Acad. Sci. 93:10614-10619, 1996), herein incorporated by reference. Methods for making polypeptide microarrays are described, for example, by Ge (Nucleic Acids Res. 28:e3.i-e3.vii, 2000), MacBeath et al., (Science 289:1760-1763, 2000), Zhu et al. (Nature Genet. 26:283-289), and in U.S. Pat. No. 6,436,665, hereby incorporated by reference.

Nucleic Acid Microarrays

To produce a nucleic acid microarray oligonucleotides may be synthesized or bound to the surface of a substrate using a chemical coupling procedure and an ink jet application apparatus, as described in PCT application WO95/251116 (Baldeschweiler et al.), incorporated herein by reference. Alternatively, a gridded array may be used to arrange and link cDNA fragments or oligonucleotides to the surface of a substrate using a vacuum system, thermal, UV, mechanical or chemical bonding procedure.

A nucleic acid molecule (e.g. RNA or DNA) derived from a biological sample may be used to produce a hybridization probe as described herein. The biological samples are generally derived from a patient, preferably as a bodily fluid (such as blood, cerebrospinal fluid, phlegm, saliva, or urine) or tissue sample (e.g. a tissue sample obtained by biopsy, e.g. prostate tissue). For some applications, cultured cells or other tissue preparations may be used. The mRNA is isolated according to standard methods, and cDNA is produced and used as a template to make complementary RNA suitable for hybridization. Such methods are described herein. The RNA is amplified in the presence of fluorescent nucleotides, and the labeled probes are then incubated with the microarray to allow the probe sequence to hybridize to complementary oligonucleotides (e.g., androgen receptor variant nucleic acid molecules) bound to the microarray.

Incubation conditions are adjusted such that hybridization occurs with precise complementary matches or with various degrees of less complementarity depending on the degree of stringency employed. For example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and most preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In one embodiment, hybridization will occur at 30° C. in 750 mM NaCl, 75 mM trisodium citrate, and 1% SDS. In another embodiment, hybridization will occur at 37° C. in 500 mM NaCl, 50 mM trisodium citrate, 1% SDS, 35% formamide, and 100 µg/ml denatured salmon sperm DNA (ssDNA). In yet another embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

The removal of nonhybridized probes may be accomplished, for example, by washing. The washing steps that follow hybridization can also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., at least about 42° C., or at least about 68° C. In one embodiment, wash steps will occur at 25° C. in 30 mM NaCl, 3 mM trisodium citrate, and 0.1% SDS. In another embodiment, wash steps will occur at 42° C. in 15 mM NaCl, 1.5 mM trisodium citrate, and 0.1% SDS. In yet another embodiment, wash steps will occur at 68° C. in 15 mM NaCl, 1.5 mM trisodium citrate, and 0.1% SDS. Additional variations on these conditions will be readily apparent to those skilled in the art.

A detection system may be used to measure the absence, presence, and amount of hybridization for all of the distinct sequences simultaneously (e.g., Heller et al., Proc. Natl. Acad. Sci. 94:2150-2155, 1997). Preferably, a scanner is used to determine the levels and patterns of fluorescence.

Protein Microarrays

Androgen receptor variant polypeptides (e.g., androgen receptor variant, for example AR-V1, AR-V2, AR-V3, AR-V4, AR-V5, AR-V6, AR-V7, or fragments thereof), such as those described herein, may also be analyzed using protein microarrays. Such arrays are useful in high-throughput low-cost screens to identify peptide or candidate compounds that bind a polypeptide of the invention, or fragment thereof. Typically, protein microarrays feature a protein, or fragment thereof, bound to a solid support. Suitable solid supports include membranes (e.g., membranes composed of nitrocellulose, paper, or other material), polymer-based films (e.g., polystyrene), beads, or glass slides. For some applications, androgen receptor variant polypeptides (e.g., androgen receptor variant, for example AR-V1, AR-V2, AR-V3, AR V4, AR-V5, AR-V6, AR-V7, AR-V8 or fragments thereof) are spotted on a substrate using any convenient method known to the skilled artisan (e.g., by hand or by inkjet printer). Preferably, such methods retain the biological activity or function of the protein bound to the substrate (e.g., androgen receptor variant antibody binding).

The protein microarray is hybridized with a detectable probe. Such probes can be polypeptide (e.g., an androgen receptor variant antibody), nucleic acid, or small molecules. For some applications, polypeptide and nucleic acid probes are derived from a biological sample taken from a patient, such as a bodily fluid (such as blood, urine, saliva, or phlegm); a homogenized tissue sample (e.g. a tissue sample obtained by biopsy, e.g. from the prostate); or cultured cells (e.g., lymphocytes). Probes can also include antibodies, candidate peptides, nucleic acids, or small molecule compounds derived from a peptide, nucleic acid, or chemical library. Hybridization conditions (e.g., temperature, pH, protein concentration, and ionic strength) are optimized to promote specific interactions. Such conditions are known to the skilled artisan and are described, for example, in Harlow, E. and Lane, D., Using Antibodies: A Laboratory Manual. 1998, New York: Cold Spring Harbor Laboratories. After removal of non-specific probes, specifically bound probes are detected, for example, by fluorescence, enzyme activity (e.g., an enzyme-linked calorimetric assay), direct immunoassay, radiometric assay, or any other suitable detectable method known to the skilled artisan.

Detection of an increase in the amount of an androgen receptor variant polypeptide (e.g., androgen receptor variant, for example AR-V1, AR-V2, AR-V3, AR-V4, AR-V5, AR-V6, AR-V7, AR-V8 or fragments thereof) or an androgen receptor variant polynucleotide present in a patient sample is useful as a diagnostic for the presence of a androgen related disease or disorder, e.g. prostate cancer. Optionally, androgen receptor variant detection may be combined with the detection of other biomarkers, where the presence or level of the biomarker is correlated with the presence of a androgen related disease or disorder, e.g. prostate cancer.

Pharmaceutical Compositions

The present invention contemplates pharmaceutical preparations comprising an androgen receptor variant protein, a polynucleotide that encodes an androgen receptor variant protein, or an androgen receptor variant inhibitory nucleic acid molecule (e.g., a polynucleotide that hybridizes to and interferes with the expression of an androgen receptor variant polynucleotide), together with a pharmaceutically acceptable carrier. Polynucleotides of the invention may be administered as part of a pharmaceutical composition. The compositions should be sterile and contain a therapeutically effective amount of the polypeptides or nucleic acid molecules in a unit of weight or volume suitable for administration to a subject.

These compositions ordinarily will be stored in unit or multi-dose containers, for example, sealed ampoules or vials, as an aqueous solution or as a lyophilized formulation for reconstitution. As an example of a lyophilized formulation, 10 mL vials are filled with 5 mL of sterile-filtered 1% (w/v) aqueous androgen receptor variant polynucleotide solution, such as an aqueous solution of androgen receptor variant polynucleotide or polypeptide, and the resulting mixture can then be lyophilized. The infusion solution can be prepared by reconstituting the lyophilized material using sterile Water-for-Injection (WFI).

The androgen receptor variant polynucleotide, or polypeptide, or analogs may be combined, optionally, with a pharmaceutically acceptable excipient. The term "pharmaceutically-acceptable excipient" as used herein means one or more compatible solid or liquid filler, diluents or encapsulating substances that are suitable for administration into a human. The term "carrier" denotes an organic or inorganic ingredient, natural or synthetic, with which the active ingredient is combined to facilitate administration. The components of the pharmaceutical compositions also are capable of being co-mingled with the molecules of the present invention, and with each other, in a manner such that there is no interaction that would substantially impair the desired pharmaceutical efficacy.

The compositions can be administered in effective amounts. The effective amount will depend upon the mode of administration, the particular condition being treated and the desired outcome. It may also depend upon the stage of the condition, the age and physical condition of the subject, the nature of concurrent therapy, if any, and like factors well known to the medical practitioner. For therapeutic applications, it is that amount sufficient to achieve a medically desirable result.

With respect to a subject having an androgen related disease or disorder, an effective amount is sufficient to stabilize, slow, or reduce the progression of the disease or disorder, for example the progression of prostate cancer. Generally, doses of active polynucleotide compositions of the present invention would be from about 0.01 mg/kg per day to about 1000 mg/kg per day. It is expected that doses ranging from about 50 to about 2000 mg/kg will be suitable. Lower doses will result from certain forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of the androgen receptor variant polynucleotide or polypeptide compositions of the present invention.

A variety of administration routes are available. The methods of the invention, generally speaking, may be practiced using any mode of administration that is medically acceptable, meaning any mode that produces effective levels of the active compounds without causing clinically unacceptable adverse effects. Other modes of administration include oral, rectal, topical, intraocular, buccal, intravaginal, intracisternal, intracerebroventricular, intratracheal, nasal, transdermal, within/on implants, e.g., fibers such as collagen, osmotic pumps, or grafts comprising appropriately transformed cells, etc., or parenteral routes. Other useful approaches are described in Otto, D. et al., J. Neurosci. Res. 22: 83-91 and in Otto, D. and Unsicker, K. J. Neurosci. 10: 1912-1921.

Combination Therapies

Compositions and methods of the invention may be used in combination with any conventional therapy known in the art. In one embodiment, an androgen receptor variant polynucleotide or polypeptide composition of the invention having anti-neoplastic activity may be used in combination with any anti-neoplastic therapy known in the art. Exemplary anti-neoplastic therapies include, for example, chemotherapy, cryotherapy, hormone therapy, radiotherapy, and surgery. A androgen receptor variant polynucleotide composition of the invention may, if desired, include one or more chemotherapeutics typically used in the treatment of a neoplasm, such as abiraterone acetate, altretamine, anhydrovinblastine, auristatin, bexarotene, bicalutamide, BMS184476, 2,3,4,5,6-pentafluoro-N-(3-fluoro-4-methoxyphenyl)benzene sulfonamide, bleomycin, N,N-dimethyl-L-valyl-L-valyl-N-methyl-L-valyl-L-proly-1-Lproline-t-butylamide, cachectin, cemadotin, chlorambucil, cyclophosphamide, 3',4'-didehydro-4'-deoxy-8'-norvincaleukoblastine, docetaxol, doxetaxel, cyclophosphamide, carboplatin, carmustine (BCNU), cisplatin, cryptophycin, cyclophosphamide, cytarabine, dacarbazine (DTIC), dactinomycin, daunorubicin, dolastatin, doxorubicin (adriamycin), etoposide, 5-fluorouracil, finasteride, flutamide, hydroxyurea and hydroxyureataxanes, ifosfamide, liarozole, lonidamine, lomustine (CCNU), mechlorethamine (nitrogen mustard), melphalan, mivobulin isethionate, rhizoxin, sertenef, streptozocin, mitomycin, methotrexate, 5-fluorouracil, nilutamide, onapristone, paclitaxel, prednimustine, procarbazine, RPR109881, stramustine phosphate, tamoxifen, tasonermin, taxol, tretinoin, vinblastine, vincristine, vindesine sulfate, and vinflunine Other examples of chemotherapeutic agents can be found in Cancer Principles and Practice of Oncology by V. T. Devita and S. Hellman (editors), 6th edition (Feb. 15, 2001), Lippincott Williams & Wilkins Publishers.

The following examples are offered by way of illustration, not by way of limitation. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined not with reference to the above description, but instead should be determined with reference to the appended claims along with their full scope of equivalents.

EXAMPLES

Studies described herein focus in part on AR-V7, one of the variants with the most abundant expression and also the highest activity. The studies reported here show that AR-V7 was elevated by approximately 20-fold in castration-resistant prostate cancer cells derived from patients who died from metastatic prostate cancer following hormone therapy failure. Interestingly, generally lower but varied AR-V7 expression was also detected in prostate cancers that had not been influenced by hormone ablation, and higher AR-V7 expression predicted PSA recurrence following local therapy in these patients. These results suggest that castration-resistant prostate cancer cells bearing the signatory marker of a constitutively active AR are present prior to hormone therapies, and these cells may propagate under the selection pressure induced by lack of sufficient androgens, leading to progressive castration-resistant prostate cancer.

The results shown herein are particularly useful in methods of determining if a subject with prostate cancer will respond to androgen therapy, where the level of expression or biological activity of an androgen receptor variant polypeptide or the level of expression of an androgen receptor variant nucleic acid is determined, and an alteration in the level of expression or biological activity relative to the expression or biological activity in a reference indicates that the subject will respond to androgen therapy. In certain cases, the method can be used to determine the prognosis of a prostate cancer subject in clinical remission.

The decoding and characterization of novel AR variants make it possible to detect and manipulate prostate cancer cells with constitutively active AR signaling under complete hormone ablation. Future studies will address the relative importance and clinical relevance of ligand-dependent versus ligand-independent routes toward hormone therapy failure and focus on the development of methods and approaches to detect and modify the ligand-independent AR-signaling pathway.

Example 1

Identification of Cryptic AR Exons

BLAST searches were performed of the ~170-kb AR intron sequences against the National Center for Biotechnology Information human expressed sequence tag database. High quality hits (99% identity) were found in intron 1 (6 hits), intron 2 (3 hits), and intron 3 (3 hits) but not in the remaining four introns (See Table 1, below). Table 1 shows a summary of transcribed genomic fragments within human AR gene introns.

TABLE 1

| Intron | Accession ID | Size (bp) | Identity | Start* | End** |
|---|---|---|---|---|---|
| 1 | AA886614 | 231 | 99.6% | 66722674 | 66722904 |
| 1 | AA577938 | 293 | 99.0% | 66723711 | 66724004 |
| 1 | AW5973726 | 294 | 100.0% | 66723711 | 66724004 |
| 1 | R89771 | 382 | 100.0% | 66725430 | 66725814 |
| 1 | AI827337 | 490 | 100.0% | 66750976 | 66751465 |
| 1 | AW028775 | 437 | 99.8% | 66772546 | 66772983 |
| 2 | BF327858 | 202 | 99.6% | 66791497 | 66791698 |
| 2 | BE007634 | 450 | 99.6% | 66791497 | 66791950 |
| 2 | BE006793 | 355 | 100.0% | 66819126 | 66819482 |
| 3 | CV379421 | 270 | 100.0% | 66826610 | 66826880 |
| 3 | CN283227 | 674 | 99.3% | 66829412 | 66830085 |
| 3 | BF846156 | 538 | 99.7% | 66831722 | 66832259 |
| 4 | None | | | | |
| 5 | None | | | | |
| 6 | None | | | | |
| 7 | None | | | | |

*Starting position coordinates on human chromosome X according to Reference Human Genome Assembly (March 2006 release, HG18)
**Ending position coordinates on human chromosome X according to Reference Human Genome Assembly (March 2006 release, HG18)

These transcribed "intronic" genomic fragments, considered as putative cryptic exons, were not spliced as currently annotated, and therefore, their exon-intron junctions were undefined. Because a functional AR would most likely retain the AR DBD encoded by exons 2 and 3, three putative cryptic exons in intron 3 were the focus in these studies in order to determine whether and how they were joined (i.e., spliced) with the upstream exon 3, and their potential to disrupt the AR open reading frame (ORF). Primers (P1, P2, and P3; Table 2, shown below) were designed to amplify and sequence mRNA transcripts containing exons encoding AR DBD and the putative cryptic exons. Table 2 shows the primer sets used in the study and the corresponding amplicon data.

TABLE 2

| Primer Sets | Forward Primer | Reverse Primer | Amplified Transcript Size (bp) |
|---|---|---|---|
| P1 (FIG. 1A) | TGTCACTATGGAGCTCTCACATGTGG | CACCTCTCAAATATGCTAGACGAATCTGT | AR-V1: 842<br>AR-V2: 959<br>AR-V3: 1126<br>AR-V4: 1243 |
| P2 (FIG. 1A) | TGTCACTATGGAGCTCTCACATGTGG | GTACTCATTCAAGTATCAGATATGCGGTATCAT | AR-V5: 888<br>AR-V6: 968 |
| P3 (FIG. 1A) | TGTCACTATGGAGCTCTCACATGTGG | CTGTGGATCAGCTACTACCTTCAGCTC | AR V7: 834 |
| P4 (FIG. 1C) | GTTGCTCCCGCAAGTTTCCTTCTC | CTGTTGTGGATGAGCAGCTGAGAGTCT | AR-V1 full-length ORF: 2134 |
| P5 (FIG. 1C) | GTTGCTCCCGCAAGTTTCCTTCTC | TTTGAATGAGGCAAGTCAGCCTTTCT | AR-V7 full-length ORF: 2113 |
| P6 (FIG. 2A) | CCATCTTGTCGTCTTCGGAAATGTTATGAAGC | CTGTTGTGGATGAGCAGCTGAGAGTCT | AR-V1: 145 |
| P7 (FIG. 2A) | CCATCTTGTCGTCTTCGGAAATGTTATGAAGC | TTTGAATGAGGCAAGTCAGCCTTTCT | AR-V7: 125 |
| P8 (FIG. 2A) | CCATCTTGTCGTCTTCGGAAATGTTATGAAGC | AGCTTCTGGGTTGTCTCCTCAGTGG | AR prototype: 143 |
| SF3A3 (FIG. 2A) | TACGAAAGGAGGAGCTCAATGCAA | AGATCTCATTTGGGTGCTTCCGGT | SF3A3: 107 |

All primers, forward and reverse (corresponding to the complementary strand), are shown in the 5' to 3' direction.

Primer set 1 (P1) corresponds to
(SEQ ID NO: 15)
TGTCACTATGGAGCTCTCACATGTGG
and
(SEQ ID NO: 16)
CACCTCTCAAATATGCTAGACGAATCTGT.

Primer set 2 (P2) corresponds to
(SEQ ID NO: 17)
TGTCACTATGGAGCTCTCACATGTGG
and
(SEQ ID NO: 18)
GTACTCATTCAAGTATCAGATATGCGGTATCAT.

Primer set 3 (P3) corresponds to
(SEQ ID NO: 19)
TGTCACTATGGAGCTCTCACATGTGG
and
(SEQ ID NO: 20)
CTGTGGATCAGCTACTACCTTCAGCTC.

Primer set 4 (P4) corresponds to
(SEQ ID NO: 21)
GTTGCTCCCGCAAGTTTCCTTCTC
and
(SEQ ID NO: 22)
CTGTTGTGGATGAGCAGCTGAGAGTCT.

Primer set 5 (P5) corresponds to
(SEQ ID NO: 23)
GTTGCTCCCGCAAGTTTCCTTCTC
and
(SEQ ID NO: 24)
TTTGAATGAGGCAAGTCAGCCTTTCT.

Primer set 6 (P6) corresponds to
(SEQ ID NO: 25)
CCATCTTGTCGTCTTCGGAAATGTTATGAAGC
and
(SEQ ID NO: 26)
CTGTTGTGGATGAGCAGCTGAGAGTCT.

Primer set 7 (P7) corresponds to
(SEQ ID NO: 27)
CCATCTTGTCGTCTTCGGAAATGTTATGAAGC
and
(SEQ ID NO: 28)
TTTGAATGAGGCAAGTCAGCCTTTCT.

Primer set 8 (P8) corresponds to
(SEQ ID NO: 29)
CCATCTTGTCGTCTTCGGAAATGTTATGAAGC
and
(SEQ ID NO: 30)
AGCTTCTGGGTTGTCTCCTCAGTGG.

Primer set SF3A3 corresponds to
(SEQ ID NO: 31)
TACGAAAGGAGGAGCTCAATGCAA
and
(SEQ ID NO: 32)
AGATCTCATTTGGGTGCTTCCGGT.

Primer set 9 (P9) corresponds to
(SEQ ID NO: 37)
Tgtcactatggagctctcacatgtgg-
and
(SEQ ID NO: 38)
Cattgtggccaacatgacacttca.

The detection and subsequent sequencing of the amplicons derived from the CWR22Rv1 cells confirmed that all three cryptic exons (CE1, CE2, and CE3) were joined with exon 3 (FIG. 1A). These sequencing results were used to construct seven AR transcript variants, named AR-V 1 to AR-V7, each containing one of the three original cryptic exons (FIG. 1A). Analysis of transcripts containing cryptic exon 1 (CE1) also uncovered an additional cryptic exon in intron 2, named CE4 (FIG. 1A), which was spliced in both AR-V3 and AR-V4 (FIG. 1A). The genomic position of CE4 is identical to the novel exon recently published by Dehm and colleagues (9), but the specific sequence reported differed from the consensus sequences that were detected in the two CE4-containing variants (AR-V3 and AR-V4; FIG. 1A). CWR22Rv1 is a human PCa cell line derived from a serially transplanted PCa xenograft that relapsed after castration-induced regression and is known to have a unique duplicated exon 3 (13). The duplicated exon 3 was reflected in AR-V2 and AR-V4 transcripts (FIG. 1A). AR-V5 and AR-V6 contained cryptic exon 2 (CE2) and differed by a contiguous 80-bp sequence at the 5' junction of CE2 due to alternative 5' splicing sites spaced 80 by apart in CE2 (data not shown). Of importance, all seven AR variants harbor premature termination codons (PTC) downstream of AR DBD, generating AR LBD-truncated AR proteins if translated (FIG. 1A).

In preferred examples P9 is used to amplify AR-V8.

Example 2

Cloning of the Full-Length ORFs of AR-V1 and AR-V7

Semiquantitative RT-PCR analysis in a small set of clinical specimens detected the variant transcripts prevalently in HRPC samples (FIG. 1B). The full-length ORFs of AR-V1 and AR-V7 were then amplified from two clinical HRPC specimens and CWR22Rv1 cells (FIG. 1C). Sequence analysis of the full-length amplicons confirmed the intact ORF of AR NTD and DBD and, thus, the transcript structure for AR-V 1 and AR-V7. Due to their relative lower abundance (FIG. 1B), AR-V5 and AR-V6 were not further pursued for full-length ORF cloning. AR-V2 and AR-V4 were specific to CWR22Rv1 (data not shown) due to the presence of exon 3 duplication and therefore also not pursued further. AR-V3 harbors a stop codon in CE4 and would lack the second zinc finger of AR DBD encoded by exon 3. Such variants may not be functional according to a previous study (14), although the study by Dehm and colleagues (9) suggested otherwise. In addition, the full-length ORF for AR-V3 thus far has not been detected in sequenced clones (data not shown). For these reasons, only AR-V 1 and AR-V7 were pursued further.

Example 3

Expression Analysis of AR-V1 and AR-V7

Figure 2A:
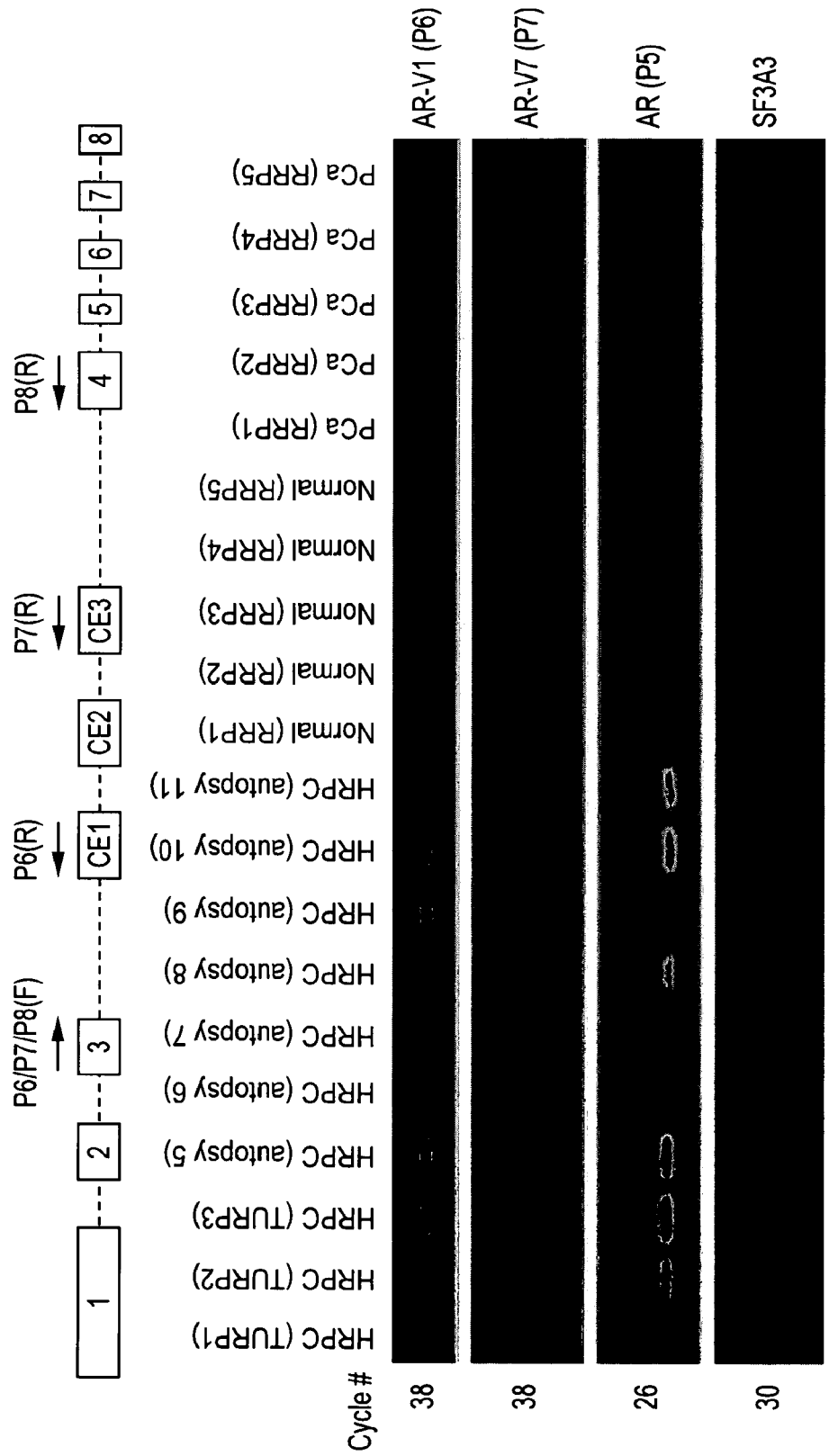
FIG. 2A-C shows quantification of AR variant transcripts in clinical specimens. A, representative gel images of amplified AR variant transcripts detected using primer sets designed for real-time RT-PCR assays. An identical forward primer, P6/P7/P8(F), in exon 3 was paired with different reverse primers, P6(R), P7(R), and P8(R) (Table 2), to amplify the AR-V1, AR-V7, and prototype AR transcripts, respectively. SF3A3 was used as a reference gene transcript (Materials and Methods). Normal (RRP), normal prostate tissues from RRP specimens; PCa (RRP), hormone-naive PCa from RRP specimens; HRPC (TURP), HRPC samples from TURP; HRPC (autopsy), metastatic HRPC samples from autopsies (Table 3). B, quantitative results of AR-V7 in 124 clinical prostate specimens by real-time PCR. Normalized expression values (in log 2 scale) for AR-V7 derived from comparative threshold analysis were shown in four groups of clinical specimens. Normal (n=17), normal prostate tissues from RRP specimens; Hormone naive PCa (n=82), PCa samples from RRP specimens; HRPC (TURP) (n=4), HRPC samples from TURP; HRPC (autopsy) (n=21), metastatic HRPC samples from autopsies (Table 3). C, Kaplan-Meier plot comparing progression-free survival in patients with less than median AR-V7 expression (n=38) with those with greater than median AR-V7 expression (n=28). The survival curves were compared using the log-rank test. Follow-up years were marked on the X axis. Censored subjects were marked with vertical ticks in blue. Note that the PSA recurrence status was annotated in years, not months.
Figure 2C:
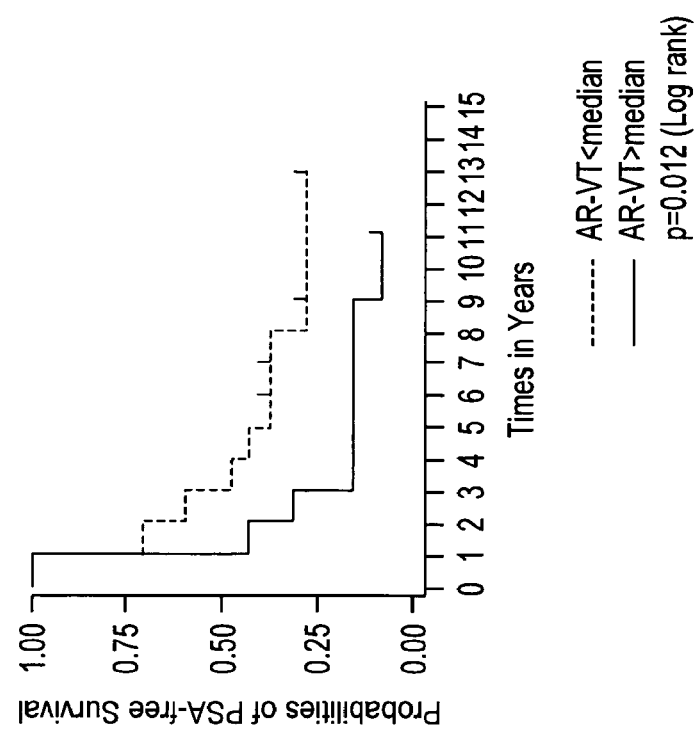
Figure 2B:
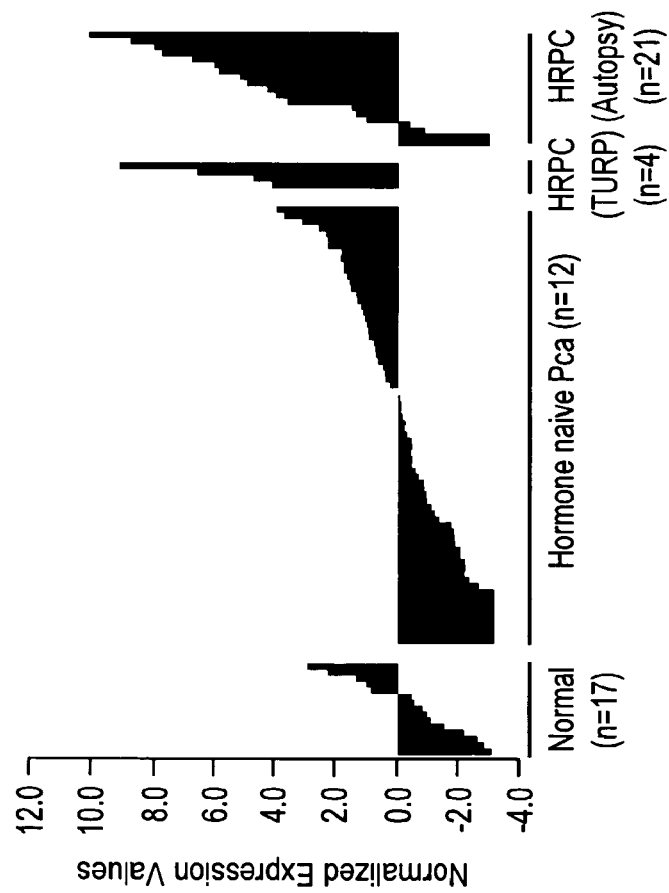
Figure 6A:
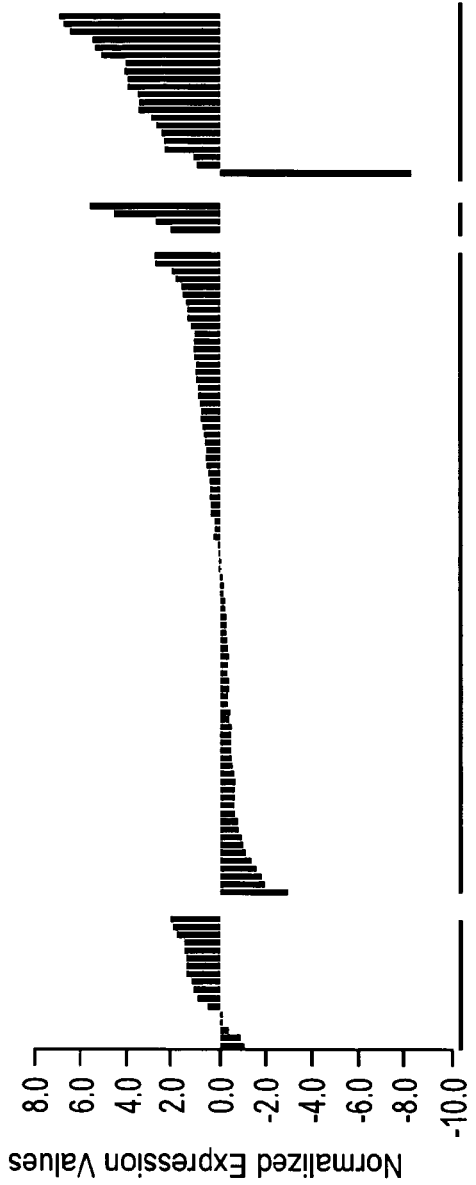
FIG. 6A-B shows Quantitative real-time RT-PCR results of prototype AR (A) and AR-V 1 (B) in 124 clinical prostate specimens. Normalized expression values (in log 2 scale) from comparative threshold analysis were centered with the median of measurable values in 82 RRP cases set at zero. Normal (n=17): normal prostate tissues from radical retropubic prostatectomy (RRP) specimens; Hormone Naïve PCa (n=82): PCa samples from RRP specimens; HRPC (TURP) (n=4): HRPC samples from transurethral resection of prostate (TURP); HRPC (autopsy) (n=21): metastatic HRPC samples from autopsies (see Table 3).
Figure 6B:
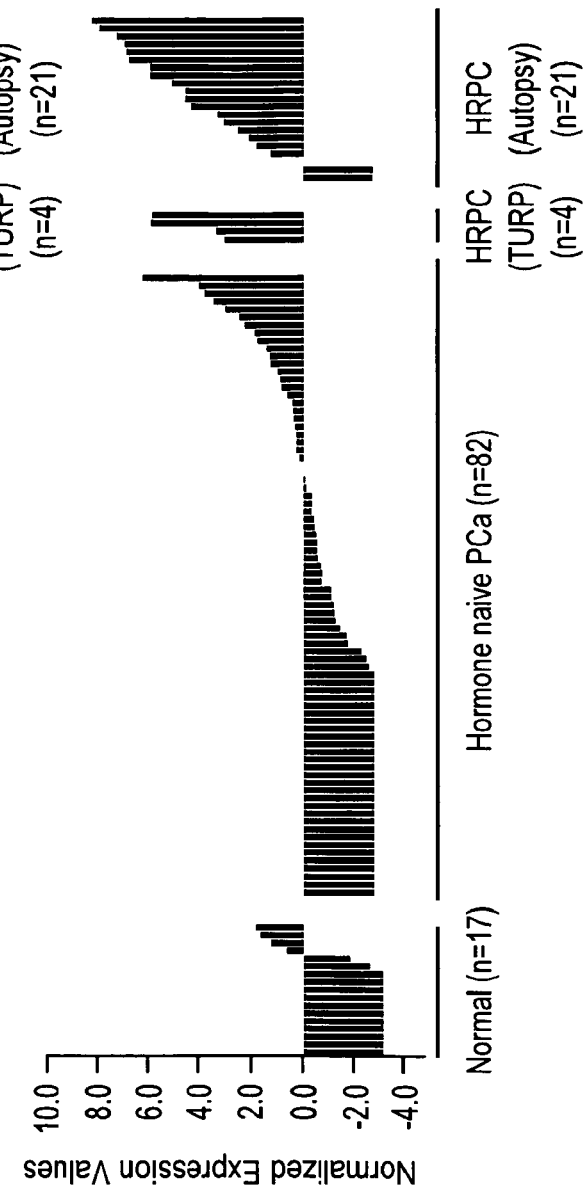
Figure 7A:
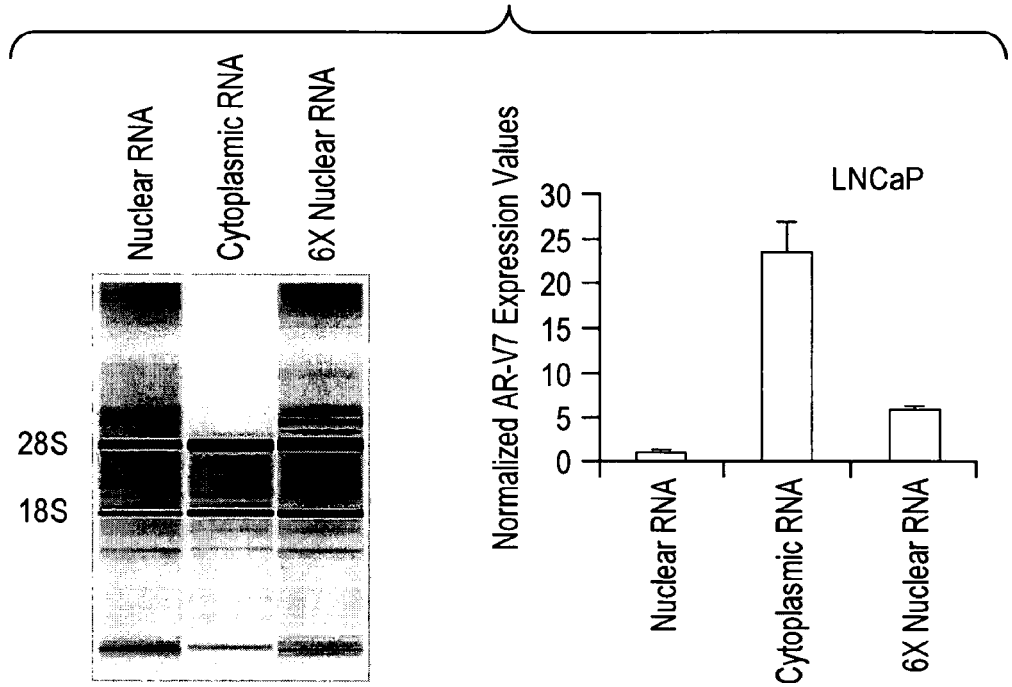
FIG. 7A-B shows detection of AR-V7 transcripts using cytoplasmic or nuclear RNA extracted from LNCaP cells (A) and CWR22Rv1 cells (B). The Agilent Bioanalyzer electropherograms were shown to the left and the expression fold differences relative to the average value of nuclear RNA (from threshold cycle analysis) were shown to the right. The three samples for each cell line correspond to nuclear and cytoplasmic RNA isolated from equal number of cells, and nuclear RNA from 6 fold excess of cells (6×nuclear RNA) to equalize the input nuclear RNA quantity with cytoplasmic RNA, as RNA yield/cell is ~6 fold higher in the cytoplasm than in then nucleus. Note that nuclear RNA is enriched for precursor rRNA (band above 28S rRNA). Also note that mature rRNA, but not mRNA, should be expected to be present in the nucleolus.
Figure 7B:
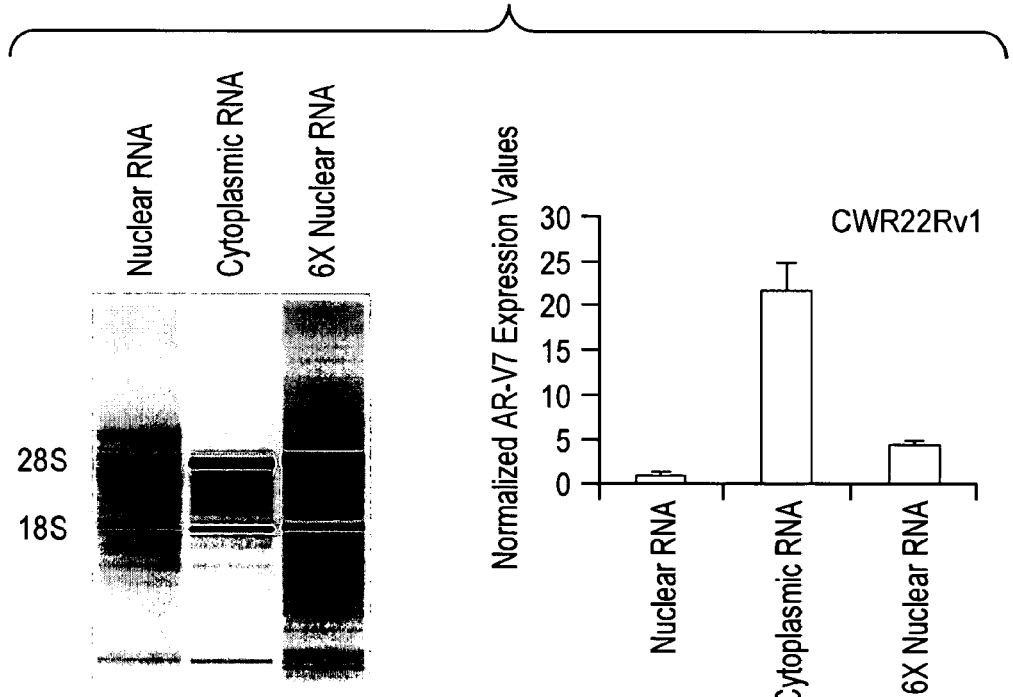
Figure 8A:
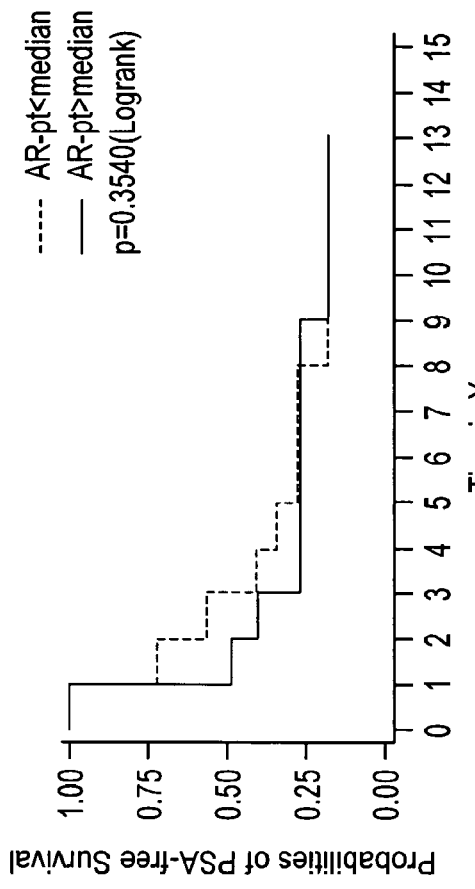
FIG. 8A-B shows Kaplan-Meier plot comparing progression free survival in 66 patients with lower than median and higher than median expression of prototype AR (AR-pt) expression (A) or ratio of AR-V7/AR-pt (B). The median value was identified based on all RRP cases (n=82) with measurable data points to be consistent with all similar analyses including data presented in FIG. 6B. The survival curves were compared using the Log-rank test. And p values of the tests were provided. Follow-up years were marked on the X axis. Censored subjects were marked with vertical ticks in blue. Note that the PSA recurrence status was annotated in years, not months.
Figure 8B:
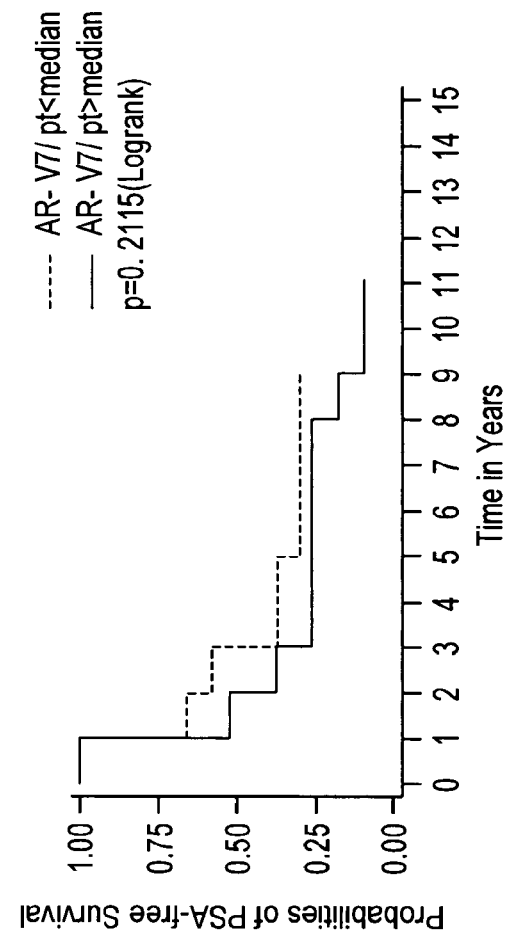

HRPC specimens expressed consistently higher levels of AR-V1, AR-V7, and the prototype AR detected using optimized primer sets specific to each target transcript (FIG. 2A). Expression of the prototype AR can be readily detected at 28 PCR cycles, whereas detection of the AR AR variants, at mRNA levels, relative to the prototype AR (FIG. 2A). Quantitative real-time RT-PCR of AR-V1, AR-V7, and prototype AR was performed on an expanded series of human prostate tissues (n=124) and cell lines (n=9; see FIG. 5). Expression levels of AR-V1, AR-V7, and prototype AR were significantly higher in HRPC (n=25) than in hormone-naive PCa (n=82; P<0.0001, Mann-Whitney test). Adjusted for amplification efficiency, the average expression values for prototype AR (see FIG. 6A), AR-V 1 (see FIG. 6B), and AR-V7 (FIG. 2B) were elevated by 11-, 22-, and 20-fold, respectively, when compared with hormone-naive PCa. It is unlikely that nuclear splicing intermediates of the prototype AR gene contributed to the detected AR variant signals because nRNA contributed <5% of the signal when compared with cytoplasmic RNA on a per cell basis (see FIG. 7). A subset of hormone-naive PCa expressed AR variants at levels comparable with those in HRPC specimens (FIG. 2B). This elevated AR-V7 expression was associated with worse clinical outcome (log-rank P=0.012), as defined by prostate-specific antigen (PSA) recurrence following surgical treatment (FIG. 2C), in 66 RRP cases for which long-term clinical follow-up data were available. In this same sample set (n=66), higher prototype AR mRNA levels did not predict PSA failure (see FIG. 8A). Similarly, higher ratio of V7/AR did not predict PSA failure (see FIG. 8B), although there seemed to be a trend. AR-V 1 expression was not associated with this clinical outcome (log-rank P=0.498; data not shown). It is unknown why AR-V 1 and AR-V7, although both overexpressed in HRPC specimens, differed in their association with PSA recurrence. It is worth noting that our preliminary analysis predicted that AR-V 1 variant-specific sequences (FIG. 1A) lack the basic amino acids characteristic of the bipartite nuclear localizing sequence (15) and therefore may not be a fully functional nuclear receptor (data not shown).

Table 3, shown below, shows androgen therapies and the metastatic sites of the assayed HPRC cases.

TABLE 3

| A# | Gleason Score at Dx | Androgen-targeted therapies | Assayed Mets |
|---|---|---|---|
| 2 | 7 | leuprolide, Flutamide, | Liver |
| 7 | 9 | leuprolide, Flutamide, | Subdural |
| 8 | 6 | goserelin, Flutamide | Liver |
| 9 | 7 | leuprolide, flutamide | Periportal LN |
| 10 | 8 | goserelin, flutamide | Perigastric LN |
| 16 | 7 | leuprolide, flutamide | Adrenal |
| 17 | 7 | leuprolide, flutamide | Hilar LN |
| 19** | 8 | leuprolide, flutamide | Pelvic LN |
| 19** | 8 | leuprolide, flutamide | Bone (Humerus) |
| 21 | 7 | leuprolide, flutamide | Iliac crest soft tissue |
| 23 | 7 | goserelin | Liver |
| 24 | 6 | leuprolide, flutamide | Pericardial Met |
| 26 | 8 | goserelin, flutamide | Bone (T12) |
| 27 | 7 | leuprolide, flutamide | Axillary LN |
| 28 | 7 | leuprolide, flutamide, orchiectomy | Anterior Mediastinal LN |
| 29 | 6 | goserelin, flutamide | Inguinal LN |
| 30 | 7 | leuprolide, flutamide | Liver |
| 31 | 6 | goserelin, flutamide | Subdural |
| 32 | 8 | orchiectomy | Bone (Rib) |
| 33 | 7 | orchiectomy | Subdural |
| 34 | 5 | leuprolide, flutamide | Liver |

*A total of 21 sectioned, pathologically and anatomically validated metastatic hormone refractory prostate cancer lesions derived from 20 autopsy cases were prepared and assayed.
**Two distant mets from case number 19 were assayed.

Example 4

AR-V7 is Translated and Constitutively Active

Figure 3A:
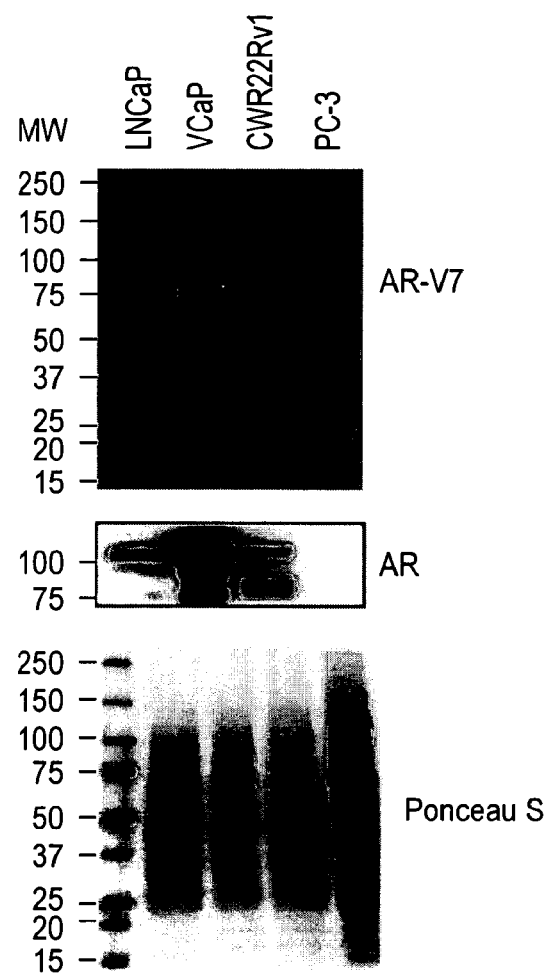
FIG. 3A-D shows AR-V7 protein detection and analysis using a variant-specific antibody. A, detection of AR-V7 protein product in cell lines expressing high levels of AR-V7 transcript (see FIG. 5). Following immunoblot analysis for AR-V7 (top), the same membrane was stripped and subjected to immunoblot analysis with anti-AR(N20) antibody (middle) to detect the prototype AR. Bottom, loading of total protein was monitored by Ponceau S staining of the polyvinylidene difluoride (PVDF) membrane. B, detection of AR-V7 protein following enrichment of all NTD-containing AR proteins by IP using the anti-AR(441) antibody. Note that following enrichment, AR-V7 was detected in cell lines expressing highest levels of AR-V7 mRNA, VCaP and CWR22Rv1 cells, but not in LNCaP cells, which expressed low levels of AR-V7 (see FIG. 5). Control, mouse IgG; anti-AR, anti-AR(441) monoclonal antibody. C, detection of AR-V7 protein in HRPC. Western blot analysis was performed to detect AR-V7 in whole tissue lysates and enriched AR protein extracts derived from four hormone-naive human PCa tissue (RRP5, RRP6, RRP7, and RRP8) and two hormone-refractory human PCa tissues (TURP1 and TURP2). Middle, protein loading was monitored by Ponceau S staining of the PVDF membrane; bottom, IP with the anti-AR(441) antibody was performed to enrich the AR proteins and immunoblotted (IB) with anti-AR(N20) to detect the prototype AR, and AR-V7 by the anti-AR-V7 antibody. D, biochemical analysis of cellular localization of AR-V7 protein. VCaP and CWR22Rv1 cells were grown in phenol red-free RPMI 1 640 containing CSS with or without 1 0 nmol/L R1 881. The cytosolic fraction (C) and nuclear fraction (N) of lysates with equivalent number of cells were isolated and subjected to immunoblot analysis of AR-V7, prototype AR by anti-AR(N20) antibody, and h-actin.
Figure 3B:
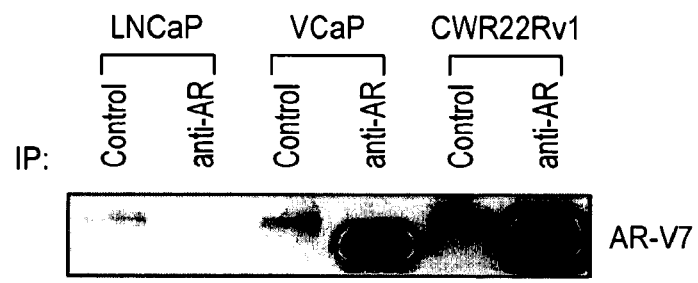
Figure 3C:
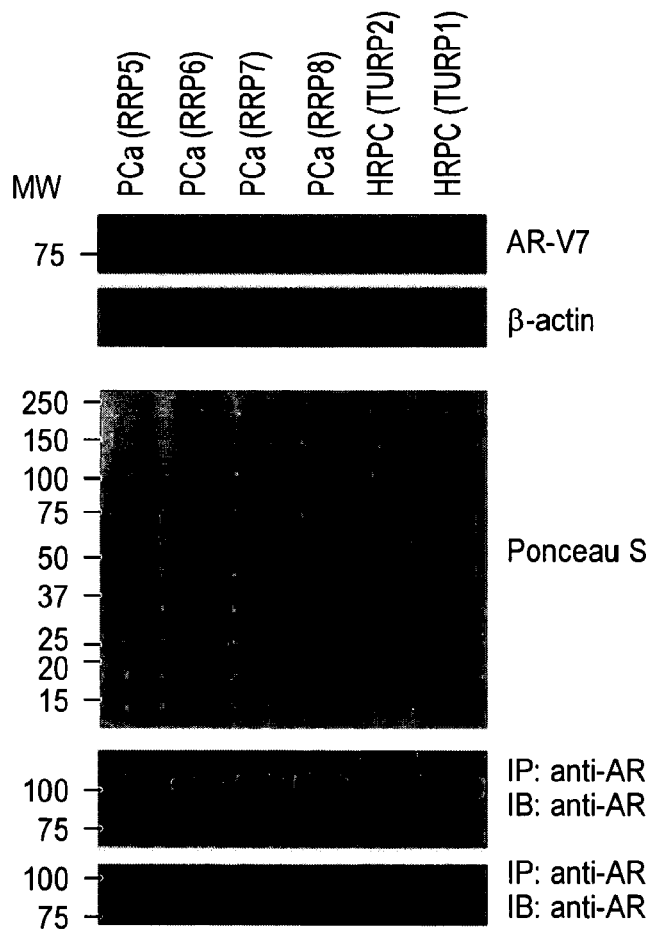
Figure 3D:
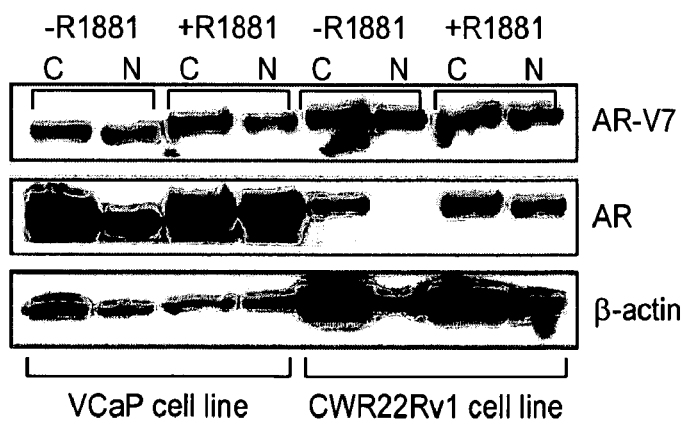
Figure 4A:
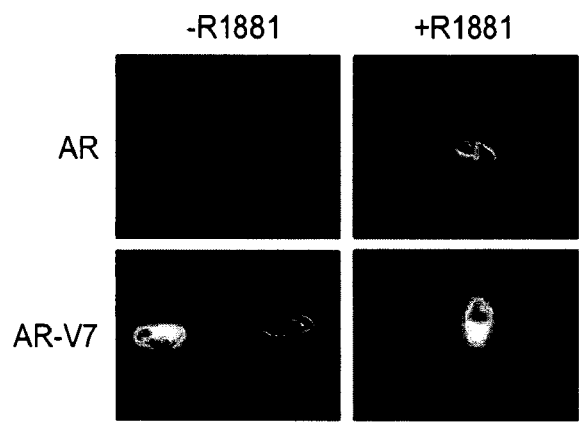
FIG. 4A-C shows constitutive function of AR-V7. A, constitutive nuclear localization of transfected AR-V7 in the absence of androgen. PC-3 cells were transfected with pEGFP-AR and pEGFP-AR-V7 to express the prototype AR or AR-V7 and examined for the localization of GFP-tagged AR proteins in the presence or absence of 5 nmol/L R1 881. B, AR-V7 constitutively activates an AR luciferase reporter. PC-3 cells were transfected with vector control (EGFP), a LBD-truncated AR mutant (EGFP-Q640X), AR-V7 (EGFP-AR-V7), and prototype AR (EGFP-AR) and subjected to luciferase assays and Western blot analysis following culturing in the presence or absence of R1 881. C, androgen-independent induction of AR-responsive genes by AR-V7 in LNCaP cells. LNCaP cells were transfected with pcDNA-AR-V7 to express the untagged AR-V7 protein or the control pcDNA vector and cultured with or without 10 nmol/L R1 881 before being harvested for Western blot analysis or RNA extraction for expression microarray analysis. The genes shown were the top 20 ranked genes by fold induction following R1 881 treatment in pcDNA empty vector-transfected LNCaP cells. Expression ratios of the test sample versus the common reference (pcDNA empty vector-transfected LNCaP without R1 881) were represented by red (>1) and green colors (<1).
Figure 4B:
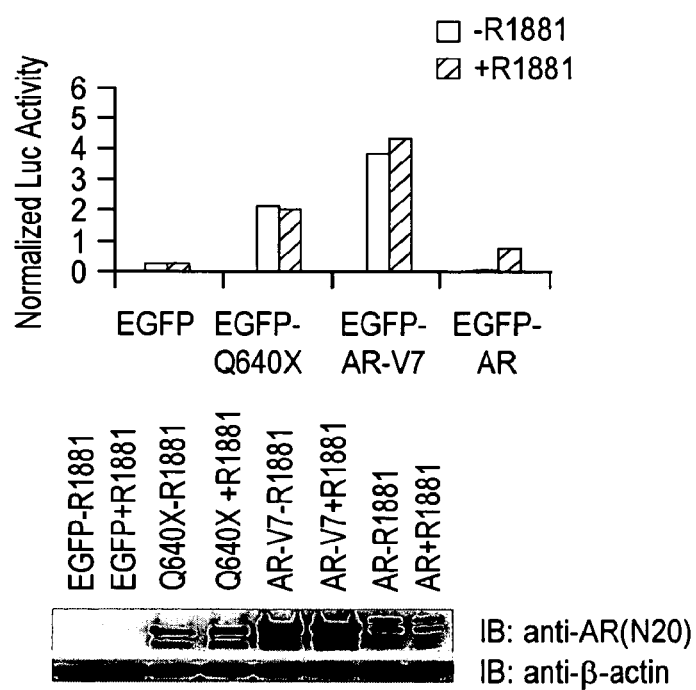
Figure 4C:
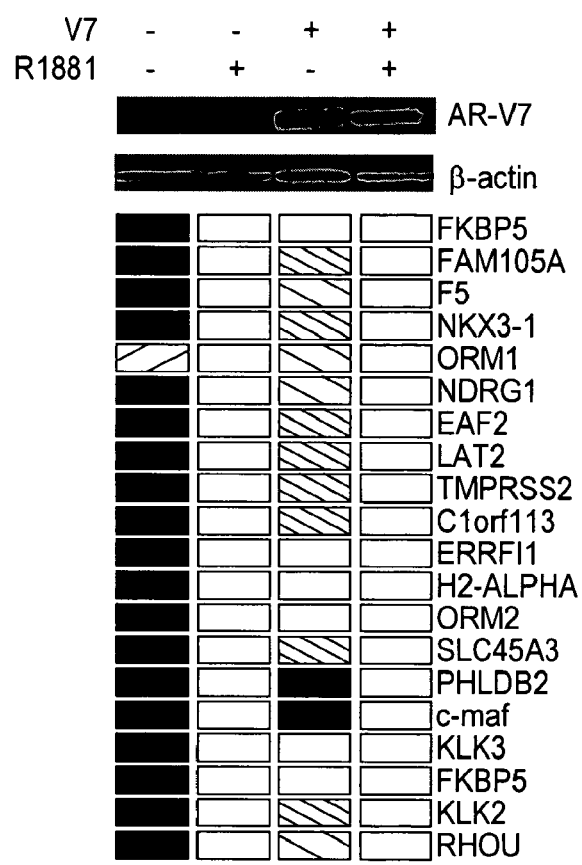
Figure 5:
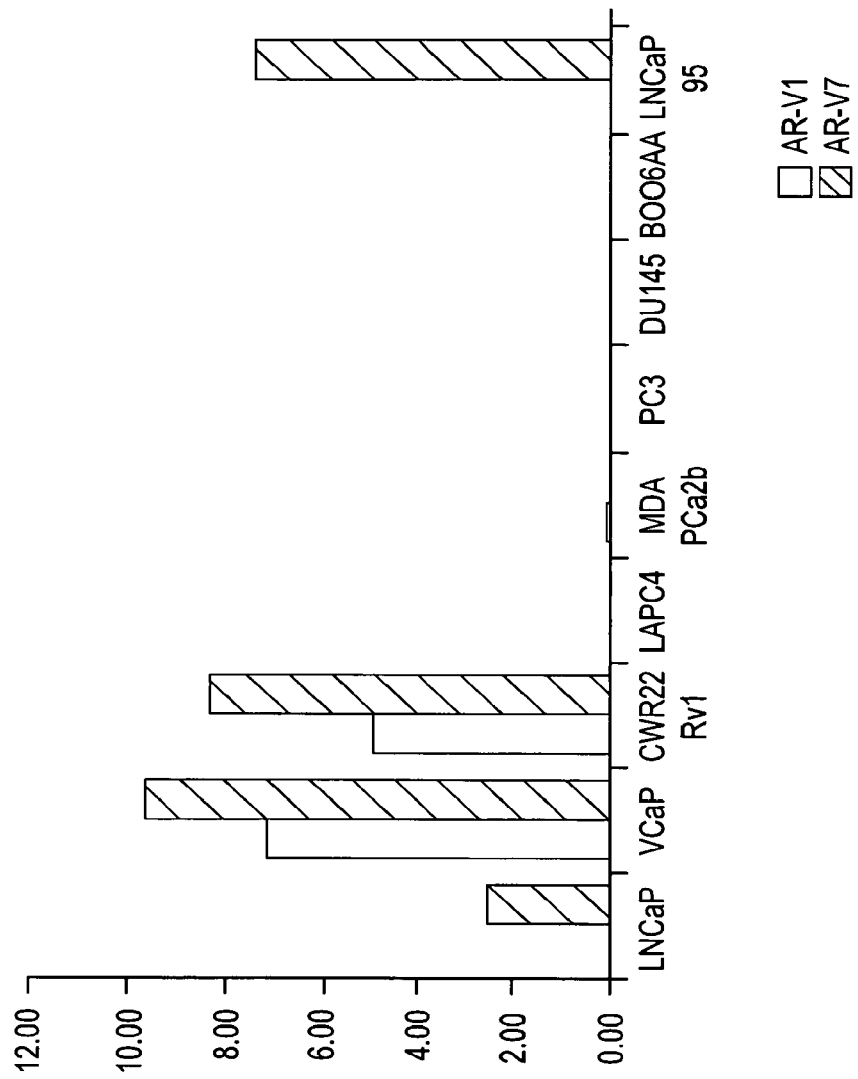
FIG. 5 shows real time RT-PCR analysis of AR variants V1, and V7 in human prostate cancer cell lines. Normalized expression values (in log 2 scale) for AR-V 1 (blue) and AR-V7 (red) derived from comparative threshold analysis were shown in 9 human prostate cancer cells lines. LNCaP95 is an androgen-independent cell line derived from long-term continuous culture of LNCaP cells in androgen-depleted conditions, provided by Dr. Alan K. Meeker (Johns Hopkins University, Baltimore, Md.). VCaP and E006AA prostate cancer cells were provided by Dr. John T. Isaacs (Johns Hopkins University, Baltimore, Md.). Other human prostate cancer cells lines were obtained from the American Type Culture Collection (Rockville, Md.).
Figure 9A:
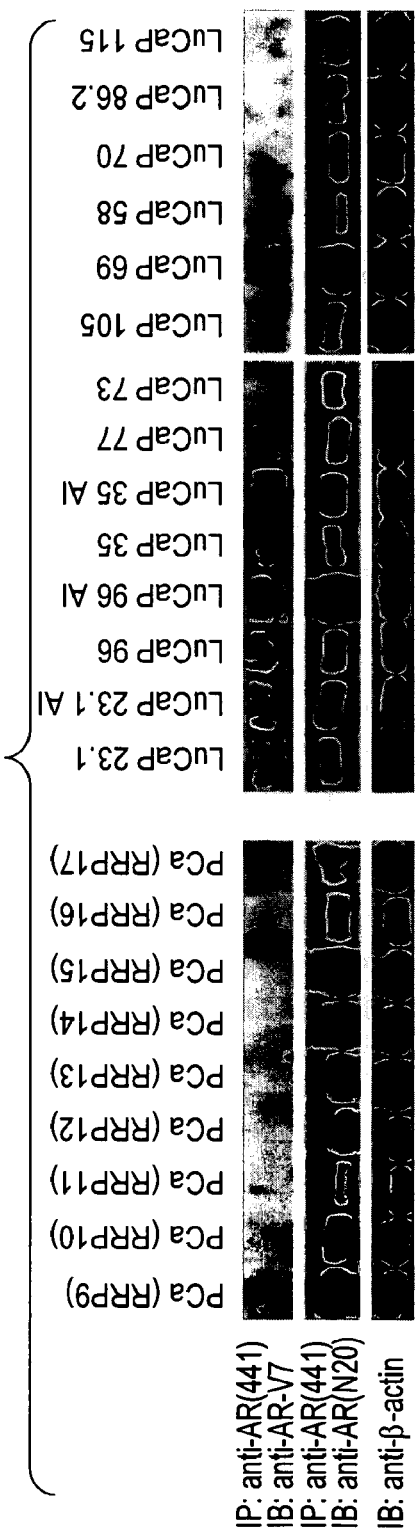
FIG. 9A-B shows protein (A) and mRNA (B) expression analysis in 9 hormone naïve RRP cases and 14 LuCaP human prostate cancer xenografts. Detection of AR-V7 and prototype AR protein was carried out using standard western immunoblots (IB) following enrichment of AR proteins by immunoprecipitation (IP) using the anti-AR(441) antibody, while detection of the control β-actin protein was carried out using regular protein lysate matched in quantity to the input lysate for IP. Note that data from different protein blots were not cross-comparable as experimental variables were different while the mRNA data should be comparable across the all samples as AR-V7 mRNA expression levels were normalized (in log 2 scale) and centralized to the median of the 82 RRP cases as presented in FIG. 2B. Xenografts specimens ending with AI (n=3) were androgen-independent derivative of the original xenograft following androgen ablation in the host animal. All xenografts originated from HRPC patients except LuCaP 58 and LuCaP 115, which were from hormone naïve lymph node metastasis.
Figure 9B:
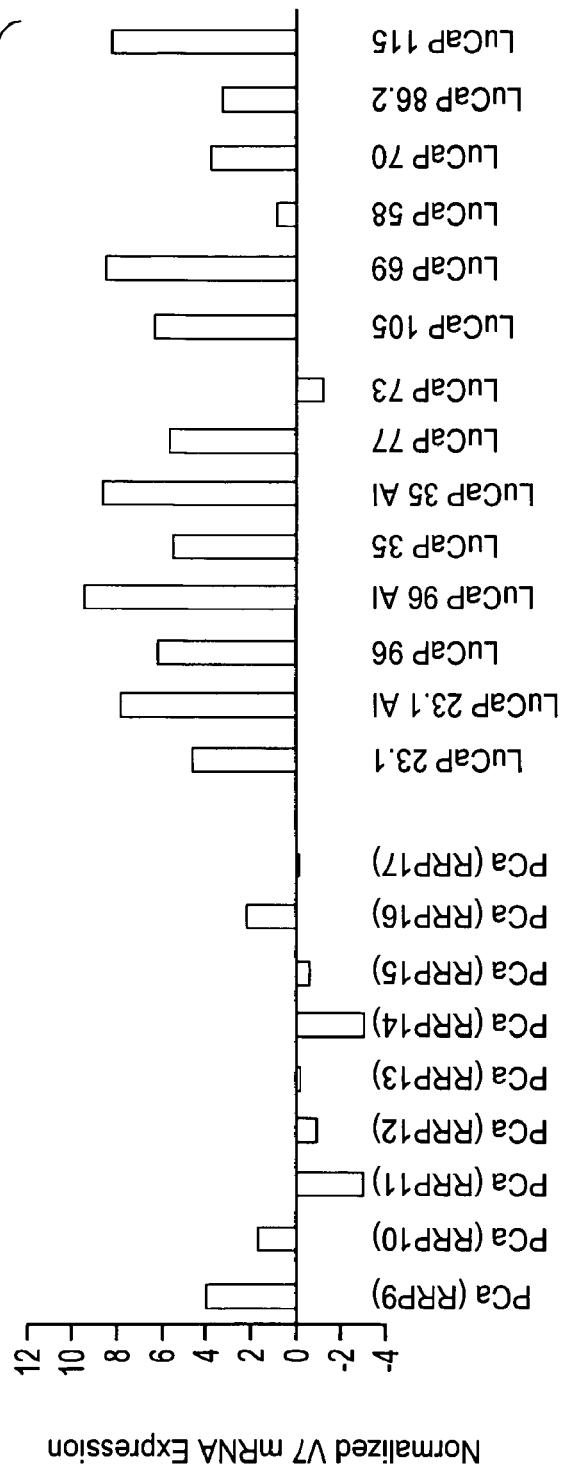

Transcript variants harboring PTC may be subjected to nonsense-mediated decay (16). Indeed, although similar transcript variants have been previously characterized for other steroid hormone receptor family members (17), no corresponding protein product has been reliably shown. Using the unique peptide sequence encoded by AR CE3, polyclonal antibodies were generated specifically against AR-V7. The antibodies recognized a single band of expected size (80 kDa) in VCaP and CWR22Rv1 cells (FIG. 3A), which expressed highest levels of AR-V7 mRNA (FIG. 5). Similarly, AR-V7 protein was detected in protein extracts from these two cell lines that were enriched for AR proteins by IP with an antibody against the AR NTD (FIG. 3B). In addition, the antibody detected the AR-V7 antigen in two clinical HRPC specimens using both whole tissue lysates and IP concentrated extracts (FIG. 3C). Moreover, using IP concentrated protein extracts, AR-V7 protein expression was detected in 10 of 14 human PCa xenografts, 12 of which were derived from HRPC patients (18), but in only 1 of the 9 hormone-naive radical prostatectomy specimens (FIG. 9). In CWR22Rv1 cells, small interfering RNA-mediated knockdown of AR-V7 expression or depletion of AR-V7 using anti-AR-V7 both resulted in significant reduction of the commonly observed f 80-kDa protein band but did not affect prototype AR expression (FIG. 10), suggesting nearly equivalent AR-V7 and prototype AR protein levels in this cell line. Although the prototype AR responded to the treatment of androgen by localizing to the nucleus, a large fraction of endogenous AR-V7 was localized in the nucleus in the absence of androgen and the proportion of nuclear AR-V7 did not change on androgen stimulation (FIG. 3D). The putative functional role of AR-V7 was investigated using exogenously transfected AR-V7 in AR-negative PC-3 cells. AR-V7 localized to the nucleus (FIG. 4A) and induced PSA reporter gene expression in an androgen-independent manner (FIG. 4B). Furthermore, in androgen-responsive LNCaP cells AR-V7 induced canonical androgen-responsive genes, such as KLK3, KLK2, NKX3-1, FKBP5, and TMPRSS2, in the absence of androgens, as shown by global gene expression analysis following transfection of the exogenous AR-V7 cDNA in LNCaP cells (FIG. 4C).

Figure 11:
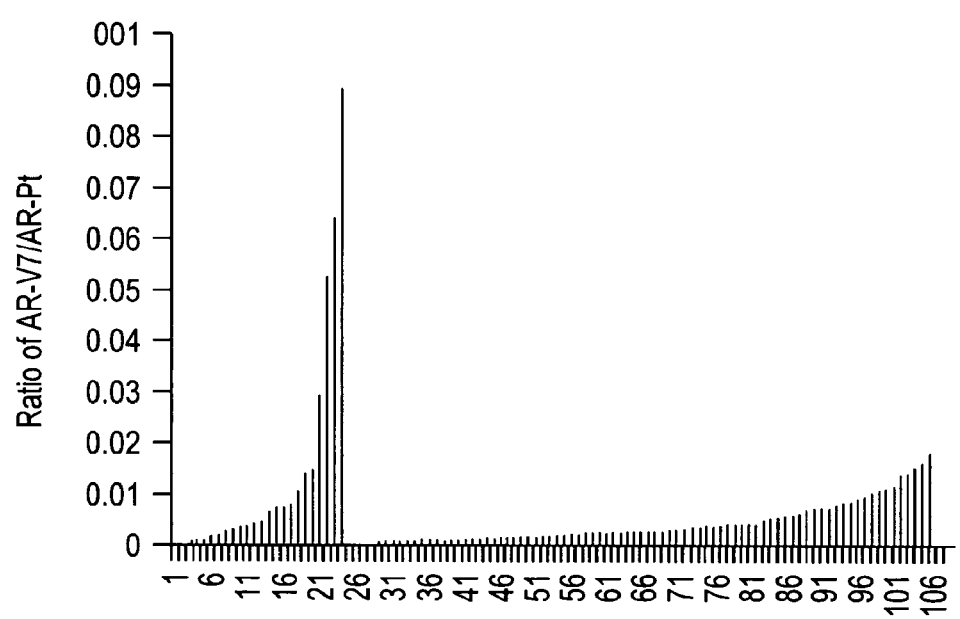
FIG. 11 shows the ratio of AR-V7 versus prototype AR (AR-pt) in 24 HRPC specimens (red) and 81 hormone naïve RRP cases (Blue). The cases were identical to those presented in FIG. 2B, expect that 2 cases were excluded due to uncalculable ratios. Despite a trend of higher AR-V7 versus prototype AR (AR-Pt) in a subset of HRPC specimens, the overall difference between RRP (median ratio 1:389) and HRPC (median ratio 1:238) specimens is not significant (p=0.0841, Mann-Whitney test). The absolute ratio values were calculated based on real-time RT-PCR expression values extrapolated upon standard curves of serial dilutions spanning 9 orders of magnitudes of known quantities of the target amplicons (plasmids harboring either AR-V7 or prototype AR).
Figure 12A:
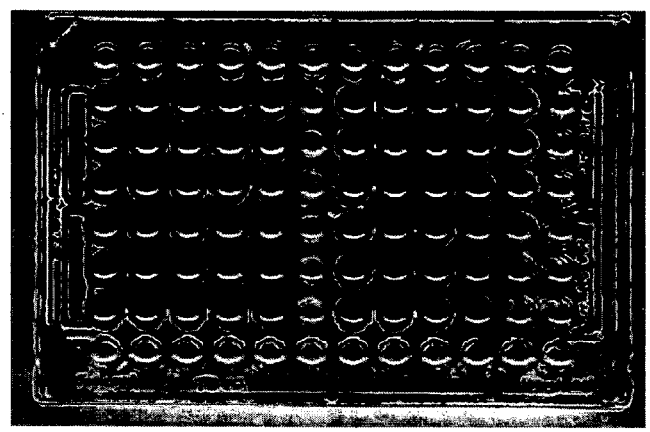
Figure 12C:
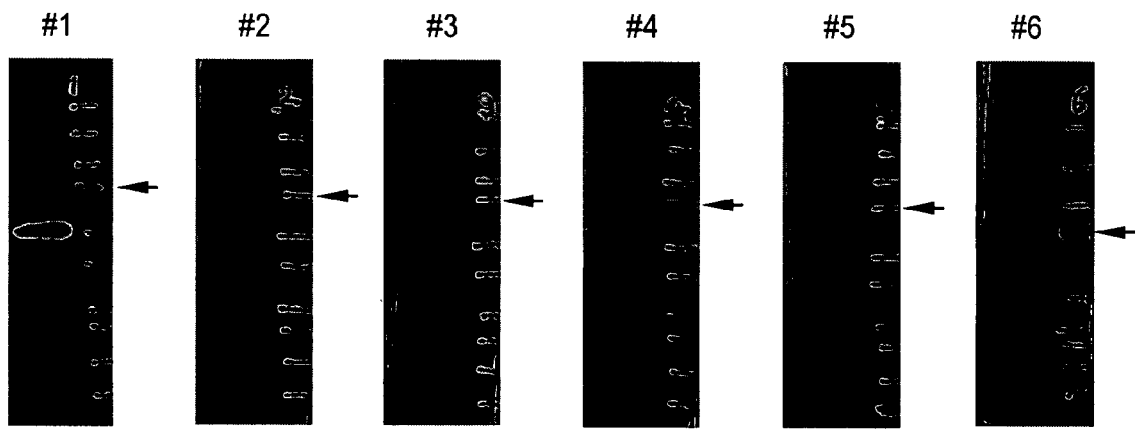
Figure 14A:
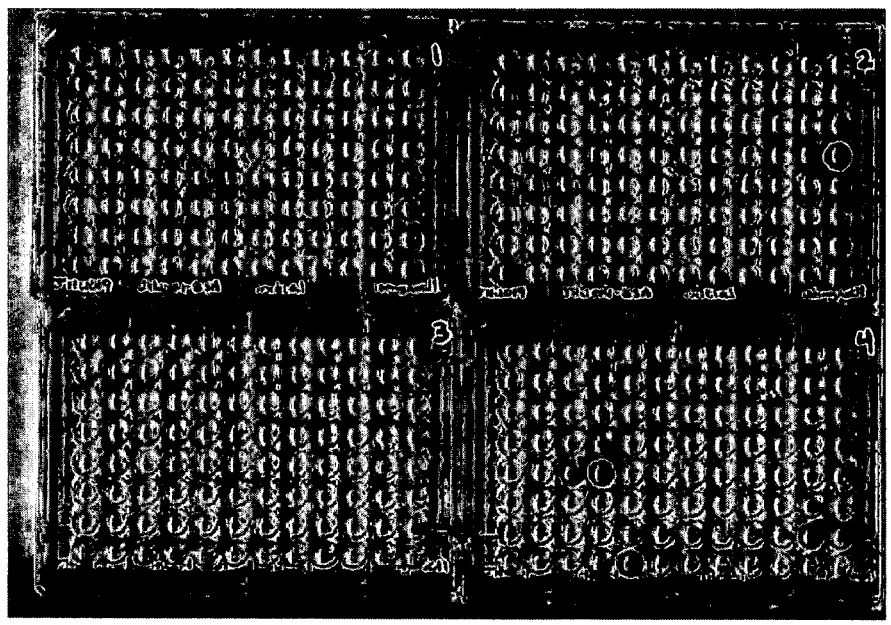
Figure 15A:
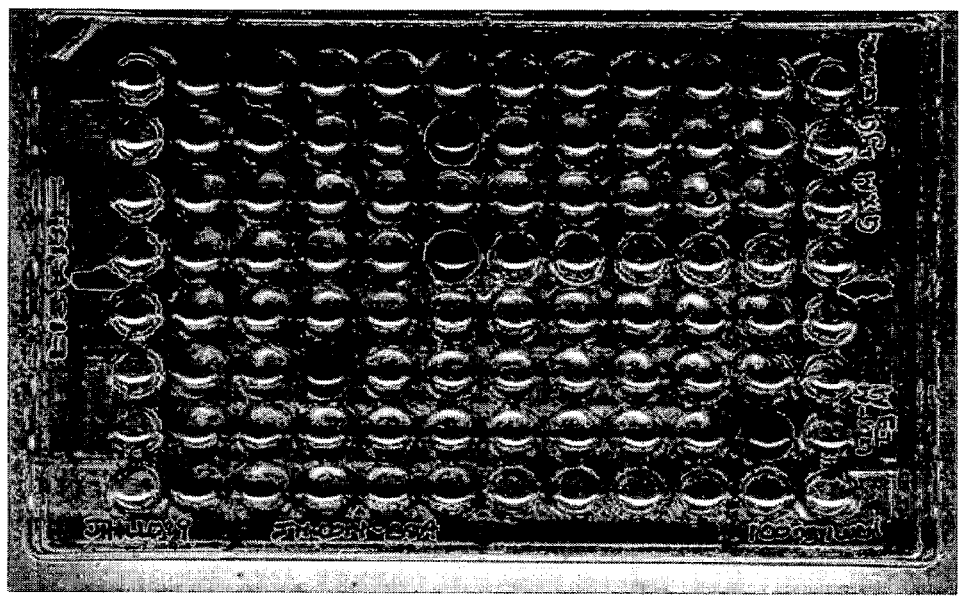
Figure 16:
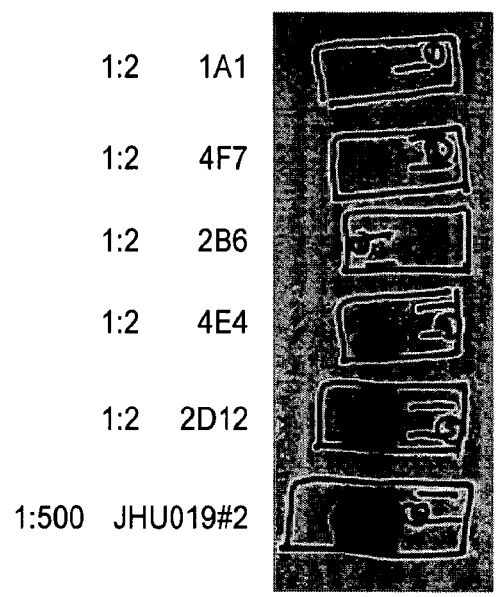
FIG. 16 shows selection of the positive monoclonal anti-AR-V7 hybridomas. Further confirmation of the 5 selected clones from FIG. 4. Whole cell lysates harvested from 293T cell transfected with AR-V7 over-expression plasmids were resolved on SDS-PAGE gel and transferred to PDVF membrane. Membrane slices (1 cm×1 cm) corresponding to the location of the 75 Kda bands were subjected to immuno blot with each individual hybridoma supernatant diluted 1:2. Ployclonal serum (JHU019) from mouse #2 was used as positive control. Based on this result, clone 2D12 was selected for expansion while the rest were discarded.
Figure 17:
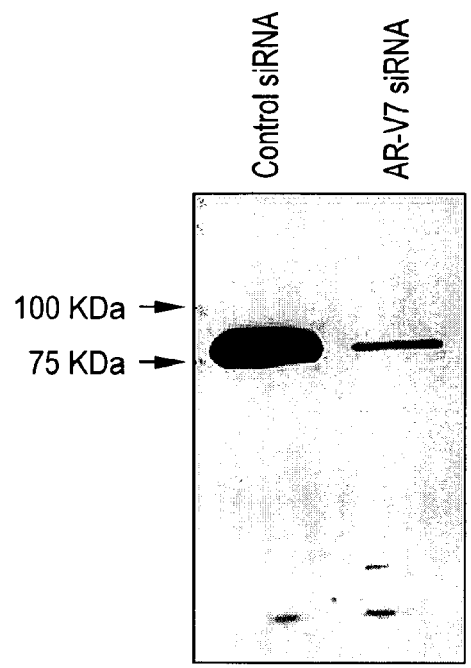
FIG. 17 shows confirmation of antibody specificity for clone 2D12. CWR22Rv1 cells were transfected with control siRNA or AR-V7 siRNA yo knockdwon endogenous AR-V7 expression. 96 hours later, whole cell lysates were harvested and subjected to immunoblot with 2D12 supernatantat 1:2 dilution.
Figure 18A:
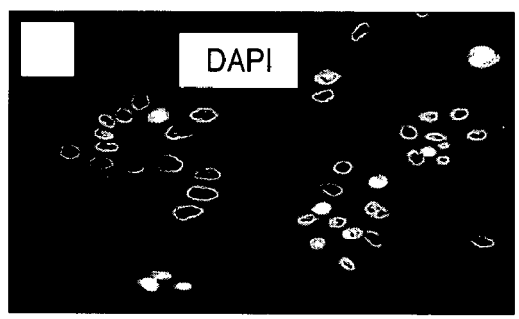
FIG. 18A-D shows in vivo staining of AR-V7 in CWR22Rv1 cells (A and B) and clinical prostate cancer specimens (C, D). Panel B shows immunofluorescent detection of AR-V7 predominantly in the nuclei of CWR22Rv1 cells (B). Panel A is DAPI staining to show the nuclei in the same cells. Panel C is a H&E stained section of hormone naïve prostate cancer specimen from a patient who later received and failed hormone therapy. This specimen is positive for AR-V7 protein expression as detected by immunoblots (supplemental data FIG. 5A of Hu et al. Cancer Research 69 (1):16-22, 2009). Shown in Panel D is the predominantly nuclear staining of AR-V7 and negative staining in the adjacent normal stromal tissues. Panel C and D are adjacent cuts of the same tissue block.
Figure 18C:
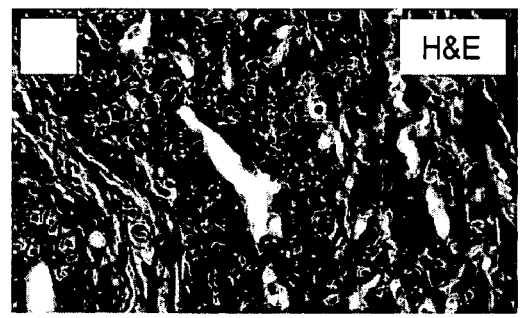
Figure 18B:
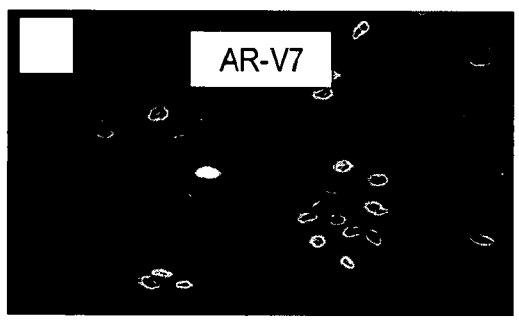
Figure 18D:
Figure 19A:
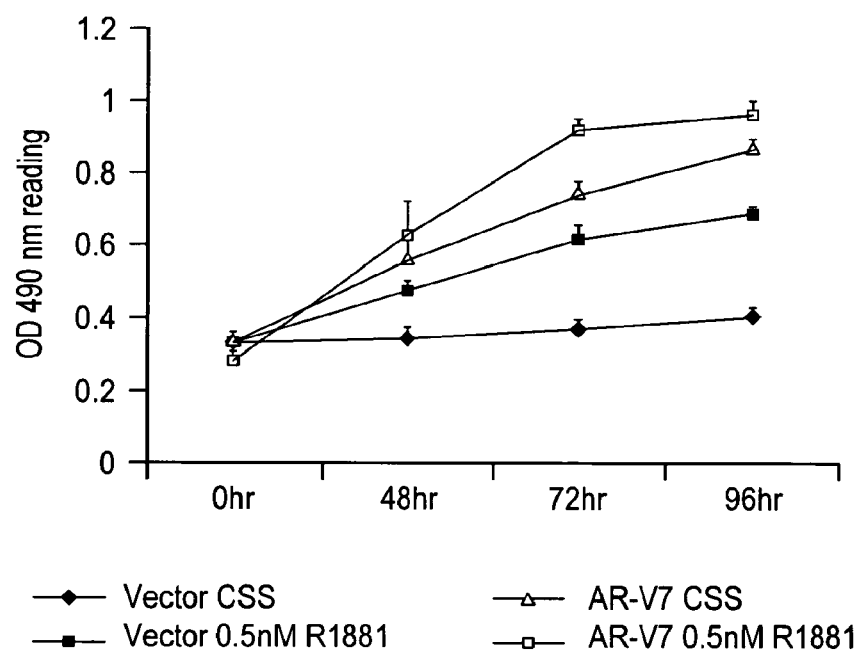
FIG. 19A-B shows AR-V7 promotes androgen independent growth of LNCaP cells. LNCaP cells were transfected by AR-V7 and the control vector. A. Cell growth in medium supplemented with charcoal stripped serum (CSS) in absence or presence of 0.5 nM R1881 were monitored by MTS assay. Ectopic expression of AR-V7 in LNCaP cells was confirmed by western blot analysis (B). As shown the growth rates of AR-V7 expressing cells surpassed those of parental cells cultured in the presence of synthetic androgen R1881.
Figure 19B:
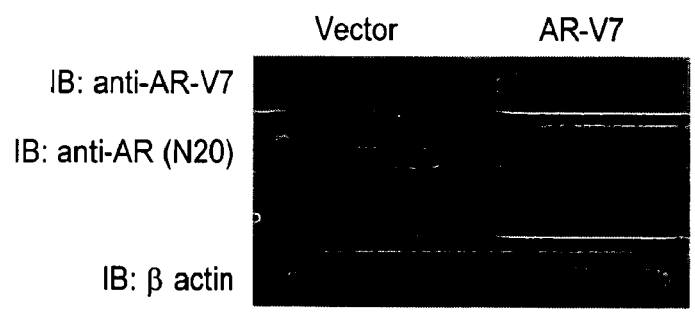

Hormonal therapy for advanced PCa is most commonly achieved by orchiectomy, systemic administration of LHRH agonists (e.g., leuprolide), and/or antiandrogens (e.g., bicalutamide). There are significant drawbacks associated with all existing androgen manipulation approaches. First, a variable period of clinical regression is followed by progression to HRPC, a lethal manifestation of the disease that is resistant to further therapies (4). Second, there are debilitating consequences from these treatments that must be considered when deciding whether and when to commence hormone therapy (2). Furthermore, sufficient levels of local androgens continue to be present in patients treated with combined androgen blockade (19). In spite of these challenges, hormone therapies remain the mainstay of treatment for patients with advanced PCa primarily due to the often dramatic clinical responses. The discovery of multiple LBD-truncated AR variants that mediate androgen-independent AR functions in HRPC and a subset of advanced but hormone-naive PCa adds another level of detail to the complex molecular mechanisms underlying the development of HRPC and may suggest new diagnostic and therapeutic approaches targeting this lethal disease. Indeed, these findings reinforce arguments for specific targeting of the AR NTD to achieve complete abrogation of AR signaling (20). Our quantitative mRNA data suggested that AR-V7 is a low-abundance variant relative to the prototype AR in the vast majority of clinical specimens, including HRPC (FIG. 11). The relative contribution of the prototype AR and the less abundant yet androgen-independent AR variants to the development of HRPC is currently unknown and will require detailed investigation. Nevertheless, the detection of such variants in proper target tissues or cells, on further refinement of the detection methods, may predict or monitor hormone therapy efficacy and could potentially help guide the decision-making process about the type and timing of therapies given to patients with advanced PCa.

Example 5

Development and Testing of the AR-V7 Monoclonal Antibody

It has been shown that AR-V7 is elevated by 20 fold following hormone therapy failure, and higher AR-V7 levels predict PSA recurrence (Hu et al. Cancer Research 69(1): 16-22, 2009). However, these findings were based on mRNA levels. In a clinical setting, determination of mRNA levels can be difficult. In addition, although polyclonal antibodies have been generated (Hu et al. Cancer Research 69(1):16-22, 2009), the polyclonal antibodies only worked for western blot and immunoprecipitation. The results described herein describe experiments focused on generating monoclonal antibodies against AR-V7. The results shown in FIGS. 12-19 demonstrate that clone 2D12 is highly specific for AR-V7, that 2D12 works in western blot, immunofluorescence, and immunohistochemistry. The availability of 2D12 made it possible to detect the antigen a clinically relevant setting. Diagnostic and prognostic assays using this antibody are to be developed and validated in prospective clinical trials.

Example 6

Discovery of AR-V8 Using Tiling Expression Microarray

Figure 20:
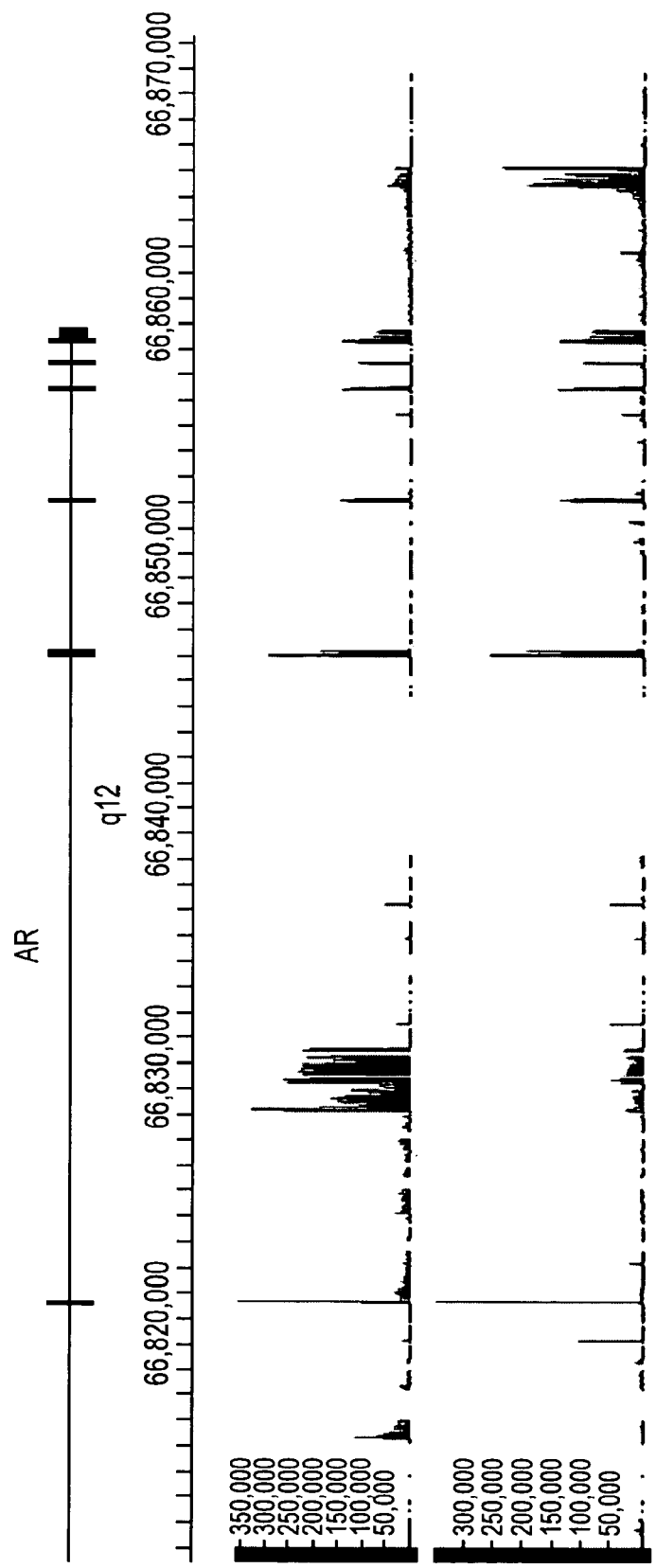
FIG. 20 shows tiling array results viewed by the Affyrnetrix Integrated Genome Browser. The canonical exons and intron boundaries are shown in relation to the genomic coordinates (HG18, March 2006 release) in the top strip and data from the CWR22Rv1 (yellow) cells and a hormone refractory prostate cancer specimen (TURP2) (blue) shown with the signal intensities (y axis) across the genomic coordinates (x axis) of the human AR gene. Note intense signal for AR-V7 variant specific sequences (the start position of the AR-V7 variant specific sequence is marked by an arrow), and the intense signal from AR-V8 specific sequences (the start position of the AR-V8 variant specific sequence is marked by an arrow) immediately upstream of AR-V7. The primer used to amplify AR-V8 is as follows: 5'-Tgtcactatggagctctcacatgtgg-3' and 5'-Cattgtggccaa-catgacacttca-3'.

The in silico based methods described above relied on deposited sequences in the public domain in the discovery phase, therefore are not comprehensive. It is possible that we had only captured a fraction of the AR variants. This incomplete profile of AR variant could limit the choices for biomarker validation and therapeutic development. To address these limitations, we interrogated the entire human androgen receptor gene and the immediate vicinity, ~200 kb in length, using genomic tiling arrays. This comprehensive approach, so far performed in two samples (CWR22Rv1 and TURP2), confirmed some of the previously characterized AR variants, and discovered a novel AR variant, AR-V8, that is abundantly expressed based on the overall signal intensity shown in FIG. 20. The splicing junctions for AR-V8 has been defined and variant specific nucleotide sequence has been validated (SEQ ID NO: 39) and the variant specific peptide sequence similarly deduced (SEQ ID NO: 40).

Materials and Methods

The Examples described herein were performed using, but not limited to, the following materials and methods.

Human Prostate Tissue Samples

Hormone-naive prostate tissue specimens used in this study (n=82) were collected and fresh frozen at the time of radical retropubic prostatectomy (RRP), from 1993 to 2001, at the Johns Hopkins Hospital. Prostate specimens were processed as described previously before RNA extraction (10). HRPC specimens were either collected at the time of the transurethral resection of the prostate (TURP) operation in patients who failed hormone therapies (n=4) or metastatic HRPC tissues (n=21) collected from 20 patients who died from PCa, as part of the Johns Hopkins Autopsy Study of lethal PCa (Supplementary Table 51; ref 11). The use of surgical and autopsy specimens for molecular analysis was approved by the Johns Hopkins Medicine Institutional Review Boards.

Cloning and Sequencing of AR Variants

First-strand cDNA synthesis was performed using 500 ng total RNA, 0.5 Ag oligo(dT), and 200 units of SuperScript II reverse transcriptase (Invitrogen) in a volume of 20 AL. PCR products derived from the primer pairs (Supplementary Table S2) were cloned into TopoTA vector (Invitrogen) and subjected to sequencing analysis using the Applied Biosystems 3730×1 DNA analyzer. To facilitate the amplification and sequencing of GC-rich AR NTD, DMSO (10%) was added in the PCR for full-length variant cloning and subsequent sequencing analysis.

AR Variant mRNA Expression Analysis

For semiquantitative reverse transcription-PCR (RT-PCR) analysis, 2.5% of the cDNA product from 500 ng input total RNA was used for each sample and each transcript. For real-time quantitative RT-PCR, 0.125% of the cDNA product was used in the iQ SYBR Green Supermix assays (Bio-Rad). Given the highly variable expression of many genes among clinical specimens, we analyzed previously published expression microarray data and identified SF3A3, which encodes a splicing factor, as a reference gene for normalization due to its stable expression levels among various prostate specimens, including HRPC, primary PCa, normal prostate samples, and cell lines (12). Only primer pairs with validated amplification specificity were used (Supplementary Table S2). Following validation of equal amplification efficiencies for both target transcripts and SF3A3, the average threshold cycle (Ct) numbers from reactions run in triplicate were used for comparative threshold analysis. For presentation purposes and for comparison among different figures, all expression values were log 2 transformed with measurable values for the RRP cases centered at zero.

AR Variant Protein Analysis

Whole-cell lysates were prepared using radioimmunoprecipitation assay buffer (Pierce) according to the vendor's recommendations. Nuclear and cytosolic extracts were prepared using the Nuclear and Cytoplasmic Extraction Reagents (Pierce). Protein samples were resolved on 4% to 12% gradient SDS-PAGE gels and subjected to standard immunoblot analysis with anti-AR(N20) (Santa Cruz Biotechnology), anti-AR-V7, or anti-beta-actin (Sigma-Aldrich) antibodies. The mouse polyclonal anti-AR-V7 antibody was developed using the COOH-terminal peptide (CKHLKMTRP) specific to the AR-V7 protein by a commercial vendor (A&G Pharmaceutical). For immunoprecipitation (IP), a total of 300 μg input whole-cell lysates from cell lines or human tissues was precipitated with 4 μg of monoclonal anti-AR(441) (Santa Cruz Biotechnology) or control mouse IgG, followed by the addition of protein G-agarose (GE Healthcare), and subjected to standard immunoblot analysis.

Luciferase Reporter Assay pEGFP-AR and pEGFP-Q640X, which contain the full-length prototype AR and AR Q640X LBD-truncated mutant cDNA, were kind gifts of Dr. Jocelyn Céraline (Université Strasbourg, Strasbourg, France). The cDNA encoding the full-length AR-V7 was inserted into the pEGFP-C3 vector to express the GFP-AR-V7 fusion protein. Each of these constructs was cotransfected together with the PSAP1 luciferase reporter plasmid and pRL-CMV plasmid, an internal Renila luciferase transfection control. Transfected cells were cultured in phenol red-free RPMI 1640 containing 10% charcoal-stripped serum (CSS) for 24 h and cultured for another 24 h in the presence or absence of R1881 (NEN) before being harvested and subjected to the Dual-Luciferase Reporter Assay (Promega).

Tiling Array Analysis

Tiling expression microarrays were designed to cover a 200 kb interval of the X chromosome (chrX:66,680,000-66,880,000) encompassing the entire human AR gene and the immediate vicinity, at 50 bp spacing with 10 bp overlap. Probes from both sense and antisense strands were included. Probes with repetitive elements and multiple hits in the human genome were excluded. The genomic sequences in FASTA text format were loaded to the Agilent eArray server under the simple tiling tab and processed for the manufacturing of this custom array. The routine labeling method involves incorporation of aminoallyl-dUTP during cDNA synthesis followed by coupling with monofunctional NHS-CyeS. The labeled products would hybridize against probes corresponding to the sense strand DNA. This method requires at least 20 μg of input RNA and is often limited by the low labeling efficiency especially for target transcripts with long 3' untranslated region (UTR). In addition, all transcripts (not just AR) would be labeled, increasing the likelihood of non-specific hybridization. The described method takes advantage of known distance between exon 1 and the start of cryptic exons. A modified T7 Eberwine primer with the core T7 promoter was used in second strand cDNA synthesis. Following an additional round of polyT primed DNA synthesis, double strand DNA templates with 5' binding sites for standard RNA linear amplification were generated. These labeled sense RNA will hybridize with antisense probes on the tiling array. The tiling array data was viewed with the Affymetrix Integrated Genome Browser.

Statistical Analysis

All data were analyzed using Stata v10.0 statistical analyses software (Stata Corp.). The Mann-Whitney test was used to evaluate distribution difference across two groups. Cox proportional hazard regression was used to identify significant prognostic factors for prediction of PCa progression-free survival. The proportional hazard assumption was verified by examination of residual plots and Schoenfeld residuals. Log rank was used to test equality of survivor functions across two groups. Statistical significance in this study was set as P V 0.05.

The present invention has been described in detail, including the preferred embodiments thereof. However, it will be appreciated that those skilled in the art, upon consideration of the present disclosure, may make modifications and/or improvements of this invention and still be within the scope and spirit of this invention as set forth in the following claims.

All publications and patent documents cited in this application are incorporated by reference in their entirety for all purposes to the same extent as if each individual publication or patent document were so individually denoted. By their citation of various references in this document, Applicants do not admit any particular reference is "prior art" to their invention.

The following specific references, also incorporated by reference, are indicated above by corresponding reference number.

1. Heinlein C A, Chang C. Androgen receptor in prostate cancer. Endocr Rev 2004; 25:276-308.
2. Gelmann E P. Molecular biology of the androgen receptor. J Clin Oncol 2002; 20:3001-15.
3. Shang Y, Myers M, Brown M. Formation of the androgen receptor transcription complex. Mol Cell 2002; 9:601-10.

4. Armstrong A J, Carducci M A. New drugs in prostate cancer. Curr Opin Urol 2006; 16:138-45.
5. Scher H I, Sawyers C L. Biology of progressive, castration-resistant prostate cancer: directed therapies targeting the androgen-receptor signaling axis. J Clin Oncol 2005; 23:8253-61.
6. Agoulnik I U, Weigel N L. Androgen receptor action in hormone-dependent and recurrent prostate cancer. J Cell Biochem 2006; 99:362-72.
7. Céraline J, Cruchant M D, Erdmann E, et al. Constitutive activation of the androgen receptor by a point mutation in the hinge region: a new mechanism for androgen-independent growth in prostate cancer. Int J Cancer 2004; 108:152.
8. Libertini S J, Tepper C G, Rodriguez V, Asmuth D M, Kung H J, Mudryj M. Evidence for calpain-mediated androgen receptor cleavage as a mechanism for androgen independence. Cancer Res 2007; 67:9001-5.
9. Dehm S M, Schmidt L J, Heemers H V, Vessella R L, Tindall D J. Splicing of a novel androgen receptor exon generates a constitutively active androgen receptor that mediates prostate cancer therapy resistance. Cancer Res 2008; 68:5469-77.
10. Luo J, Duggan D J, Chen Y, et al. Human prostate cancer and benign prostatic hyperplasia: molecular dissection by gene expression profiling. Cancer Res 2001; 61:4683-8.
11. Suzuki H, Freije D, Nusskern D R, et al. Interfocal heterogeneity of PTEN/MMAC1 gene alterations in multiple metastatic prostate cancer tissues. Cancer Res 1998; 58:204-9.
12. Dhanasekaran S M, Barrette T R, Ghosh D, et al. Delineation of prognostic biomarkers in prostate cancer. Nature 2001; 412:822-6.
13. Tepper C G, Boucher D L, Ryan P E, et al. Characterization of a novel androgen receptor mutation in a relapsed CWR22 prostate cancer xenograft and cell line. Cancer Res 2002; 62:6606-14.
14. Quigley C A, Evans B A, Simental J A, et al. Complete androgen insensitivity due to deletion of exon C of the androgen receptor gene highlights the functional importance of the second zinc finger of the androgen receptor in vivo. Mol Endocrinol 1992; 6:1103-12.
15. Zhou Z X, Sar M, Simental J A, Lane M V, Wilson E M. A ligand-dependent bipartite nuclear targeting signal in the human androgen receptor. Requirement for the DNA-binding domain and modulation by N H2-terminal and carboxyl-terminal sequences. J Biol Chem 1994; 269: 13115-23.
16. Pan Q, Saltzman A L, Kim Y K, et al. Quantitative microarray profiling provides evidence against widespread coupling of alternative splicing with nonsense-mediated mRNA decay to control gene expression. Genes Dev 2006; 20:153-8.
17. Hirata S, Shoda T, Kato J, Hoshi K. Isoform/variant mRNAs for sex steroid hormone receptors in humans. Trends Endocrinol Metab 2003; 14:124-9.
18. Saramäki O R, Porkka K P, Vessella R L, Visakorpi T. Genetic aberrations in prostate cancer by microarray analysis. IntJ Cancer 2006; 119:1322-9.
19. Montgomery R B, Mostaghel E A, Vessella R, et al. Maintenance of intratumoral androgens in metastatic prostate cancer: a mechanism for castration-resistant tumor growth. Cancer Res 2008; 68:4447-54.
20. Dehm S M, Tindall D J. Androgen receptor structural and functional elements: role and regulation in prostate cancer Mol Endocrinol 2007; 21:2855-63.
21. Huggins C, Hodges C V. Studies on prostatic cancer: I. The effect of castration, of estrogen and of androgen injection on serum phosphatases in metastatic carcinoma of the prostate. 1941. J. Urol.168(1), 9-12 (2002).
22. Maroni P D, Crawford E D. The benefits of early androgen blockade. Best Pract. Res. Clin. Endocrinol. Metab. 22(2), 317-329 (2008).
23. Fleming M T, Morris M J, Heller G, Scher H I. Post-therapy changes in PSA as an outcome measure in prostate cancer clinical trials. Nat. Clin. Pract. Oncol. 3(12), 658-667 (2006).
24. Chen Y, Sawyers C L, Scher H I. Targeting the androgen receptor pathway in prostate cancer. Curr. Opin. Pharmacol. 8(4), 440-448 (2008).
25. Small E J, Ryan C J. The case for secondary hormonal therapies in the chemotherapy age. J. Urol.176(6 Pt 2), 566-571 (2006).
26. Abrahamsson P A. Neuroendocrine cells in tumour growth of the prostate. Endocr. Relat. Cancer 6(4), 503-519 (1999).
27. Chen C D, Welsbie D S, Tran C et al. Molecular determinants of resistance to antiandrogen therapy. Nat. Med. 10(1), 33-39 (2004).
28. Linja M J, Visakorpi T. Alterations of androgen receptor in prostate cancer. J. Steroid Biochem. Mol. Biol. 92(4), 255-264 (2004).
29. Chmelar R, Buchanan G, Need E F, Tilley W, Greenberg N M. Androgen receptor coregulators and their involvement in the development and progression of prostate cancer. Int. J. Cancer 120(4), 719-733 (2007).
30. Kaarbo M, Klokk T I, Saatcioglu F. Androgen signaling and its interactions with other signaling pathways in prostate cancer. Bioessays 29(12), 1227-1238 (2007).
31. Mostaghel E A, Nelson P S. Intracrine androgen metabolism in prostate cancer progression: mechanisms of castration resistance and therapeutic implications. Best Pract. Res. Clin. Endocrinol. Metab. 22(2), 243-258 (2008).
32. Hu R, Dunn T A, Wei S et al. Ligand-independent androgen receptor variants derived from splicing of cryptic exons signify hormone-refractory prostate cancer. Cancer Res. 69(1), 16-22 (2009).

What is claimed is:

1. A method of detecting an androgen receptor variant 7 (AR-V7) having a nucleic acid sequence comprising SEQ ID NO: 1 or a fragment thereof, wherein the fragment comprises a portion of cryptic exon 3, in a human patient suffering from prostate cancer, the method comprising:
   a. obtaining a sample from the human patient, wherein the sample comprises mRNA;
   b. contacting the sample with one or more primers or probes, wherein at least one of the primers or probes specifically binds to the portion of cryptic exon 3 of the nucleic acid sequence comprising SEQ ID NO: 1 or the fragment thereof, and
   c. detecting the binding of the one or more primers or probes to the portion of cryptic exon 3 of the nucleic acid sequence comprising SEQ ID NO: 1 or a fragment thereof in the sample, thereby detecting AR-V7 in the human patient suffering from prostate cancer.

2. The method of claim 1, wherein the nucleic acid sequence detected comprises SEQ ID NO: 1.

3. The method of claim 1, wherein the step of detecting comprises detecting by nucleic acid amplification.

4. The method of claim 1, wherein the step of detecting comprises detecting by hybridization reaction.

5. The method of claim 4, wherein the hybridization reaction further comprises hybridizing the sample to one or more primer sets.

6. The method of claim 5, wherein the hybridization reaction is a polymerase chain reaction.

7. The method of claim 6, wherein the polymerase chain reaction is reverse transcription polymerase chain reaction.

8. The method of claim 1, wherein the step of detecting comprises detecting by expressed sequence tags.

9. The method of claim 1, wherein the step of detecting comprises detecting by microarray.

10. The method of claim 1, wherein the step of detecting comprises detecting by localization.

11. The method of claim 1, wherein the sample is a biological sample.

12. The method of claim 11, wherein the biological sample is a selected from the group consisting of: prostate cancer tissue biopsy, fresh or archival surgical specimens, circulating prostate tumor cells present in the blood, serum, urine and cell lines; or combinations thereof.

13. The method of claim 12, wherein the prostate cancer tissue biopsy is a tumor cell.

14. The method of claim 13, wherein the tumor cell is a prostate cancer cell.

15. The method of claim 1, wherein the prostate cancer is hormone naïve.

16. The method of claim 11, wherein the biological sample is a tumor sample previously treated with hormone therapy.

17. The method of claim 11, wherein the biological sample is from prostate.

18. The method of claim 11, wherein the biological sample is from a patient undergoing treatment for prostate cancer.

19. The method of claim 18, wherein the cancer is androgen refractory prostate cancer.

20. The method of claim 1, wherein the patient is in remission from prostate cancer.

21. The method of claim 1, wherein the expression level of SEQ ID NO: 1 or a fragment thereof is determined relative to that of SF3A3 or GAPDH.

22. The method of claim 1, further comprising after step a. and prior to step b. reverse transcribing the mRNA obtained in step a. to produce a cDNA product.

23. The method of claim 1, wherein the detection of the binding of the one or more primers or probes in step c. is performed by a reverse transcription polymerase chain reaction and wherein the sample is contacted by at least two primers, wherein at least one primer binds to the portion of cryptic exon 3.

24. The method of claim 1, wherein the one or more primers are: CTGTGGATCAGCTACTACCTTCAGCTC (SEQ ID NO: 20); or TTTGAATGAGGCAAGTCAGCCTTTCT (SEQ ID NO: 24).

25. The method of claim 1, wherein the one or more primers are a primer set selected from:

```
(P3)
                                    (SEQ ID NO: 19)
TGTCACTATGGAGCTCTCACATGTGG
and
                                    (SEQ ID NO: 20)
CTGTGGATCAGCTACTACCTTCAGCTC;
(P5)
                                    (SEQ ID NO: 23)
GTTGCTCCCGCAAGTTTCCTTCTC
and
                                    (SEQ ID NO: 24)
TTTGAATGAGGCAAGTCAGCCTTTCT;
or
(P7)
                                    (SEQ ID NO: 27)
CCATCTTGTCGTCTTCGGAAATGTT ATGAAGC
and
                                    (SEQ ID NO: 28)
TTTGAATGAGGCAAGTCAGCCTTTCT.
```

* * * * *